(12) United States Patent
     Bozkurt

(10) Patent No.: US 11,065,182 B2
(45) Date of Patent: Jul. 20, 2021

(54) RESIN COMPOSITE AND RESTORATION CONTAINING AZOLE-FUNCTIONALIZED SILICA

(71) Applicant: Imam Abdulrahman Bin Faisal University, Dammam (SA)

(72) Inventor: Ayhan Bozkurt, Dammam (SA)

(*) Notice: Subject to any disclaimer, the term of this patent is extended or adjusted under 35 U.S.C. 154(b) by 0 days.

(21) Appl. No.: 15/909,498

(22) Filed: Mar. 1, 2018

(65) Prior Publication Data

US 2019/0269580 A1    Sep. 5, 2019

(51) Int. Cl.
    *A61K 6/08*    (2006.01)
    *A61K 6/887*   (2020.01)
    *A61K 6/76*    (2020.01)

(52) U.S. Cl.
     CPC .............. *A61K 6/887* (2020.01); *A61K 6/76* (2020.01)

(58) Field of Classification Search
     CPC .................................................. A61K 6/0088
     See application file for complete search history.

(56) References Cited

U.S. PATENT DOCUMENTS

2015/0050473 A1* 2/2015 Seo .................. G03F 7/085
                                                    428/209

FOREIGN PATENT DOCUMENTS

| CN | 106732384 A | 5/2017 |
| CN | 104490609 B | 7/2017 |
| TR | 201313768 A | 6/2015 |

OTHER PUBLICATIONS

Aslan, A., et al., "Synthesis and Characterization of Novel Multifunctional SiO2 Nanoparticles", Advanced Materials: Techconnect Briefs 2015, 2 Pages total, (2015) (Abstract only).

* cited by examiner

*Primary Examiner* — Michael F Pepitone
(74) *Attorney, Agent, or Firm* — Oblon, McClelland, Maier & Neustadt, L.L.P.

(57) ABSTRACT

A resin composite containing azole-functionalized silica nanoparticles. The resin composite further includes a polymerizable monomer and a polymerization initiator system. A dental restoration fabricated by curing the resin composite is also specified.

19 Claims, 52 Drawing Sheets

DMT

N,N-dimethyl-p-toluidine

DMPOH

4-N,N-dimethylaminophenethyl alchohol

DMAPAA

4-N,N-dimethylaminophenylacetic acid

EDMAB

Ethyl 4-dimethylaminobenzoate

RESIN COMPOSITE AND RESTORATION CONTAINING AZOLE-FUNCTIONALIZED SILICA

STATEMENT REGARDING PRIOR DISCLOSURE BY THE INVENTORS

Aspects of this technology are described in a Master of Science thesis titled "Synthesis and characterization of multi-functional azole silica based nanocomposites for dental application" [Umar Safiyanu YUSHA'U MS Thesis, 2017; supervisor: Prof. Dr Ayhan Bozkurt] with a public disclosure date on Mar. 1, 2017, which is incorporated herein by reference in its entirety.

BACKGROUND OF THE INVENTION

Technical Field

The present disclosure relates to a resin composite including azole-functionalized silica nanoparticles and a dental restoration based on the cured resin composite.

DESCRIPTION OF THE RELATED ART

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

The goal of dental technology and dentistry is to sustain and enhance life qualities of dental patients. This objective can be achieved by relieving pain, preventing disease, improving chewing efficiency, improving speech capability and enhancing appearance. There may be a need for replacing or reshaping tooth structure to achieve many of these goals. To endure a harsh oral environment, a durable, biocompatible, indirectly processed prosthetic and direct filling tooth restorative material is desirable (Anusavice, K., "Informatics systems to assess and apply clinical research on dental restorative materials", Advances in dental research, vol. 17, pp. 43-48, 2003).

In the past, a variety of materials have been used as tooth crowns and root replacements such as ivory seashells, human teeth, bone, metals and ceramics. Natural biomaterials are of use in biomimetics and implants because of their similarities with tissues and lack of toxicity (Oliveira, J. T., and Reis, R., "Polysaccharide-based materials for cartilage tissue engineering applications", Journal of tissue engineering and regenerative medicine, vol. 5, pp. 421-436, 2011). However, due to the tendency for natural polymers to decompose or denature at temperatures below their melting point, the production of implants of different sizes and shapes are restricted (International, A., and Davis, J. R. Handbook of materials for medical devices, ASM international, 2003). Major classes of materials used currently in dentistry are composites, ceramic, metals and polymers. Metals are a class of synthetic biomaterial with useful properties such as strength, malleability and hardness. They are usually applied in dentistry and medicine as implantable or prosthetic materials. Metals are rigid and tough with high modulus of elasticity and shear. They can be easily fabricated into usable forms. The utilization of alloys and special fabrication technique gives wide alternatives of choices in choosing the best metals for a particular use (Ferracane, J. L. Materials in dentistry: principles and applications, Lippincott Williams & Wilkins, 2001a). Alloys of metals have gained a particular interest as dental and orthopedic implants because they are well accepted by body, partially due to the comparatively nonreactive surfaces (Ratner, B. D., Hoffman, A. S., Schoen, F. J., and Lemons, J. E. Biomaterials science: an introduction to materials in medicine, Academic press, 2004). Metals are used largely as structural parts for the replacement or restoration of tooth structure. Metals are most often used in the posterior part of the mouth where the metallic color is not commonly seen. Moreover, they are more conventionally used to change parts of a tooth. An inlay is formed if the component of the tooth to be changed is in the cusps. Generally, the remaining teeth are used as support for metallic bridges which extend to the free spaces to fill in the arch. Dental cement with teeth is permanently fixed on these bridges. They are called fixed partials because they replace a component of dentition (Ferracane, J. L. (2001b). Materials in dentistry: principles and applications. Lippincott Williams & Wilkins).

Ceramic materials used in dentistry are either synthetic or natural and can imitate natural teeth. The major constituents of ceramics materials used in dentistry and porcelain are kaolin, feldspar, and quartz. Ceramics have a lower toughness compared to metals. They are rigid with poor thermal and electrical conduction. Dental restoration can be made by casting ceramics. For applications where color and translucency are important, the opacity and translucency of dental ceramic can be tailored (Powers, J. M., and Sakaguchi, R. L. Craig's restorative dental materials, 13/e, Elsevier India, 2006a). The composition, microstructure, and flaw population of dental ceramics determine its properties. Ceramics used in dentistry undergo cyclic or repeated loading in wet surroundings during chewing. This situation causes the already existed defects or cracks to expand. This phenomenon is called slow growth, which causes an additional severe decrease of survival probability of ceramic restorations.

In dentistry, polymers are used frequently for various applications in tooth restoratives, cements, sealants, orthodontic space maintainers, elastics and obturators for cleft palate, impressions, provisional restorations, root canal filling materials, denture bases, and athletic mouth protectors. Polymers are mainly organic substances which are bulky molecules with repeating units. They can be categorized as organic and inorganic (Table 1). Presently, synthetic polymers are used in most industries and are ubiquitous in everyday life (Allcock, H. R. Chemistry and applications of polyphosphazenes, Wiley-Interscience, 2003).

TABLE 1

Classification of polymers

| | Inorganic | | Organic |
|---|---|---|---|
| Synthetic | Fibers | Synthetic | Adhesive, fibers, coatings, rubbers |
| Natural | Sands: glass Clays: bricks, Cement, pottery | Natural | Proteins: adhesives, fibers Polysaccharides: adhesives, fibers. Polyisoprene: rubber |

Even with recent improvements in their physical properties, none of the materials discussed above are permanent. An ideal restorative material should be biocompatible, look like the original tooth, show similarity in properties as tooth components such as dentine, enamel and other tissues, and be capable of initiating tissue repair or regenerating missing or damaged tissues.

In the past 40 years, due to poor aesthetics, regular utilization of dental amalgam has been gradually decreasing particularly for anterior restoration. Additional concerns include mercury toxicity, environmental pollution by mercury disposal, potential dental fracture, secondary caries, and marginal leakage. Dental composites are synthetic resins used as adhesives and prosthetic materials in dentistry, which now represent an alternative to dental amalgam. Hlowever, composites have limited uses because of their low durability and strength (Abell, A., Leinfelder, K., and Turner, D., "Microscopic observations of the wear of a tooth restorative composite in vivo", Journal of biomedical materials research, vol. 17, pp. 501-507, 1983; Bernardo, M., Luis, H., Martin, M. D., Leroux, B. G., Rue, T., Leitão, J., and DeRouen, T. A., "Survival and reasons for failure of amalgam versus composite posterior restorations placed in a randomized clinical trial", The Journal of the American Dental Association, vol. 138, pp. 775-783, 2007; and Leinfelder, K. F., "New developments in resin restorative systems", The Journal of the American Dental Association, vol. 128, pp. 573-581, 1997). Durability and survival studies have shown a superiority of amalgam over composite. The overall endurance rate for a composite in permanent teeth was 67.4% compared to 94.5% for amalgam restoration after 7 years. Dental amalgam has a flexural strength of over 400 Mpa, whereas flexural strength of dental composites ranges from 80 to 120 MPa. As a result, composites can satisfy needs for small restorations but cannot survive large stress bearing restorations (Berry, T. G., Nicholson, J., and Troendle, K., "Almost two centuries with amalgam: Where are we today?", The Journal of the American Dental Association, vol. 125, pp. 392-399, 1994; and Corbin, S. B., and Kohn, W. G., "The benefits and risks of dental amalgam: current findings reviewed", The Journal of the American Dental Association, vol. 125, pp. 381-388, 1994).

The quest for an aesthetic and efficient restoration has been made possible due to development of resin-based composites (RBC), which was started by the introduction of dental resin bis-GMA. The emergence of other resins has further helped to tackle problems such as low hardness, contraction due to polymerization, and signs of wear since the introduction of bis-GMA. In addition, the size of inorganic filler particles is another important aspect that can be optimized. Due to large particle size of fillers used, the first generation dental composites demonstrated poor resistance to wear and had a rough surface, yielding them unfit for posterior restoration applications. Micro-filled composites containing silica with particle size of about 0.04 µm were developed in 1970's to produce a lustrous surface with an enhanced wear resistance.

To further improve clinical performance of dental resin composites, various attempts have been undertaken (Moszner, N., and Salz, U. New developments of polymeric dental composites, 2001). Impacts of the amount of filler, particle size, silanization technique, loading method, (Ikejima, I., Nomoto, R., and McCabe, J. F., "Shear punch strength and flexural strength of model composites with varying filler volume fraction, particle size and silanation", Dental Materials, vol. 19, pp. 206-211, 2003) and novel particles on dental composite (Ruddell, D., Maloney, M., and Thompson, J., "Effect of novel filler particles on the mechanical and wear properties of dental composites", Dental Materials, vol. 18, pp. 72-80, 2002; and Xu, H. HI., Quinn, J. B., Smith, D. T., Antonucci, J. M., Schumacher, G. E., and Eichmiller, F. C., "Dental resin composites containing silica-fused whiskers-effects of whisker-to-silica ratio on fracture toughness and indentation properties", Biomaterials, vol. 23, pp. 735-742, 2002) were investigated. Research on the polymer matrix is essentially focused on synthesis of new monomers (Atai, M., Nekoomanesh, M., Hashemi, S., and *Amani*, S., "Physical and mechanical properties of an experimental dental composite based on a new monomer", Dental Materials, vol. 20, pp. 663-668, 2004; Chung, C.-M., Kim, J.-G., Kim, M.-S., Kim, K.-M., and Kim, K.-N., "Development of a new photocurable composite resin with reduced curing shrinkage", Dental Materials, vol. 18, pp. 174-178, 2002; and Taylor, D., Kalachandra, S., Sankarapandian, M., and McGrath, J., "Relationship between filler and matrix resin characteristics and the properties of uncured composite pastes", Biomaterials, vol. 19, pp. 197-204, 1998). Physical properties of a dental composite rely immensely on the particle size and filler volume as polymerization shrinkage decreases, while hardness, compressive strength, elastic modulus and flexural strength increase as filler volume fraction increases.

Resin based composites are categorized in different ways based on their composition. A most popular classification was introduced by Lutz and Philips in 1983, which is based on the particle size of inorganic filler (Lutz, F., and Phillips, R. W., "A classification and evaluation of composite resin systems", The Journal of prosthetic dentistry, vol. 50, pp. 480-488, 1983). Resin composites are categorized into three main groups: hybrid, micro-filled and macro-filled composites. Dental resin composites can also be classified as chemically activated composites, light activated composites, heat-cured composite or dual cured composites. Willems et al. published a more detailed classification (Table 2) based on considerations including main particles size, the percentage of inorganic filler, surface roughness, and compressive strength (Willems, G., Lambrechts, P., Braem, M., Celis, J.-P., and Vanherle, G., "A classification of dental composites according to their morphological and mechanical characteristics", Dental Materials, vol. 8, pp. 310-319, 1992). A simpler grouping system (Table 3) was described by Bayne et al in 1994 (Bayne, S. C., Heymann, H. O., and Swift, E. J., "Update on dental composite restorations", The Journal of the American Dental Association, vol. 125, pp. 687-701, 1994).

TABLE 2

Classification of composites

| Composite type | Filler |
| --- | --- |
| Micro fine composites:<br>Homogeneous<br>Heterogeneous | Average particle size = 0.04 µm |
| Traditional composites | Equivalent to what are termed macro fill composites in other classifications |
| Miscellaneous composites | Blends of densified and micro fine composites |
| Fiber-reinforced composites | Industrial-use composites |
| Densified composites: | |
| Midway-filled | <60% by volume Particles |
| Ultrafine | <3 µm Particle |
| Fine | >3 µm |
| Compact-filled (>60% by volume): | >60% by volume Particles |
| Ultrafine | <3 µm Particles |
| Fine | >3 µm |

TABLE 3

Classification of composites according to Bayne et al., 1994.

| Types of composite | Average particle size |
|---|---|
| Microfils | 0.01-0.1 μm |
| Minifills | 0.1-1.0 μm |
| Midfill | 1.0-10.0 μm |

Macro-filled resin composites contain inorganic fillers with a particle size of 10-40 μm. They have drawbacks such as relatively high wear and poor finish. Barium or strontium glass and quartz are mainly utilized fillers in these composites. Quartz fillers possess good appearance and stability, but have problems including absence of radiopacity and high wear. Strontium and barium glass particles are less stable than quartz but radiopaque (Lindberg, A. Resin composites: sandwich restorations and curing techniques. Umea University, 2005). Micro-filled type composite was launched to meet the need for polishable resin based composite. Micro-filled composites made from colloidal silica contain very fine particles with a size of 0.01-0.05 μm. However, the volume of filler that can be incorporated is restricted because of large surface area of the particles. Due to large resin volumes, micro-filled composites have lower mechanical properties when compared to macro-filled resin composites. Hybrid resin composites were launched to tackle the mechanical and contraction issues of resin based composites. The first hybrid resin composite contains large fillers with particle sizes of 15-20 μm and colloidal silica particles of 0.01-0.05 μm. Current hybrid composites are made up of reduced submicron fillers. These composites combine the strengths of both macro-filled and micro-filled composites.

Nanocomposites are developed recently, which consist of fillers with particle sizes of less than 10 nm (0.01 μm). They are expected to have increased strength, good appearance and toughness. Nanocomposites are available in nano-hybrid and nano-fill types. Nano-hybrid composite contains milled discrete nanoparticles (40-50 nm) and glass fillers, while nano-fill composite contains mixed nanomers and nanoclusters, which consist of nano-sized filler particles and agglomerates of filler particles, respectively (Mitra, S. B., Wu, D., and Holmes, B. N., "An application of nanotechnology in advanced dental materials", The Journal of the American Dental Association, vol. 134, pp. 1382-1390, 2003). The nanocluster gives a unique supportive mechanism hence provides a considerable enhancement to the strength and consistency of the composites.

TABLE 4

Materials and filler sizes

| Type of Composite | Filler material | Filler size (μm) |
|---|---|---|
| Hybrid | Glass and colloidal silica | 15-20 and 0.01-0.05 |
| Modern hybrid | Glass, Zirconia and colloidal silica | 0.5-1 and 0.01-0.05 |
| Microfilled | Colloidal silica | 0.01-0.1 |
| Nanofiller | Silica or Zirconia | <0.01 (10 nm) |
| Macrofilled | Quartz or glass | 10-40 |

Dental resin composites may be classified based on their mode of activation. Products that can be activated chemically are supplied frequently as two pastes which are combined before use. Each paste has a premixed resin and fillers. One paste consists of approximately 1% initiator, e.g. benzoyl peroxide while the other paste contains an aromatic tertiary amine activator such as p-tolyldiethanolamine or N,N-diemthyl-p-toluidine (McCabe, J. F., and Walls, A. W. Applied dental materials, John Wiley & Sons, 2013). Products that can be activated by light are usually provided as a single paste that consists of an initiator, monomers, and co-monomers. The utilization of UV-activated material has decreased significantly due to potential damages caused by long term UV exposure. Visible light activated dental resin composites are more frequently used (Stansbury, J. W., "Curing dental resins and composites by photopolymerization", Journal of esthetic and restorative dentistry, vol. 12, pp. 300-308, 2000). The initiator used is often a mixture of an amine such as dimethylaminoethyl methacrylate (DMAEMA) and a diketone such as camphorquinone. In the presence of the amine, camphorquinone absorbs blue light (400-500 nm) and generates free radicals (Cramer, N., Stansbury, J., and Bowman, C., "Recent advances and developments in composite dental restorative materials", Journal of Dental Research, vol. 90, pp. 402-416, 2011). To prevent or minimize accidental or spontaneous polymerization of monomers, inhibitors are often included to resin systems to extend the material's shelf life. Dual cured materials combine chemical and light activation curing modes.

ISO 4049 standard for resin-based restorative materials categorizes materials into two types based on their application. Type I is intended for restorations of cavities involving the occlusal surface by manufacturers, while Type II comprises other restorative materials and polymer-based fillings. As shown in table 5, these materials are further divided into three categories: classes 1, 2, and 3.

TABLE 5

Requirement for polymer based filling and restorative materials based on ISO 4049 standard

| Property | Class 1 | Class 2 | Class 3 |
|---|---|---|---|
| Working time (min/sec) | 90 | — | 90 |
| Setting time (max/min) | 5 | — | 10 |
| Depth of cure | — | 1.0 | — |
| Other Shades | — | 1.5 | — |
| Water Sorption (max μg/mm$^3$) | 40 | 40 | 40 |
| Solubility (max μg/mm$^3$) | 7.5 | 7.5 | 7.5 |
| Flexural Strength: | | | |
| Type 1 | 80 | 80 100 | 80 |
| Type 2 | 50 | 50 | 50 |

In view of the forgoing, one objective of the present disclosure is to provide a resin composite and a dental restoration thereof that contains a polymerizable monomer, azole-functionalized silica nanoparticles, and a polymerization initiator system.

BRIEF SUMMARY OF THE INVENTION

According to a first aspect, the present disclosure relates to a resin composite comprising (i) a polymerizable monomer, (ii) a polymerization initiator system, and (iii) azole-functionalized silica nanoparticles in an amount ranging from 5 wt % to 75 wt % relative to a total weight of the resin composite, wherein the azole-functionalized silica nanoparticles are a ring-opening reaction product of silica nanoparticles modified with epoxide groups and an azole moiety.

In one embodiment, the silica nanoparticle modified with epoxide groups is represented by formula (I)

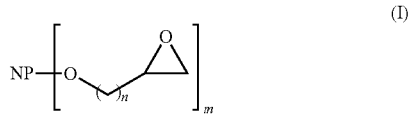

wherein NP represents a silica nanoparticle, n is a positive integer in a range of 1-6, and m is a positive integer in a range of 2-1000.

In one embodiment, silica is present in an amount of 20-50 wt % relative to a total weight of the azole-functionalized silica nanoparticle.

In one embodiment, the azole moiety is present in an amount of 40-80 wt % relative to a total weight of the azole-functionalized silica nanoparticle.

In one embodiment, n is 1.

In one embodiment, the azole moiety is at least one selected from the group consisting of 1H-1,2,4-triazole, 3-amino-1,2,4-triazole, 5-aminotetrazole, and imidazole.

In one embodiment, the azole-functionalized silica nanoparticle has an average diameter of 20-100 nm.

In one embodiment, the polymerizable monomer is at least one selected from the group consisting of a methacrylate monomer, an acrylate monomer, an epoxy monomer, and a vinyl monomer.

In one embodiment, the polymerizable monomer is a methacrylate monomer.

In one embodiment, the methacrylate monomer is at least one selected from the group consisting of bisphenol A-glycidyl methacrylate (bis-GMA), ethoxylated bisphenol A dimethacrylate (bis-EMA), urethane dimethacrylate (UDMA), triethylene glycol dimethacrylate (TEGDMA), 1,12-dodecanediol dimethacrylate (D₃MA), bismethacryloyloxymethyltricyclo-[5.2.1.]decane (TCDMA), and 2-hydroxyethyl methacrylate (HEMA).

In one embodiment, the polymerization initiator system comprises a free radical initiator.

In one embodiment, the polymerization initiator system further comprises a polymerization accelerator.

In one embodiment, the polymerization initiator system consists of camphorquinone and ethyl 4-(dimethylamino)benzoate.

In one embodiment, the resin composite further comprises a filler which is at least one selected from the group consisting of a glass filler, a ceramic filler, and a polymer-based filler.

According to a second aspect, the present disclosure relates to a dental restoration comprising a cured resin composite.

In one embodiment, the dental restoration has a compression strength of 40-400 MPa.

In one embodiment, the dental restoration has a strain at break of 4.0-13 GPa.

In one embodiment, the dental restoration has an elastic modulus of 0.4-11 GPa.

In one embodiment, the dental restoration has a water solubility of 0.002-0.4 mg/mL.

In one embodiment, the dental restoration has a water sorption of 0.02-0.4 mg/mL.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
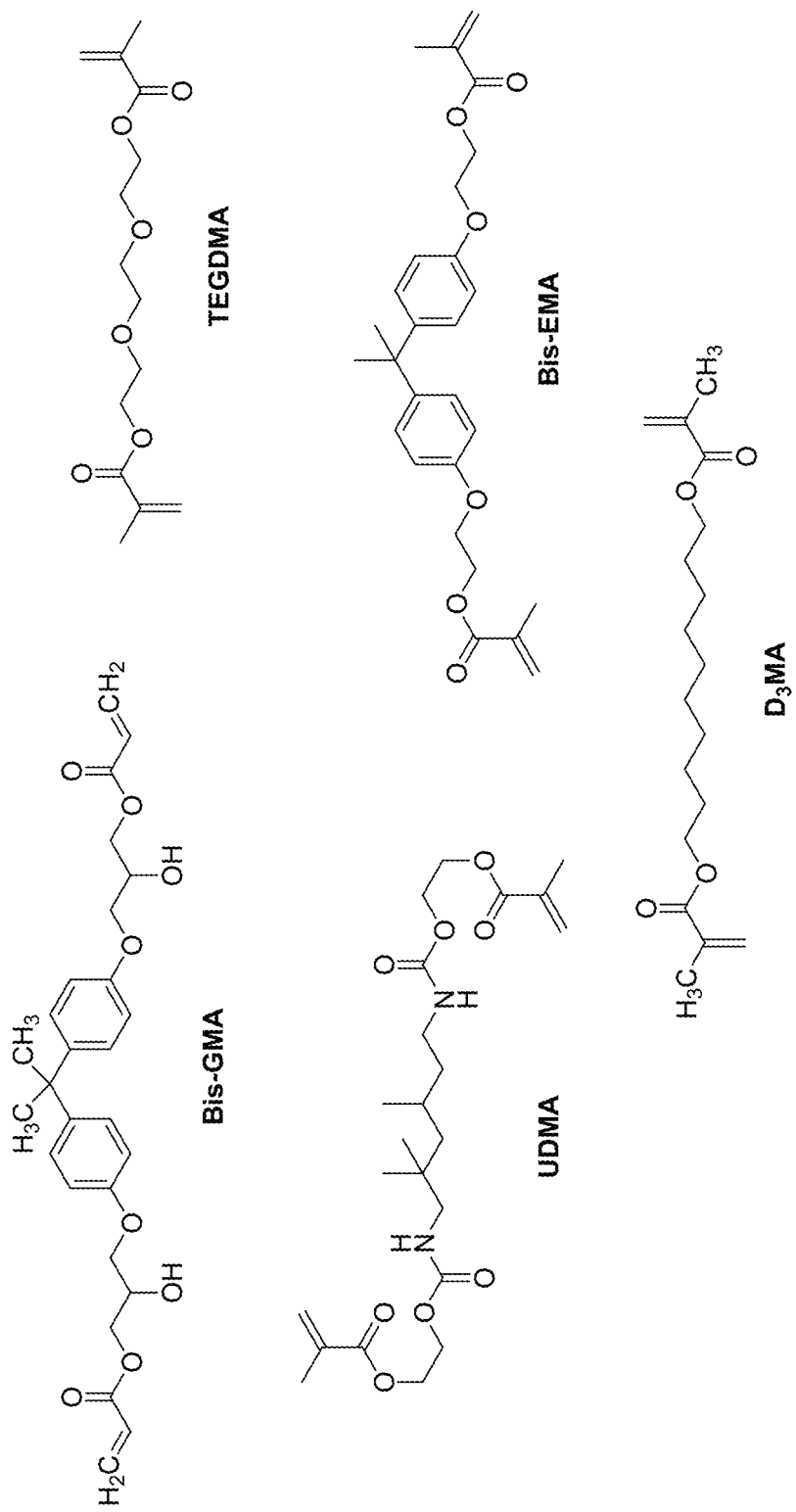
FIG. 1 shows structures of most used commercial dental monomers in dental composites.

Embodiments of the present disclosure will now be described more fully hereinafter with reference to the accompanying drawings, in which some, but not all embodiments of the disclosure are shown.

Unless otherwise specified, "a," "an," "at least one," and "one or more" are used interchangeably.

Within the description of this disclosure, where a numerical limit or range is stated, the endpoints are included unless stated otherwise. Also, all values and subranges within a numerical limit or range are specifically included as if explicitly written out.

As used herein, the term "compound" refers to a chemical entity, whether in a solid, liquid or gaseous phase, and whether in a crude mixture or purified and isolated.

As used herein, a "composite" refers to a combination of two or more distinct constituent materials into one. The individual components, on an atomic level, remain separate and distinct within the finished structure. The materials may have different physical or chemical properties, that when combined, produce a material with characteristics different from the individual components. In material science, a composite occurs if two or different substances are combined together to produce a new substance (Ferracane, J., "Current trends in dental composites", Critical Reviews in Oral Biology & Medicine, vol. 6, pp. 302-318, 1995, incorporated herein by reference in its entirety). Composites contain two or more chemically distinct constituents with a dissimilar interface separating them. As such, the resulting material would ideally have physical properties better than any of its constituents. A "resin composite" generally refers to a resin-based composite containing a mixture of a polymerizable resin and a reinforcing filler. A dental composite is a resin composite used in dental prosthesis as a restorative material or an adhesive. Because of their aesthetic appeal, mechanical strength and low cost, dental composites are often considered superior to metal alloys and dental ceramics (Ruddell, D., Maloney, M., and Thompson, J., "Effect of novel filler particles on the mechanical and wear properties of dental composites", Dental Materials, vol. 18, pp. 72-80, 2002). Dental composites are formable, sparingly soluble, electrical and thermal insulating, opaque or translucent, moderate in stiffness and hardness, and can be machine-manufactured. Composites have characteristics which is in-between that of the two material constituents. The benefits of combining two material gives the opportunity of fabricating a new material with better desirable handling properties that cannot be achieved using one material alone. For instance, the addition of polymer to non-condensable and non-packable ceramic allows easy binding between separate ceramics and can be used as a paste. The volume fraction and properties of both segments of organic matrix and fillers is important. Composite are mainly categorized according to the shape or nature of the filler phase, for example, fiber reinforced or particle reinforced.

Issues with earlier dental composites including poor wear resistance, high volumetric shrinkage during polymerization lead to marginal leakage, secondary dental caries, and discoloration (Rueggeberg, F. A., "From vulcanite to vinyl, a history of resins in restorative dentistry", The Journal of prosthetic dentistry, vol. 87, pp. 364-379, 2002). In early 1950's, inorganic particles were added to dental composites to overcome polymerization contraction, water sorption, and thermal expansion (Patel, M., and Braden, M., "Cross-linking and ring opening during polymerization of heterocyclic methacrylates and acrylates", Biomaterials, vol. 10, pp. 277-280, 1989; and Patel, M., Braden, M., and Davy, K., "Polymerization shrinkage of methacrylate esters", Biomaterials, vol. 8, pp. 53-56, 1987). These composite materials still show a high level of wear, discoloration, and unsatisfactory mechanical properties despite some improvement in polymerization shrinkage (Bowen, R. L., and Marjenhoff, W. A., "Dental composites/glass ionomers: the materials", Advances in dental research, vol. 6, pp. 44-49, 1992). Due to their unique properties such as ease of preparation, aesthetic appeal, mechanical strength, and biological compatibility, resin composites were developed for dental restoration in mid 1960s (Karbhari, V. M., and Strassler, H., "Effect of fiber architecture on flexural characteristics and fracture of fiber-reinforced dental composites", Dental Materials, vol. 23, pp. 960-968, 2007; and Xia, Y., Zhang, F., Xie, H., and Gu, N., "Nanoparticle-reinforced resin-based dental composites", Journal of dentistry, vol. 36, pp. 450-455, 2008). They are generally used as a substitute to conventional dental amalgam alloys, which have undesirable color, toxicity, and corrosion. Resin composites continue to gain popularity because of a rising concern that amalgam adversely effects human health and the environment.

In early 1960s, Bowen invented bisphenol A-glycidyl methacrylate (bis-GMA), which revolutionized dentistry as it set a foundation for dental composites used today. Dental composites contain three major components: an organic matrix formed by a fluid monomer, inorganic filler, and coupling agent (Table 6) (Kahler, B., Kotousov, A., and Swain, M. V., "On the design of dental resin-based composites: a micromechanical approach", Acta biomaterialia, vol. 4, pp. 165-172, 2008). Some dental composites can be prepared by mixing an accelerator/co-initiator (e.g. a tertiary amine) and an initiator (e.g. benzoyl peroxide) immediately before use. Ultraviolet (UV) light-activated resin composites are initiated using light of an average wavelength at around 365 nm. The disadvantages of UV-activated resin composites include eye damage, soft tissue burns, and limited curing depth (Dart, E. C., and Nemcek, J. Photopolymerizable composition, Patent GB 1,408,265, JP 54-10986, 1978). Later, using blue light to cure a visible light activated resin composite was reported (Chen, M.-H., "Update on dental nanocomposites", Journal of Dental Research, vol. 89, pp. 549-560, 2010).

TABLE 6

Composition of resin dental materials

| | | |
|---|---|---|
| Principal monomer | Bis-GMA | A primary monomer |
| | Bis-EMA | Forms polymer matrix |
| | UDMA | Principal monomer |
| Diluent monomer | TEGDMA | Reduce the viscosity of the principal monomer |
| | UDMA | |

TABLE 6-continued

Composition of resin dental materials

| Inorganic fillers | Glass | Provides strength |
| --- | --- | --- |
| | Ceramic | Improves the optical properties |
| Silane coupling agent | γ-methacryloxypropyl trimethoxysilane | Bonds the filler to resin |
| Photoinitiators | Camphoquinone | Initiates polymerization reaction |
| Other chemicals for curing | Tertiary amine | Accelerate polymerization reaction |
| UV stabilizers | 2-hydroxy-4-methoxybenzophenone | Prevents changes in shade |
| Inhibitors | Monomethyl ether of hydrouinone | Prevents self-polymerization |
| Radiopacifiers | Strontium, barium and lithium | Permit the material to be seen |

According to a first aspect, the present disclosure relates to a resin composite comprising (i) a polymerizable monomer, (ii) a polymerization initiator system, and (iii) azole-functionalized silica nanoparticles in an amount ranging from 5 wt % to 75 wt % relative to a total weight of the resin composite, wherein the azole-functionalized silica nanoparticles are a ring-opening reaction product of silica nanoparticles modified with epoxide groups and an azole moiety.

As used herein, the term "substituted" refers to at least one hydrogen atom that is replaced with a non-hydrogen group, provided that normal valencies are maintained and that the substitution results in a stable compound. When a substituent is noted as "optionally substituted", the substituents are selected from the exemplary group including, but not limited to, halo, hydroxyl, alkoxy, oxo, alkanoyl, aryloxy, alkanoyloxy, amino, alkylamino, arylamino, arylalkylamino, disubstituted amines (e.g. in which the two amino substituents are selected from the exemplary group including, but not limited to, alkyl, aryl or arylalkyl), alkanylamino, aroylamino, aralkanoylamino, substituted alkanoylamino, substituted arylamino, aubstituted aralkanoylamino, thiol, alkylthio, arylthio, arylalkylthio, alkylthiono, arylthiono, aryalkylthiono, alkylsulfonyl, arylsulfonyl, arylalkylsulfonyl, sulfonamide (e.g. —SO$_2$NH$_2$), substituted sulfonamide, nitro, cyano, carboxy, carbamyl (e.g. —CONH$_2$), substituted carbamyl (e.g. —CONHalkyl, —CONHaryl, —CONHarylalkyl or cases where there are two substituents on one nitrogen from alkyl, aryl, or alkylalkyl), alkoxycarbonyl, aryl, substituted aryl, guanidine, heterocyclyl (e.g. indolyl, imidazoyl, furyl, thienyl, thiazolyl, pyrrolidyl, pyridyl, pyrimidiyl, pyrrolidinyl, piperidinyl, morpholinyl, piperazinyl, homopiperazinyl and the like), substituted heterocyclyl and mixtures thereof and the like.

As used herein, the term "alkyl" unless otherwise specified refers to both branched and straight chain saturated aliphatic primary, secondary, and/or tertiary hydrocarbons of typically C$_1$ to C$_{12}$, preferably C$_2$ to C$_8$, and specifically includes, but is not limited to, methyl, trifluoromethyl, ethyl, n-propyl, isopropyl, n-butyl, sec-butyl, isobutyl, t-butyl, pentyl, isopentyl, neopentyl, hexyl, isohexyl, 3-methylpentyl, 2,2-dimethylbutyl, and 2,3-dimethylbutyl.

In one or more embodiments, the silica nanoparticle modified with epoxide groups is represented by formula (I)

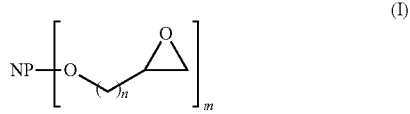

(I)

wherein NP represents a silica nanoparticle, n is a positive integer in a range of 1-6, 2-5, or 3-4, and m is a positive integer in a range of 2-1000, 3-900, 4-800, 5-700, 6-600, 7-500, 8-400, 9-300, 10-200, 12-180, 14-160, 16-140, 18-120, 20-100, 30-90, 40-80, or 50-70.

An average diameter (e.g., average particle diameter) of the nanoparticle of the present disclosure in any of its embodiments refers to the average linear distance measured from one point on the nanoparticle through the center of the nanoparticle to a point directly across from it. In one embodiment, the silica nanoparticles used herein to prepare the silica nanoparticles with an epoxide compound may have an average diameter in a range of 2-100 nim, 5-90 nm, 10-80 nim, 15-70 nm, 20-60 nm, or 30-50 nim. In some embodiments, the silica nanoparticle may be commercially available from a variety of sources (e.g. Sigma Aldrich, Alfa Aesar, Gelest, Strem Chemicals) or prepared in-house according to published methods known to one of ordinary skill in the art. For example, the silica nanoparticles may be synthesized by hydrolyzing a silicon precursor, e.g. a tetraalkoxysilane such as tetraethyl orthosilicate (TEOS), tetramethyl orthosilicate, tetrapropyl orthosilicate, tetrabutyl orthosilicate, tetraisopropyl orthosilicate, or a silicon salt such as sodium silicate in a solvent mixture, e.g. a mixture of water and an alcohol, e.g. methanol, ethanol, propanol, butanol, isopropanol, at a volumn ratio of 4:1 to 1:4, 3:1 to 1:3, 2:1 to 1:2, or about 1:1. In some embodiments, the silicon precursor is a trialkoxysilane, e.g. (3-mercaptopropyl)trimethoxysilane (MPTMS), trimethoxymethylsilane, triethoxyvinylsilane, allyltriethoxysilane, (3-glycidyloxypropyl)trimethoxysi lane. In a preferred embodiment, hydrolyzing the silicon precursor is catalyzed by a base such as ammonium hydroxide and sodium hydroxide, or an acid such as hydrochloric acid and sulfuric acid. In a preferred embodiment, the reaction is performed under agitation. Methods of agitation include, without limitation, using an agitator, a vortexer, a rotary shaker, a magnetic stirrer, a centrifugal mixer, or an overhead stirrer. In a preferred embodiment, the reaction is agitated by sonication in an ultrasonic bath or with an ultrasonic probe. In another embodiment, the reaction is agitated using a magnetic stirrer with a rotational speed of at least 250 rpm, preferably at least 500 rpm, more preferably at least 800 rpm. In a preferred embodiment, the silica nanoparticles are collected as a solid that may be separated (filtered off), and then dried. In one embodiment, the solid may be dried at 40-150° C., preferably 50-120° C., or about 80° C. In a preferred embodiment, the reaction has a product yield of at least 50%, preferably at least 60%/c, preferably at least 65%, preferably at least 70%, preferably at least 75%, preferably at least 80%. The product yield is calculated as (mass of product/mass of total reactants)×100%.

In one embodiment, the silica nanoparticle modified with epoxide groups of formula (I) may be prepared by reacting the aforementioned silica nanoparticles with an epoxide compound of formula (II)

(II)

wherein X is a halogen group including chloro, bromo and iodo. Preferably X is chloro. In some embodiments, the length of —CH$_2$— represented by n is 1, 2, 3, 4, 5, or 6. In another embodiment, n is a positive integer greater than 6. In a preferred embodiment, n is 1. In a preferred embodiment, the epoxide compound of formula (II) is epichlorohydrin or epibromohydrin. In another embodiment, the epoxide compound employed to prepare the silica nanoparticle modified with epoxide groups is not epichlorohydrin or epibromohydrin. For example, 2-(1,2-dichloroethyl)oxirane having a branched alkyl chain may be used as the epoxide compound. In a preferred embodiment, reacting the silica nanoparticles with the epoxide compound to form the silica nanoparticle modified with epoxide groups is performed in a polar aprotic solvent, preferably in tetrahydrofuran (THF). Exemplary polar aprotic solvents that may be used in addition to, or in lieu of THF include, but are not limited to, dimethylformamide, ethyl acetate, acetone, acetonitrile, dimethyl sulfoxide, nitromethane, propylene carbonate, and mixtures thereof. It is equally envisaged that the reaction may be adapted to be performed in a non-polar solvent such as pentane, cyclopentane, hexane, cyclohexane, benzene, toluene, 1,4-dioxane, diethyl ether, and dichloromethane. In a preferred embodiment, the reaction is performed at a concentration of the silica nanoparticles in the range of 1-1000 g/L, preferably 10-750 g/L, preferably 50-500 g/L, preferably 75-250 g/L, preferably 90-120 g/L. In a preferred embodiment, the reaction is performed at a concentration of the epoxide compound in the range of 0.1-100 M, preferably 0.5-50 M, preferably 1-25 M, preferably 5-20 M, preferably 8-12 M. In a preferred embodiment, the reaction is performed under mechanical stirring, preferably a magnetic stirrer at a temperature of up to 80° C., preferably 20-70° C., preferably 30-65° C., preferably 40-60° C., or about 50° C. In a preferred embodiment, the silica nanoparticle modified with epoxide groups are collected as a solid that may be separated (filtered off), washed by a mixture of ethanol and water at a ratio in the range of 1:10 to 1:1, 1:8 to 1:2, 1:6 to 1:3, or about 1:4, and then filtered and dried. In one embodiment, the solid may be dried at 40-150° C., preferably 50-120° C., or about 80° C. In a preferred embodiment, the reaction has a product yield of at least 50%, preferably at least 60%, preferably at least 65%, preferably at least 70%, preferably at least 75%, preferably at least 80%. The product yield is calculated as (mass of product/total mass of reactants)×100%. In one embodiment, the formed silica nanoparticle modified with epoxide groups may have an average diameter in a range of 5-120 nm, 10-110 nm, 20-100 nm, 30-90 nm, 40-80 nm, or 50-70 nm.

Due to a considerable ring strain, epoxides are electrophiles that can undergo ring-opening reactions (ROR) upon attacks by nucleophiles such as alkoxides, thiols, Grignard reagents, and nitrogen nucleophiles e.g. amines, azides, and azoles. The azole-functionalized silica nanoparticles described herein are a ring-opening reaction product of the silica nanoparticles modified with epoxide groups and an azole moiety. In a preferred embodiment, reacting the silica nanoparticles modified with epoxide groups with the azole compound to form the azole-functionalized silica nanoparticles is performed in a polar aprotic solvent, preferably in dimethylformamide (DMF). Exemplary polar aprotic solvents that may be used in addition to, or in lieu of DMF include, but are not limited to, tetrahydrofuran, ethyl acetate, acetone, acetonitrile, dimethyl sulfoxide, nitromethane, propylene carbonate, and mixtures thereof. In a preferred embodiment, the reaction is performed at a concentration of the azole compound in the range of 0.1-10 M, preferably 0.5-5 M, preferably 1-4 M, preferably 2-3 M under an inert gas such as $N_2$, Ar, He. For example, the inert gas may be bubbled in the reaction mixture in a sealed container for at least 0.5 hour, 1 hour, or at least 2 hours before and during the reaction. In a preferred embodiment, the reaction is performed under mechanical stirring, preferably a magnetic stirrer at a temperature of up to 120° C., preferably 30-110° C., preferably 40-100° C., preferably 60-90° C., preferably 70-85° C., or about 80° C. and has a reaction time of up to 48 hours, preferably 2-44 hours, preferably 8-38 hours, preferably 12-32 hours, preferably 18-30 hours, or about 24 hours. In a preferred embodiment, the azole-functionalized silica nanoparticles are collected as a solid that may be separated (filtered off), washed by a mixture of ethanol and water at a ratio in the range of 1:10 to 1:1, 1:8 to 1:2, 1:6 to 1:3, or about 1:4, and then filtered and dried. In one embodiment, the solid may be dried at 20-120° C., preferably 40-100° C., or about 80° C. until a constant weight is achieved. In a preferred embodiment, the reaction has a product yield of at least 50%, preferably at least 60%, preferably at least 65%, preferably at least 70%, preferably at least 75%, preferably at least 80%. The product yield is calculated as (mass of product/total mass of reactants)×100%. In one embodiment, the formed azole-functionalized silica nanoparticles may have an average diameter in a range of 5-150 nm, 10-140 nm, 20-130 nm, 30-120 nm, 40-110 nm, 50-100 nm, 60-90 nm, or 70-80 nm.

Exemplary azole compounds useful for the current disclosure include, but are not limited to, imidazole, pyrazole, 1H-1,2,3-triazole, 1H-1,2,4-triazole, tetrazole, pentazole, oxazole, isoxazole, 1,2,4-oxadiazole, 1,2,5-oxadiazole, 1,3,4-oxadiazole, thiazole, isothiazole, thiadiazole, 1,2,4-thiadiazole, 1,2,5-thiadiazole, and 1,3,4-thiadiazole. In a preferred embodiment, the azole moiety is at least one selected from the group consisting of 1H-1,2,4-triazole, 3-amino-1,2,4-triazole, 5-aminotetrazole, and imidazole.

In one embodiment, the formed azole-functionalized silica nanoparticle is represented by a formula selected from the group consisting of

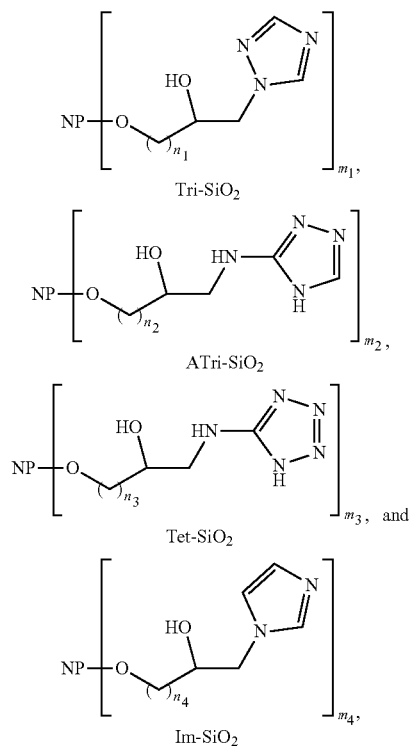

wherein NP represents a silica nanoparticle described herein in any of its embodiments, $n_1$, $n_2$, $n_3$ and $n_4$ are independently a positive integer in a range of 1-6, 2-5, or 3-4, and $m_1$, $m_2$, $m_3$ and $m_4$ are independently a positive integer in a range of 2-1000. In a preferred embodiment, $n_1$, $n_2$, $n_3$ and $n_4$ are 1. In certain embodiments, $n$, $n_2$, $n_3$ and $n_4$ are independently a positive integer in a range of 2-5, or 3-4. In certain embodiments, $m_1$, $m_2$, $m_3$ and $m_4$ are independently a positive integer in a range of 3-900, 4-800, 5-700, 6-600, 7-500, 8-400, 9-300, 10-200, 12-180, 14-160, 16-140, 18-120, 20-100, 30-90, 40-80, or 50-70.

The formed azole-functionalized silica nanoparticles may be in the same shape or different shapes, and may be the same size or different sizes. The nanoparticles may be spherical, ellipsoidal, oblong, ovoidal, or some other rounded shape. In an alternative embodiment, the nanoparticles may be angular, rectangular, prismoidal, or some other angular shape, or they may be nanorods, nanowires, or nanosprings. In one or more embodiments, the azole-functionalized silica nanoparticles may have an average diameter in a range of 2-500 nm, 4-400 nm, 6-300 nm, 8-200 nm, 10-150 nm, 20-100 nm, 30-90 nm, 40-80 nm, or 50-70 nm. In some embodiments, the nanoparticles may have a narrow size distribution, comprising nanoparticles with diameters within 75-125% of the average particle diameter, 80-120%, 85-115%, 90-110%, or preferably within 95-105% of the average particle diameter. In one embodiment, the azole-functionalized silica nanoparticles may comprise nanoparticles clustered together as agglomerates having an average diameter in a range of 10-500 nm, 50-300 nm, or 100-200 nm. As used herein, the term "agglomerates" refers to a clustered particulate composition comprising primary particles, the primary particles being aggregated together in such a way so as to form clusters thereof, with at least 50 volume percent of the clusters having a mean diameter that is at least 2 times the mean diameter of the primary particles, and preferably at least 90 volume percent of the clusters having a mean diameter that is at least 5 times the mean diameter of the primary particles. In a preferred embodiment, the nanoparticles are well separated from one another and do not form agglomerates. The size and shape of particles may be analyzed by techniques such as dynamic light scattering (DLS), scanning electron microscopy (SEM) and/or atomic force microscopy (AFM).

In one or more embodiments, silica ($SiO_2$) is present in an amount of 20-50 wt % relative to a total weight of the azole-functionalized silica nanoparticle, preferably 22-45 wt %, preferably 25-40 wt %, preferably 28-35 wt %, preferably 30-32 wt % relative to a total weight of the azole-functionalized silica nanoparticle. In one or more embodiments, the azole moiety is present in an amount of 40-80 wt % relative to a total weight of the azole-functionalized silica nanoparticle, preferably 42-75 wt %, preferably 45-70 wt %, preferably 50-65 wt %, preferably 55-60 wt % relative to a total weight of the azole-functionalized silica nanoparticle. The composition of the azole-functionalized silica nanoparticle including the weight percentages of silicon and azole moiety may be determined by elemental analysis techniques such as energy-dispersive X-ray spectroscopy (EDX), X-ray photoelectron spectroscopy (XPS), inductively coupled plasma mass spectrometry (ICP-MS), neutron activation analysis, and thermos-gravimetric analysis (TGA).

In one or more embodiments, the azole-functionalized silica nanoparticles are present as a filler in an amount of about 5 wt % to about 75 wt %, about 10 wt % to about 72 wt %, about 25 wt % to about 70 wt %, about 40 wt % to about 65 wt %, or about 50 wt % to about 60 wt % relative to the total weight of the resin composite. In certain embodiments, the azole-functionalized silica nanoparticles are present in an amount of about 50 wt %, 51 wt %, 52 wt %, 53 wt %, 54 wt %, 55 wt %, 56 wt %, 57 wt %, 58 wt %, 59 wt %, 60 wt %, 61 wt %, 62 wt %, 63 wt %, 64 wt %, 65 wt %, 66 wt %, 67 wt %, 68 wt %, 69 wt %, 70 wt %, 71 wt %, 72 wt %, 73 wt %, 74 wt %, or 75 wt % relative to the total weight of the resin composite.

Since Bowen's first attempt (Gonçalves, F., Azevedo, C. L., Ferracane, J. L., and Braga, R. R., "BisGMA/TEGDMA ratio and filler content effects on shrinkage stress", Dental materials, vol. 27, pp. 520-526, 2011; and Ilie, N., and Hickel, R., "Resin composite restorative materials", Australian dental journal, vol. 56, pp. 59-66, 2011, each incorporated herein by reference in their entirety), filler component of the dental composite has been developed significantly. In 1970s, micro-filled composites containing amorphous silica with a mean particle size of 0.05 µm were established. In order to produce aesthetic composites with a smooth surface, smaller-sized particles were used allowing composites to be polished without preferential abrasion. Micro-fine silica is also softer than quartz. However, like quartz, these fillers are not radiopaque. Radiopaque particles such as strontium and barium silicate, lithium and aluminum silicate, and ytterbium triflouride were later incorporated. Despite being more aesthetically pleasing, these micro-filled composites have a tendency to fracture under stress concentration (Ferracane, J. L., "Resin composite-state of the art", Dental materials, vol. 27, pp. 29-38, 2011, incorporated herein by reference in its entirety).

Fillers, when blended with the aforementioned polymerizable monomer, provide dental composites with greater mechanical strength and preferably with improved translucency. Currently used fillers in dental resin composites include quartz, and silica glass containing zirconium, barium, colloidal silica, and strontium. Many studies were conducted to probe the relationship between filler and diametral tensile strength, hardness, flexural strength, compressive strength, wear, shrinkage stress, fracture toughness, thermal expansion and shear punch strength of a resin composite (Lu, H., Lee, Y., Oguri, M., and Powers, J., "Properties of a dental resin composite with a spherical inorganic filler", Operative Dentistry, vol. 31, pp. 734-740, 2006; Turssi, C., Ferracane, J., and Vogel, K., "Filler features and their effects on wear and degree of conversion of particulate dental resin composites", Biomaterials, vol. 26, pp. 4932-4937, 2005). Addition of filler not only increases the elastic modulus and strength of final restorative product, but also reduces polymerization contraction, coefficient of thermal expansion, and liquid uptake. The physical and mechanical properties of a composite resin are affected by the size, content, morphology, and distribution of its fillers. As a result of recent progress in nanotechnology, nano-filled and nano-hybrid materials have been introduced in order to reduce the size of fillers and enhance the physical, mechanical and clinical performances of dental composites.

In one or more embodiments, the presently disclosed resin composite further comprises a filler which is at least one selected from the group consisting of a glass filler, a ceramic filler, and a polymer-based filler, in addition to the azole-functionalized silica nanoparticles. Useful glass fillers include, but are not limited to, glasses that contain small amounts of heavy metals (barium, strontium, aluminum, etc) including barium borosilicate glass, aluminosilicate glass, boroaluminosilicate, strontium borosilicate glass, strontium-alumino-fluoro-silicate glass, and fluoroaluminosilicate glass, ytterbium trifluoride filler, and fiber glass filler. Exemplary ceramic fillers include, without limitation, zirconia filler, zirconia-silica filler, quartz filler, and porcelain filler. Polymer-based fillers include polymeric material that is pre-polymerized, e.g. poly(methyl methacrylate), poly(ethyl methacrylate), poly(acrylic acid), poly(methacrylic acid), poly(vinyl acetate), polyethylene, and polytetrafluoroethylene, and then ground into filler particles, and polymer fibers. In a preferred embodiment, the filler is at least one selected from the group consisting of zirconia, and aluminosilicate.

Fillers that are commonly incorporated in a dental composite can be categorized into three major classes based on their average particle size, including macrofillers with an average particle size of 1-100 μm, microfillers with an average particle size of 0.01-0.1 μm, and nanofillers with an average particle size of 0.005-0.01 μm. In some embodiments, a mixture of the additional filler and the azole-functionalized silica nanoparticles at an approximate weight ratio of 1:1 to 10:1, 2:1 to 8:1, or 4:1 to 6:1 is used as a mixed filler for the resin composite described herein. The particle size of the additional filler may be dependent on the identity of that filler. For example, in one embodiment where barium boroaluminosilicate glass particles are present as the filler, the medium particle diameter of the filler may range from about 0.1 to about 50 μm, from about 0.25 to about 25 μm, from about 0.5 to about 15 μm, or about 1.0 to about 7.5 μm. In another embodiment, where zirconia particles are served as the filler, the medium particle diameter of the filler may range from about 10 to about 500 nm, from about 20 to 400 nm, from about 30 to about 300 nm, from about 40 to about 200 nm, from about 50 to about 100 nm, or from about 60 to about 80 nm. In a preferred embodiment, a mixture of a micro-filler and the azole-functionalized silica nanoparticles at an approximate weight ratio of 1:1 to 10:1, 2:1 to 8:1, or 4:1 to 6:1 is used as the mixed filler. In one or more embodiments, the mixed filler is present in an amount of about 5 wt % to about 75 wt %, about 10 wt % to about 72 wt %, about 25 wt % to about 70 wt %, about 40 wt % to about 65 wt %, or about 50 wt % to about 60 wt % relative to the total weight of the resin composite. In certain embodiments, the mixed filler is present in an amount of about 50 wt %, 51 wt %, 52 wt %, 53 wt %, 54 wt %, 55 wt %, 56 wt %, 57 wt %, 58 wt %, 59 wt %, 60 wt %, 61 wt %, 62 wt %, 63 wt %, 64 wt %, 65 wt %, 66 wt %, 67 wt %, 68 wt %, 69 wt %, 70 wt %, 71 wt %, 72 wt %, 73 wt %, 74 wt %, or 75 wt % relative to the total weight of the resin composite.

Figure 2:
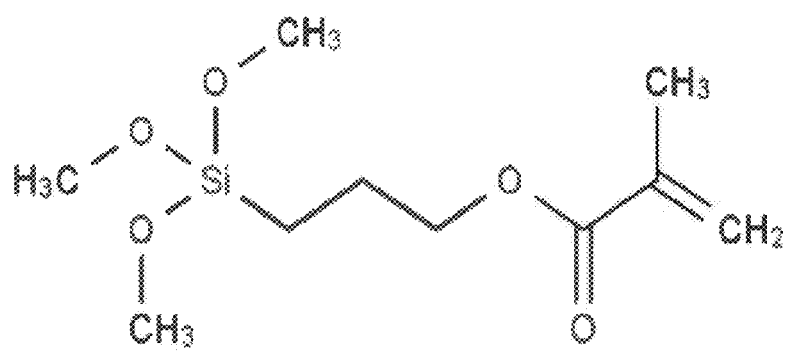
FIG. 2 shows the chemical structure of silane MPTS.

Inorganic fillers and organic matrix are connected together covalently by coupling agents. A strong interaction between the filler segment and organic matrix segment is crucial to achieve desired mechanical and physical properties for clinical use. A silane is used as a coupling agent by binding the filler with organic matrix through hydroxyl and metharcrylate groups. Coupling agents should be able to (1) connect the organic matrix and filler by formation of interfacial bridges, (2) improve the mechanical and physical properties of a composite, (3) reduce clinical wear, (4) distribute stress among bordering fillers and polymer matrix, and (5) create a hydrophobic environment that lowers liquid absorption of a composite (Powers, J. M., and Sakaguchi, R. L. Craig's restorative dental materials, 13/e, Elsevier India, 2006b). Chemical structure of a commonly used bi-functional silane coupling agent, 3-methacryloxypropyltrimethoxysilane (MPTS), is given in FIG. 2.

Depending on the chemical structure, the azole-functionalized silica nanoparticles and the filler used herein, e.g. a glass filler in addition to the azole-functionalized silica nanoparticles may be silanized to achieve better reinforcement by the resin matrix. Suitable means of silanization are generally known to those skilled in the art, and include treating a surface of the filler with a silanization agent. Typical silanization agents suitable for the purpose of the invention include, but are not limited to, silanes bearing a methacrylic functional group such as methacryloxypropyl trimethoxy silane; silanes bearing an epoxy group such as glycidoxy propyl trimethoxy silane or beta-(3,4-epoxycyclohexyl)ethyl trimethoxysilane; silanes comprising an amino functional group such as gamaaminopropyl trimethoxy silane, gama-aminopropyl triethoxy silane or N-beta(aminoethyl)gama-aminopropyl trimethoxy silane); and silanes comprising a mercapto group such as 3-mercaptopropyl trimethoxy silane.

Dimethacrylate monomers (FIG. 1) such as bis-GMA, Bisphenol-A-glycidyl dimethacrylatel dimethacrylate, UDMA, TEGDMA, bis-EMA, $D_3MA$ are generally used as an organic matrix phase. Currently, the most frequently used monomer is bis-GMA. Because of its low volatility and diffusivity into tissue, bis-GMA reduces contraction and toxicity and improves elastic modulus, hardness and strength of a dental restorative. However, high viscosity of bis-GMA due to hydrogen bonding interactions between hydroxyl groups creates difficulties in incorporating inorganic fillers and causes low degrees of conversion (Amirouche-Korichi, A., Mouzali, M., and Watts, D. C., "Effects of monomer ratios and highly radiopaque fillers on degree of conversion and shrinkage-strain of dental resin composites", Dental Materials, vol. 25, pp. 1411-1418, 2009, incorporated herein by reference in its entirety). Monomers such as TEGDMA with a lower viscosity are often used to dilute bis-GMA. Using a mixture of dimethacrylates as the polymer matrix can be beneficial as it may help meet physical-chemical requirements of dental resin monomers (Shalaby, S. W., and Salz, U. Polymers for dental and orthopedic applications, CRC Press, 2006, incorporated herein by reference in its entirely) such as (1) fast rate of photopolymerization and degree of cross-linking, (2) a Tg above 60° C., (3) a limited uptake of water, (4) optimal mechanical properties and wear resistance, (5) low polymerization contraction or extension, (6) stability during storage and after being placed in an oral environment, and (7) low toxicity.

Dimethacrylate monomers experience shrinkage upon polymerization. Polymerization contraction causes marginal gaps between composite restoratives and the tooth structure, which in turn weakens the attachment of composite to the surface of the tooth. A monomer of high molecular weight is usually viscous (Table 8) and demonstrates limited polymerization contraction (Table 7). The degree of contraction of composite during polymerization is also affected by the amount of filler. As a result, a mixture of viscous and diluting monomers and different types of fillers are often employed when formulating resin composites for dental applications. (Moszner, N., and Klapdohr, S., "Nanotechnology for dental composites", International Journal of Nanotechnology, vol. 1, pp. 130-156, 2004, incorporated herein by reference in its entirety). Cyclic monomers, hyper-branched or dendritic methacrylates, and fluoride-releasing monomer systems have been developed recently in order to reduce polymerization contraction. (Peutzfeldt, A., "Resin composites in dentistry: the monomer systems", European journal of oral sciences, vol. 105, pp. 97-116, 1997, incorporated herein by reference in its entirety).

TABLE 7

Polymerization contraction ($\Delta V_p$) of dental monomers

| Monomer | $\rho_{mon}$ (g/cm$^3$) | $\rho_{poly}$ (g/cm$^3$) | $\Delta V_p$ (%) |
|---|---|---|---|
| TEGMA | 1.072 | 1.250 | 14.3 |
| TCDMA | — | — | 7.1 |
| Bis-GMA | 1.151 | 1.226 | 6.1 |
| UDMA | 1.110 | 1.190 | 6.7 |

$\rho_{poly}$ polymer density:
$\rho_{mon}$ = monomer density

TABLE 8

Relationship between viscosity and molecular weight of monomer

| Monomer | Viscosity (MPa) | Molecular weight (g/mol) |
|---|---|---|
| TEGMA | 100 | 286 |
| UDMA | 110 | 470 |
| TCDMA | 5.000-10.000 | 332 |
| Bis-GMA | 500.000-800.000 | 512 |

In one or more embodiments, the polymerizable monomer is at least one selected from the group consisting of a methacrylate monomer, an acrylate monomer, an epoxy monomer, and a vinyl monomer.

As used herein, monomers are molecules which can undergo polymerization, thereby contributing constitutional repeating units to the structures of a macromolecule, a polymer, or a resin. Compounds having one or more polymerizable groups and alkoxylated groups (ethylene oxide, polyethylene oxide, etc.) are to be viewed as an extension of a monomer unit and are still considered monomers in the present disclosure unless specified otherwise. The process by which monomers combine end to end to form a polymer is referred to herein as "polymerization". As used herein a "copolymer" refers to a polymer derived from more than one species of monomer and are obtained by "copolymerization" of more than one species of monomer. Copolymers obtained by copolymerization of two monomer and/or oligomer species may be termed bipolymers, those obtained from three monomers may be termed terpolymers and those obtained from four monomers may be termed quarterpolymers, etc. As used herein, "crosslinking", "cross-linking", "cross-linked", "cross-linked", a "crosslink", or a "cross-link" refers to polymers and resins containing branches that connect polymer chains via bonds that link one polymer chain to another. The crosslink may be an atom, a group of atoms, or a number of branch points connected by bonds, groups of atoms, or polymer chains. In a preferred embodiment, the polymerizable monomers in the current disclosure form crosslinking resins.

Polymerizable monomers used herein may include one or more mono-functional and/or multi-functional monomers. A mono-functional monomer refers to a monomer having one polymerizable group such as acrylate, methacrylate, epoxy, and vinyl present per molecule, while a multi-functional monomer refers to a monomer having two or more polymerizable groups present per molecule. Specifically, mono-functional methacrylate monomers useful in the present invention include, but are not limited to, methacrylic acid, methyl methacrylate (MMA), 2-hydroxyethyl methacrylate (HEMA), isopropyl methacrylate, n-propyl methacrylate, isopropyl methacrylate, n-butyl methacrylate, isobutyl methacrylate, hydroxyethyl methacrylate, hydroxypropyl methacrylate, hydroxybutyl methacrylate, propylene glycol monomethacrylate, isobornyl methacrylate, methoxyethoxyethyl methacrylate, ethoxyethoxyethyl methacrylate, tetrahydrofurfuryl methacrylate, acetoxyethyl methacrylate, phenoxyethylmethacrylate, methacryloyloxyethyl phthalate (MEP), and mixtures thereof. Useful multi-functional methacrylate monomers include, but are not limited to, bisphenol A-glycidyl methacrylate (bis-GMA), urethane dimethacrylate (UDMA), triethylene glycol dimethacrylate (TEGDMA), ethoxylated bisphenol A dimethacrylate (bis-EMA), ethyleneglycol dimethacrylate, diethyleneglycol dimethacrylate, trimethyleneglycol dimethacrylate, glycerol dimethacrylate, trimethyolpropane trimethacrylate, tetraethyleneglycol dimethacrylate, 1,3-propanediol dimethacrylate, 1,4-butanediol dimethacrylate, 1,6-hexanediol dimethacrylate, 1,12-dodecanediol dimethacrylate, polyethyleneglycol dimethacrylate, bismethacryloyloxymethyltricyclo-[5.2.1.]decane (TCDMA), trimethylolpropane trimethacrylate, 1,2,4-butanetriol trimethacrylate, pentaerythritol tetramethacrylate, diurethane dimethacrylate (DUDMA), pymmellitic acid glycerol dimethacrylate (PMGDM), and mixtures thereof.

Non-limiting examples of acrylate monomers include acrylic acid, methyl acrylate, ethyl acrylate, propyl acrylate, butyl acrylate, isobutyl acrylate, tert-butyl acrylate, pentyl acrylate, neopentyl acrylate, hexyl acrylate, cyclohexyl acrylate, heptyl acrylate, cyclohexylmethyl acrylate, octyl acrylate, 2-ethylhexyl acrylate, isooctyl acrylate, decyl acrylate, dodecyl acrylate, tetradecyl acrylate, hexadecyl acrylate, octadecyl acrylate, behenyl acrylate, ethyleneglycol diacrylate, neopentylglycol diacrylate, 1,6-hexanediol ethoxylate diacrylate, 1,3-butanediol diacrylate, 1,6-hexanediol diacrylate, 1,4-butanediol diacrylate, di(ethylene glycol) diacrylate, and mixtures thereof.

Epoxy monomers are compounds containing one or more glycidyl ether group, which include, but are not limited to, 1,2-epoxybutane, 1,2-epoxypentane, 1,2-epoxyhexane, glycidyl isopropyl ether, glycidyl 2,2,3,3-tetrafluoropropyl ether, butyl glycidyl ether, tert-butyl glycidyl ether, furfuryl glycidyl ether, 1,2-epoxyoctane, glycidyl 4-methoxyphenyl ether, 2-ethylhexyl glycidyl ether, (2,3-epoxypropyl)benzene, 1,2-epoxy-3-phenoxypropane, 1,2-epoxydodecane, neopentyl glycol diglycidyl ether, 1,4-cyclohexanedimethanol diglycidyl ether, 1,2,7,8-diepoxyoctane, 1,4-butanediol diglycidyl ether, resorcinol diglycidyl ether, N,N-diglycidyl-4-glycidyloxyaniline, and mixtures thereof.

Exemplary vinyl monomers include, but are not limited to, vinyl acetate, vinyl trifluoroacetate, vinyl propionate, vinyl valerate, vinyl neononanoate, vinyl decanoate, vinyl neodecanoate, vinyl stearate, vinyl benzoate, vinyl cinnamate, vinyl 4-tert-butylbenzoate, styrene, vinylbenzyl chloride, 4-vinylbenzoic acid, 2-(trifluoromethyl)styrene, 3-(trifluoromethyl)styrene, 4-(trifluoromethyl)styrene, 4-vinylanisole, 3-methylstyrene, 4-methylstyrene, 2-fluorostyrene, 3-fluorostyrene, 4-fluorostyrene, 2,6-difluorostyrene, 2,3,4,5,6-pentafluorostyrene, 4-tert-butylstyrene, 2,4,6-trimethylstyrene, 3,4-dimethoxystyrene, 4-acetoxystyrene, divinylbenzene, 1,4-bis(4-vinylphenoxy)butane, 1,3,5-triallyl-1,3,5-triazine-2,4,6(1H,3H,5H)-trione, and mixtures thereof.

In one embodiment, the polymerizable monomer in the present disclosure is one or more methacrylate monomers. In a preferred embodiment, the polymerizable monomer is one or more di-functional methacrylate monomer selected from the group consisting of bisphenol A-glycidyl methacrylate (bis-GMA), ethoxylated bisphenol A dimethacrylate (bis-EMA), urethane dimethacrylate (UDMA), triethylene glycol dimethacrylate (TEGDMA), 1,12-dodecanediol dimethacrylate ($D_3MA$), bismethacryloyloxymethyltricyclo-[5.2.1.]decane (TCDMA), and 2-hydroxyethyl methacrylate (HEMA). In one embodiment, the polymerizable monomer is a combination of bis-GMA and TEGDMA at about 5:1 to about 1:5 mass ratio, about 4:1 to about 1:4 mass ratio, about 3:1 to about 1:3 mass ratio, about 2:1 to about 1:2 mass ratio, about 3:2 to about 2:3 mass ratio, or about 1:1 mass ratio. In another embodiment, the polymerizable monomer is a combination of UDMA and TEGDMA at about 5:1 to about 1:5 mass ratio, about 4:1 to about 1:4 mass ratio, about 3:1 to about 1:3 mass ratio, about 2:1 to about 1:2 mass ratio, about 3:2 to about 2:3 mass ratio, or about 1:1 mass ratio. In another embodiment, the polymerizable monomer is a combination of bis-GMA and D3MA at about 5:1 to about 1:5 mass ratio, about 4:1 to about 1:4 mass ratio, about 3:1 to about 1:3 mass ratio, about 2:1 to about 1:2 mass ratio, about 3:2 to about 2:3 mass ratio, or about 1:1 mass ratio. In at least one embodiment, the polymerizable monomer is a combination of both monofunctional and multi-functional monomers. For example, the polymerizable monomer is a mixture of 2-hydroxyethyl methacrylate (HEMA) and bis-GMA at about 2:1 to about 1:10 mass ratio, about 1:1 to about 1:8 mass ratio, about 1:2 to about 1:6 mass ratio, or at about 1:3 to about 1:5 mass ratio. For another example, the polymerizable monomer is a mixture of tetrahydrofurfuryl methacrylate and bis-GMA at about at about 8:1 to about 1:2 mass ratio, about 6:1 to about 1:1 mass ratio, about 5:1 to about 2:1 mass ratio, or about 4:1 to about 3:1 mass ratio.

In one or more embodiments, the polymerizable monomer described herein in any of its embodiments is present in the resin composite in an amount of about 5 wt % to about 25 wt %, about 7 wt % to about 20 wt %, about 10 wt % to about 18 wt %, or about 12 wt % to about 15 wt % relative to the total weight of the resin composite.

Figure 3:
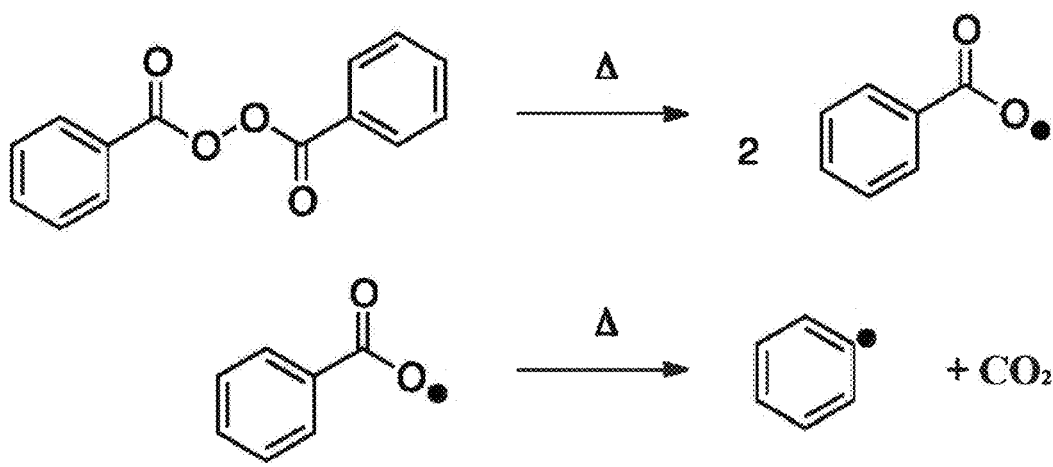
FIG. 3 shows mechanism of thermal decomposition of benzoyl peroxide.
Figure 4:
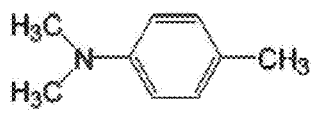
FIG. 4 shows chemical structures of para-substituted derivatives of dimethylaniline used as co-initiators with benzoyl peroxide.
Figure 4:
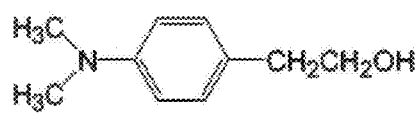
Figure 4:
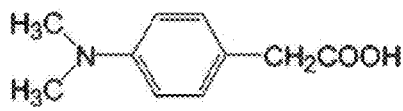
Figure 4:
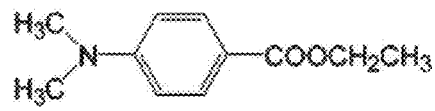
Figure 5:
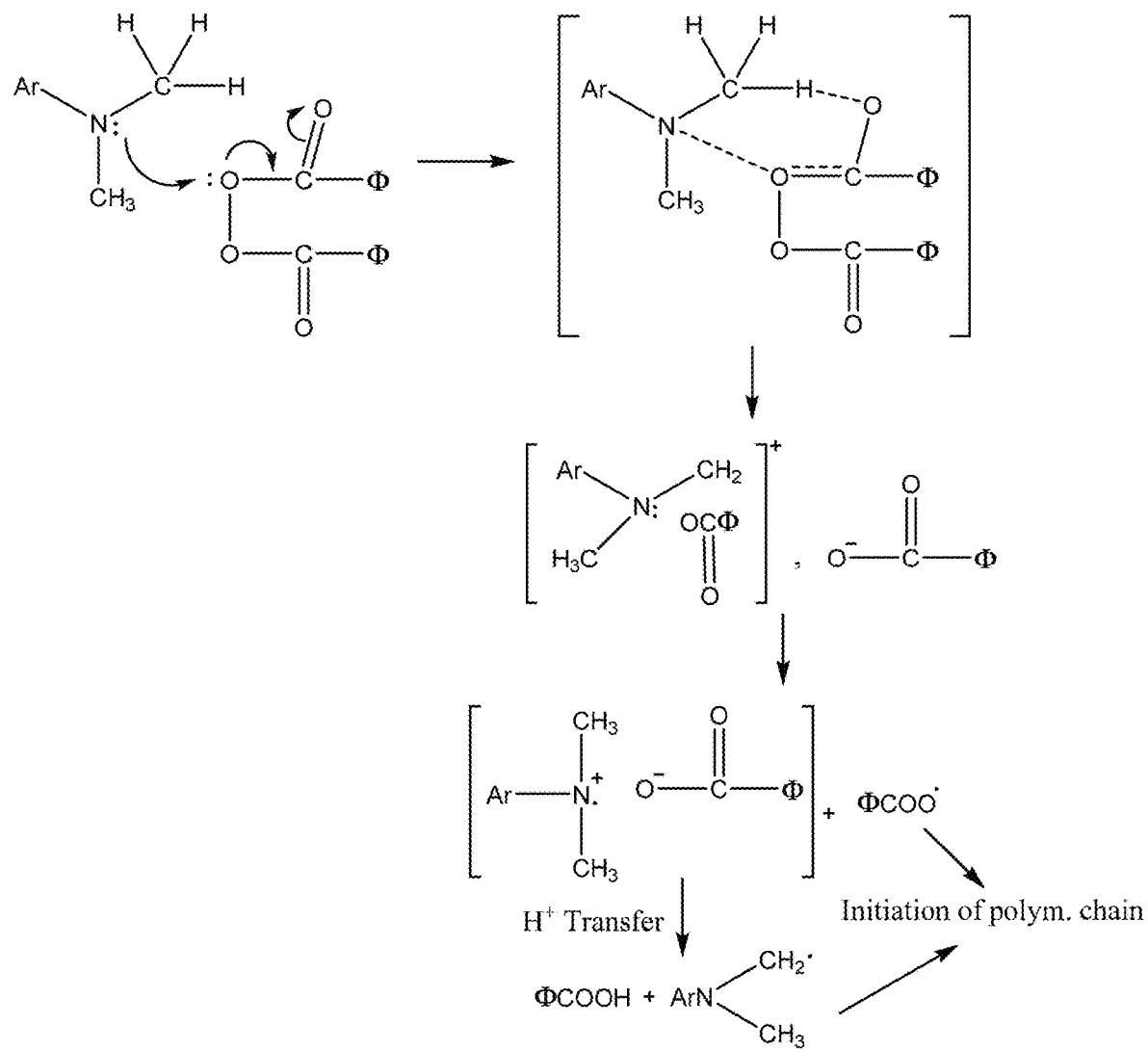
FIG. 5 shows mechanism of redox initiation by benzoyl peroxide/amine system (Vazquez, B., Elvira, C., San Roman, J., and Levenfeld, B., "Reactivity of a polymerizable amine activator in the free radical copolymerization with methyl methacrylate and surface properties of copolymers", Polymer, vol. 38, pp. 4365-4372, 1997, incorporated herein by reference in its entirety).

Polymerization initiators may be advantageously employed in a dental composite. Free-radical polymerization is a method of polymerization by which a polymer is cured by the successive addition of free-radical building blocks. A free radical initiator is capable of generating radical species, which can add on to monomer units and start radical polymerization process. A radical polymerization can be initiated by external energy such as heat, light, and/or electronic current. For chemically-activated resin composites, benzoyl peroxide and tertiary amines are used as sources of free radicals for polymerization initiation. As shown in FIG. 3, thermal decomposition of benzoyl peroxide yields free radicals. Decomposition of a peroxide is achieved by heat, light, or use of chemical compounds. When a peroxide is heated at above 65° C., it thermally decomposes as shown in 2.4. A peroxide can also be activated when brought into contact with a tertiary amine (FIG. 5), such as 4-(N,N-dimethylamino)phenethyl alchohol (DMPOH), 4-(N,N-dimethylamino)phenylacetic acid (DMAPAA), ethyl 4-(dimethylamino)benzoate (EDMAB) and N,N-dimethyl-p-toluidine (DMT) (Achilias, D. S., and Sideridou, I. D., "Kinetics of the benzoyl peroxide/amine initiated free-radical polymerization of dental dimethacrylate monomers: experimental studies and mathematical modeling for TEGDMA and Bis-EMA", Macromolecules, vol. 37, pp. 4254-4265, 2004; Sideridou, I. D., Achilias, D. S., and Karava, O., "Reactivity of benzoyl peroxide/amine system as an initiator for the free radical polymerization of dental and orthopaedic dimethacrylate monomers: effect of the amine and monomer chemical structure", Macromolecules, vol. 39, pp. 2072-2080, 2006; and Sideridou, I. D., Achilias, D. S., and Kostidou, N. C., "Copolymerization kinetics of dental dimethacrylate resins initiated by a benzoyl peroxide/amine redox system", Journal of applied polymer science, vol. 109, pp. 515-524, 2008, each incorporated herein by reference in their entirety).

Figure 6:
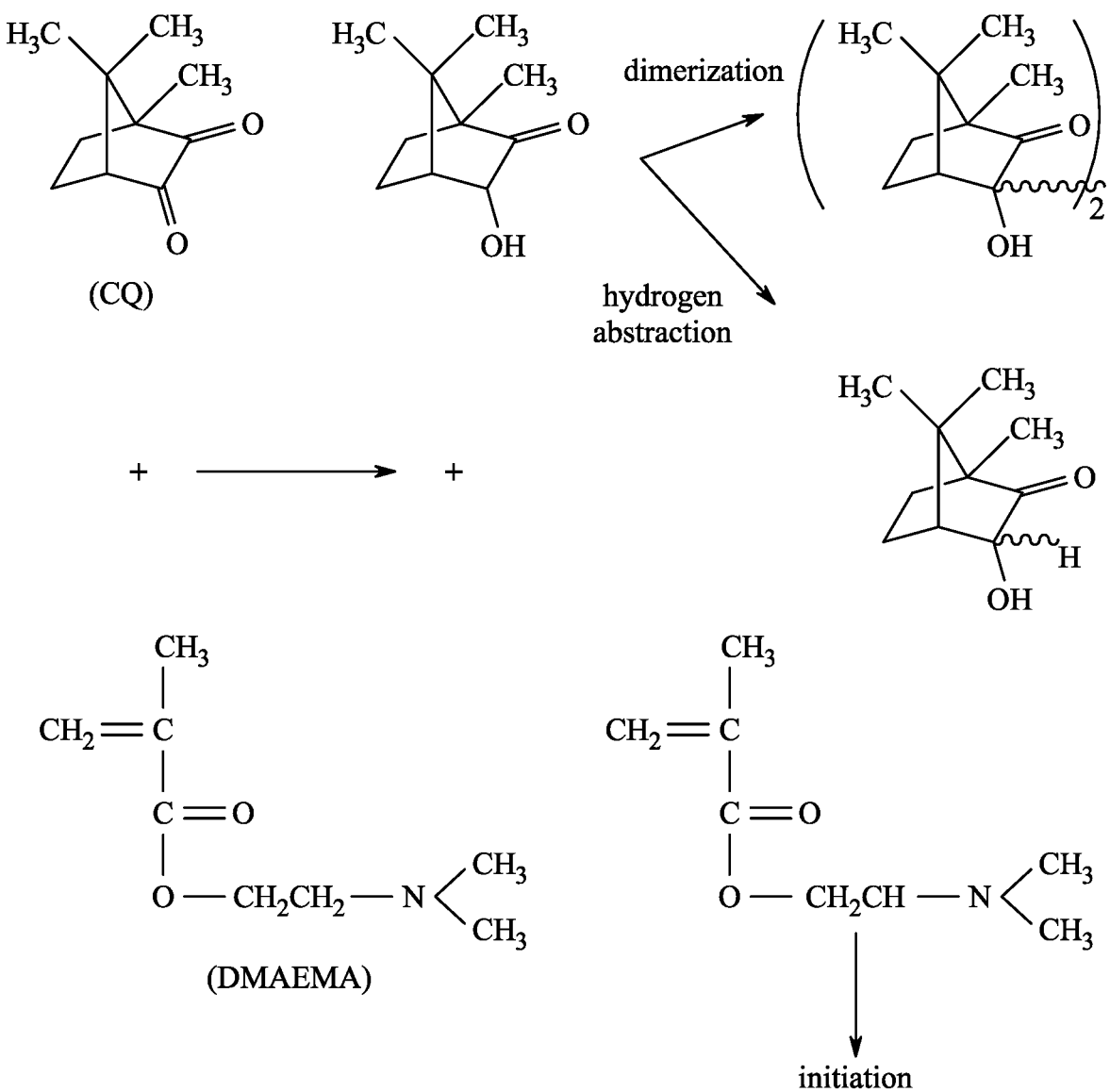
FIG. 6 shows mechanism of photoinitiation by camphorquinone/amine system.
Figure 7:
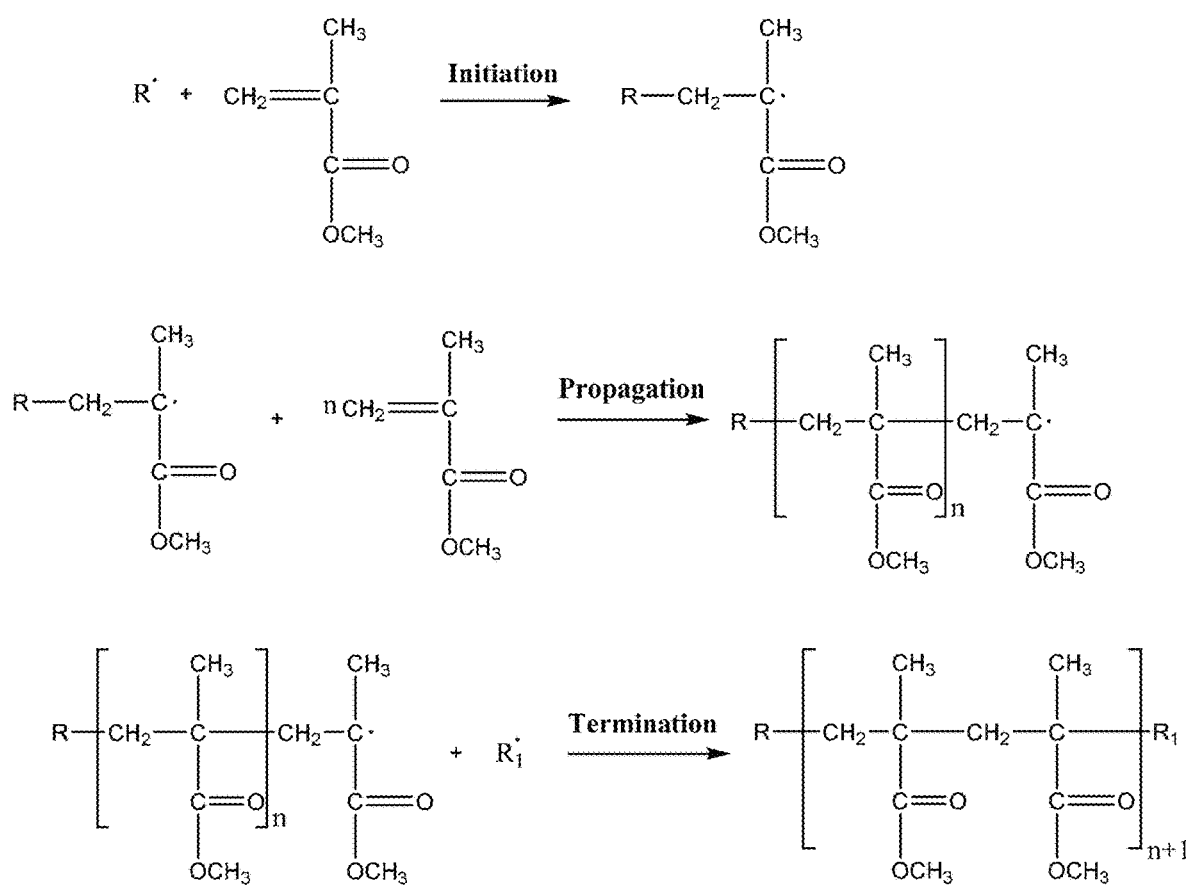
FIG. 7 shows free radical polymerization of methyl methacrylate.
Figure 8:
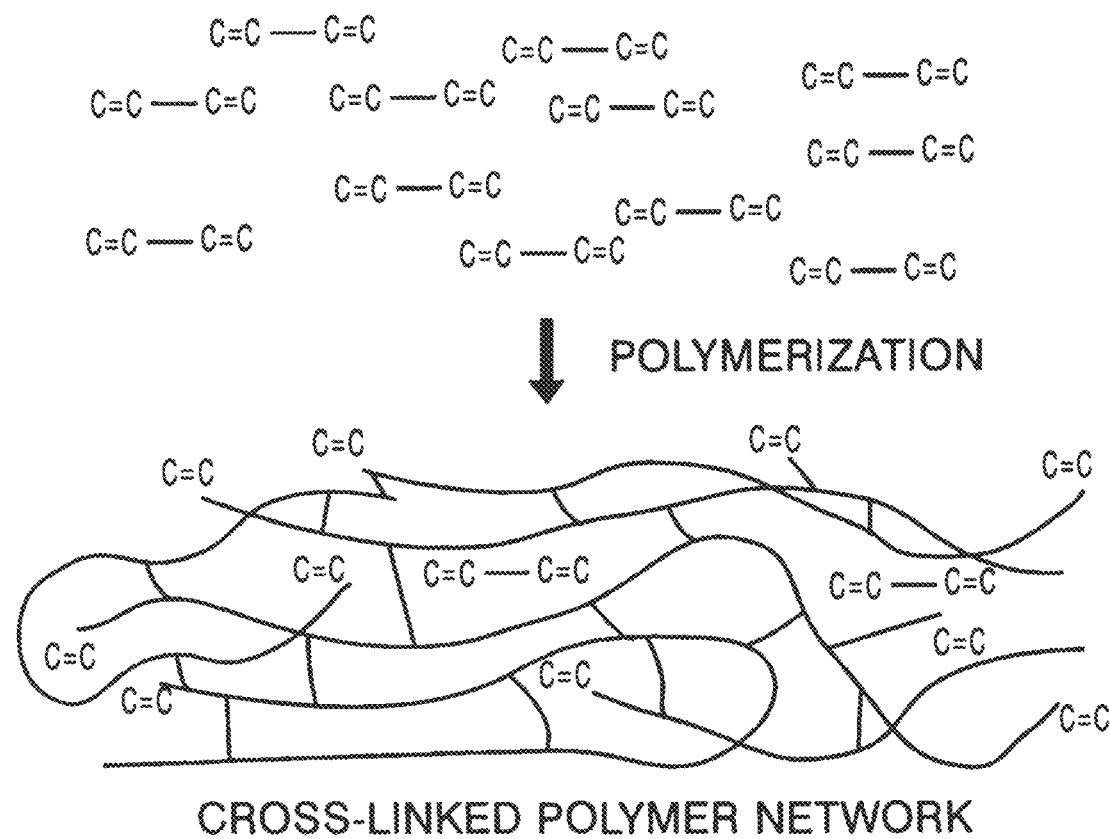
FIG. 8 is a schematic representation of polymerization of dimethacrylate monomers to form a cross-linked polymer network of dental composites containing small amounts of unreacted monomers and many pendant methacrylate groups (C=C).

Many dental composites are light-cured that harden under irradiation of UV and/or visible light with a wavelength in the range of 400-500 nm. For resin composites activated by light, a photoinitiator such as a diketone may be used. Camphorquinone (CQ) is a photoinitiator used frequently. The maximum absorption of camphorquinone is at around 468 nm. Camphorquinone is a 1,2-diketone which abstracts hydrogen from a co-initiator (polymerization accelerator) to give ketyl radicals (FIG. 6). Amines are regularly used co-initiators. The amino-alkyl radicals initiate the polymerization reaction while the ketyl radicals dimerize or disproportionate. Light-curable dental composites are advantageous for their fast and complete curing upon irradiation. Free radicals produced as described above can react with a monomer such as a vinyl monomer (e.g. methyl methacrylate) and initiate the polymerization process as shown in FIG. 7. After a free radical transfers to a monomer, it can react with another monomer in the propagation step. Polymer chains are generated by the colliding of growing units and repeating free radicals generation process. Free radicals eventually quench each other to form a stable molecule in the termination step. As shown in FIG. 8, free-radical polymerization of dimethacrylate monomers produces a three-dimension network.

In one or more embodiment, the polymerization initiator system present in the currently disclosed dental composite is a free radical initiator. In some embodiments, a free radical initiator is included in the polymerizable monomer liquid at a concentration in a range of about 0.01% to about 5.0%, about 0.1% to about 4.0%, about 0.5% to about 3.0%, or about 1.0% to about 2.0% by weight relative to the total weight of the polymerizable monomer. Exemplary free radical initiators include, but are not limited to, camphorquinone, benzil, benzophenone, acyl phosphine oxides, e.g. phenylbis(2,4,6-trimethylbenzoyl)phosphine oxide (Irgacure 819, BASF) and diphenyl(2,4,6-trimethylbenzoyl) phosphine oxide, azo compounds, e.g. azobisisobutyronitrile (AIBN), 1,1'-azobis(cyclohexanecarbonitrile) (ABCN), and 4,4'-azobis(4-cyanovaleric acid), and organic peroxides, e.g. benzoyl peroxide, lauroyl peroxide, methyl ethyl ketone peroxide (MEKP), tert-butyl hydroperoxide, and tert-butyl peroxybenzoate.

In some embodiments, the polymerization initiator system further comprises a polymerization accelerator (co-initiator) that works in conjunction with the polymerization initiator to promote or improve the speed of polymerization reaction. The polymerization accelerator may be added to the monomer liquid at a concentration in a range of about 0.1% to about 5.0% by weight relative to the total weight of the polymerizable monomer. Exemplary polymerization accelerators include, but are not limited to, N,N-dimethyl-p-toluidine, N,N-bis(2-hydroxyethyl)-p-toluidine, ethyl 4-(dimethylamino)benzoate, dimethylaminoethyl methacrylate, N-(2-cyanoethyl)-N-methyl aniline, 4-(N,N-dimethylamino)phenethyl alcohol, and 4-(N,N-dimethylamino)phenylacetic acid.

In a preferred embodiment, the polymerization initiator system consists of camphorquinone and ethyl 4-(dimethylamino)benzoate. In one embodiment, a combination of free radical initiator camphorquinone and co-initiator ethyl 4-(dimethylamino)benzoate at a weight ratio of about 1:5 to about 2:1, about 1:4 to about 1:1, or about 1:3 to about 1:2, is employed as the polymerization initiator system in the current disclosure.

Figure 9A:
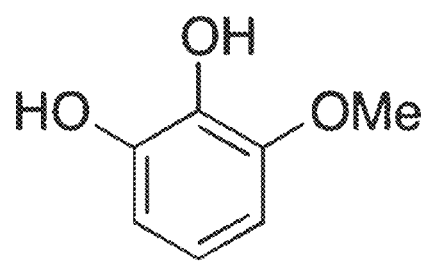
FIG. 9A shows the chemical structure of monomethyl ether substituted hydroquinone.
Figure 9B:
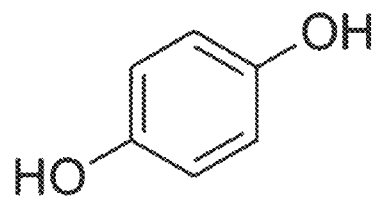
FIG. 9B shows the chemical structure of a hydroquinone, 1,4-dihydroxybenzene.
Figure 10:
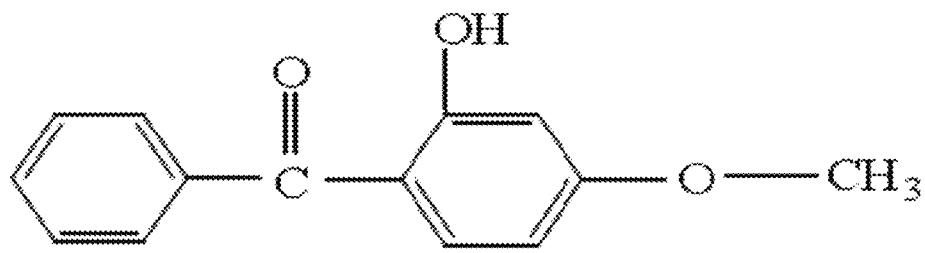
FIG. 10 shows the chemical structure of 2-hydroxy-4-methoxybenphenone.
Figure 11:
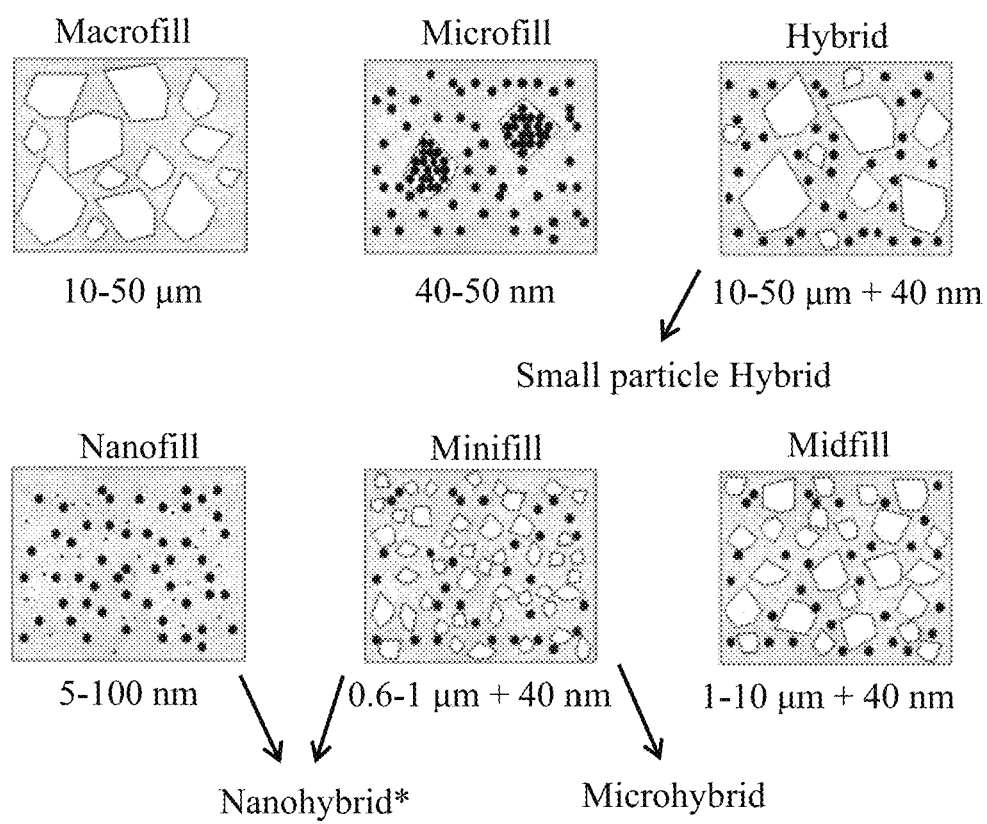
FIG. 11 demonstrates composite grouping according to the size of filler particles.

In order to achieve adequate storage stability, especially for dental composites that are cured through a free-radical curing mechanism, it may be desirable to include a polymerization inhibitor such as the monomethyl ether hydroquinone (FIG. 9) to the resin composite. When employed, only a small amount of the inhibitor is required to provide adequate stability. Ultraviolet radiation absorbers are added to enhance color stability by absorbing electromagnetic radiation. Frequently utilized absorber is 2-hydroxy-4-methoxy benzophenone (FIG. 10).

In some embodiments, a polymerization inhibitor is included as a mixture with the polymerizable monomers at a concentration of about 0.001% to about 1.0%, about 0.01 to about 0.8%, about 0.05% to about 0.6%, about 0.1% to about 0.5%, or about 0.2% to about 0.4% by weight relative to the total weight of the polymerizable monomer(s). Small amounts of polymerization inhibitors can consume unwanted free radicals generated during manufacturing, transportation and storage stages, thus help avoid premature polymerization of dental composites. Examples of polymerization inhibitors include hydroquinone, 4-methoxyphenol, 2,6-di-tert-butyl-4-methylphenol (BHT) and the like.

Typically dental composites are provided in ten or more shades to cover a range of natural human teeth (yellow to grey). Pigment can be mixed with standard shades to match the color of teeth outside the natural range. Special shades for incisal edges of anterior restorations and for bleached teeth are also available. In certain embodiments, the resin composite disclosed herein may further include a pigment, primarily for aesthetic reasons. Any organic and inorganic pigment is suitable for the purpose of the invention, provided it is not toxic as are some cadmium and lead compounds. Suitable pigments and dyes include, but are not limited to, titanium dioxide, zinc oxide, lake pigments and the like. The pigment is preferably pre-grinded into one of the components of the composite, since it is unlikely to function well if added as a separate powder. The pigment may present in 0.01-1 wt % relative to the total weight of the resin composite, preferably 0.1-0.8 wt %, preferably 0.2-0.6 wt %, preferably 0.3-0.5 wt % relative to the total weight of the resin composite.

The resin composite of the current disclosure may further include a fluoride source selected from sodium fluoride, potassium fluoride, aluminum fluoride, zinc fluoride, stannous fluoride, ammonium fluoride, sodium monofluorophosphate and the like. The fluoride source may present in an amount of 0.01-2 wt %, 0.05-1 wt %, 0.1-0.5 wt %, or 0.2-0.4 wt % relative to the total weight of the resin composite.

Methods of preparing resin composites are generally known to those skilled in the art. For example, the resin composite disclosed herein may be prepared by (i) mixing polymerizable monomers (e.g. bis-GMA, TEGDMA, and UDMA) at aforementioned weight ratio to form a monomer liquid, (ii) adding photoinitiators (e.g. CQ) and polymerization accelerators/co-initiators (e.g. EDBA) to the monomer liquid to form a polymerizable resin at aforementioned weight ratio and amount, (iii) adding fillers (e.g. the azole-functionalized silica nanoparticles, aluminosilicates, and/or zirconia) to the polymerizable resin at the aforementioned weight ratio to form a composite mixture, (v) mixing the composite mixture by agitating for 0.1-12 hours, 0.5-6 hours, or 1-3 hours to form the resin composite. In a preferred embodiment, the resin composite is prepared at a temperature of 5° C. to 40° C., 10° C. to 30° C., 15° C. to 28° C., or at around 25° C.

Methods of agitating a mixture include, without limitation, using an agitator, a vortexer, a rotary shaker, a magnetic stirrer, a centrifugal mixer, a dual asymmetric centrifugal mixer, or an overhead stirrer. In one embodiment, the composite mixture is agitated by sonication in an ultrasonic bath or with an ultrasonic probe. In another embodiment, the mixture is left to stand without being stirred. In another embodiment, the mixture is agitated using a magnetic stirrer with a rotational speed of at least 250 rpm, preferably at least 500 rpm, more preferably at least 750 rpm. In a preferred embodiment, the composite mixture is mixed with a spatula. In another preferred embodiment, the mixture is mixed using a dual asymmetric centrifugal mixer, e.g. SpeedMixer (FlackTek Inc.) at a speed of at least 800 rpm, preferably at least 1000 rpm, more preferably at least 1500 rpm.

According to a second aspect, the present disclosure relates to a dental restoration comprising a cured resin composite of the first aspect. Curing conditions and procedures are generally known to those skilled in the art. In some embodiments, wherein the polymerization initiator can be activated by an external light source, the currently disclosed dental composite may be cured by applying light at a proper wavelength and with sufficient intensity to the dental composite to initiate and propagate polymerization. Visible light activation is preferred as UV irradiation is harmful to oral mucosa. Light emitted by a hydrogen lamp with a wavelength in the range of 380-500 nm triggers photopolymerization. New light sources, e.g. blue-light emitting diodes (LED) have been introduced (Rutsch, W., Dietliker, K., and Hall, R. G. (1993). Mono- and di-acylphosphine oxides, U.S. Pat. No. 5,218,009 A). In one or more embodiments, light is applied to the resin composite during curing for a period of time of at least 10 seconds, at least 20 seconds, at least 30 seconds, at least 40 seconds, at least 1 minute, at least 2 minutes, or at least 5 minutes. Depending on the identity of the photo-initiator, a light source at a wavelength of 300-800 nm, preferably 350-700 nm, preferably 375-650 nm, preferably 400-600 nm, preferably 425-550 nm, preferably 450-500 nm may be applied. Depending on the composition of the resin composite, the curing may be performed at a light intensity of about 200-2000 mW/cm$^2$, about 400-1500 mW/cm$^2$, about 600-1200 mW/cm$^2$, or about 800-1000 mW/cm$^2$. Applicable light sources for the curing described herein may be commercially available from a variety of vendors, including, but not limited to, Elipar™ S10 LED Curing Light (3M ESPE), XL3000 (3M ESPE), PROLITE (Dentsply Sirona), SPECTRUM (Dentsply Sirona), VIVALUX II (Ivoclar-Vivadent), and OPTILUX 500 (Demetron-Kerr).

Important properties of dental restorations include polymerization shrinkage, mechanical properties, water sorption and solubility, biocompatibility, thermal properties, radiopacity, color, and fluoride release. In general, dental resin composites contract as they polymerize (Rueggeberg, F. A., "From vulcanite to vinyl, a history of resins in restorative dentistry", The Journal of prosthetic dentistry, vol. 87, pp. 364-379, 2002, incorporated herein by reference in its entirety). This is due to a decrease in the distance between the atoms of monomers when they react to form covalent bonds and thus a reduction in the amount of free volume in dental resin composites (Braga, R., and Ferracane, J., "Contraction stress related to degree of conversion and reaction kinetics", Journal of Dental Research, vol. 81, pp. 114-118, 2002; and Schneider, L. F. J., Cavalcante, L. M., and Silikas, N., "Shrinkage stresses generated during resin-composite applications: a review", Journal of dental biomechanics, vol. 1, 2010, each incorporated herein by reference in their entirety). Resin composition, volume fraction of filler, and degree of polymerization of the resin matrix influences the amount of volumetric contraction in a dental resin composite (Braga, R. R., Ballester, R. Y., and Ferracane, J. L., "Factors involved in the development of polymerization shrinkage stress in resin-composites: a systematic review", Dental Materials, vol. 21, pp. 962-970, 2005, incorporated herein by reference in its entirety). For example, volumetric shrinkage of bis-GMA is approximately 5% to 6.1% (De Gee, A., Feilzer, A., and Davidson, C., "True linear polymerization shrinkage of unfilled resins and composites determined with a linometer", Dental Materials, vol. 9, pp. 11-14, 1993; Feilzer, A. J., De Gee, A. J., and Davidson, C. L., "Curing contraction of composites and glass-ionomer cements", The Journal of prosthetic dentistry, vol. 59, pp. 297-300, 1988, each incorporated herein by reference in their entirety), while volumetric shrinkage of TEGDMA is approximately 12.5%. Commercially available dental resin composites have been reported to have a volumetric contraction within the range of 1-5%, 1-6%, or 1-3% (Heintze, S., Liechtenstein, F., and Zahnmed, S. M., "Relevance of in vitro tests of adhesive and composite dental materials", Schweiz Monatsschr Zahnmed, vol. 121, pp. 1024-1032, 2011, incorporated herein by reference in its entirety). These reported contraction values are regarded as estimates, since they rely on the degree of polymerization. (Labella, R., Lambrechts, P., Van Meerbeek, B., and Vanherle, G., "Polymerization shrinkage and elasticity of flowable composites and filled adhesives", Dental materials, vol. 15, pp. 128-137, 1999, incorporated herein by reference in its entirety). The variation in volumetric shrinkage is resulted from several factors, including the presence of inorganic filler in dental resin composites. In general, a higher filler volume fraction leads to a decrease in polymerization shrinkage (Puckett, A. D., Fitchie, J. G., Kirk, P. C., and Gamblin, J., "Direct composite restorative materials", Dental Clinics of North America, vol. 51, pp. 659-675, 2007, incorporated herein by reference in its entirety). For instance, a hybrid composite has filler particles which take up approximately 60% of its volume and shrinks 1-3% by volume on average. Composites with low viscosity shows volume contractions of up to 5%, mostly because of less inorganic substance, which is usually lower than 50% by volume (Weinmann, W., Thalacker, C., and Guggenberger, R., "Siloranes in dental composites", Dental Materials, vol. 21, pp. 68-74, 2005, incorporated herein by reference in its entirety). Despite an inorganic content of typically about 40% by volume, micro-filled composites show a similar degree of shrinkage comparing to hybrid composites.

Figure 12:
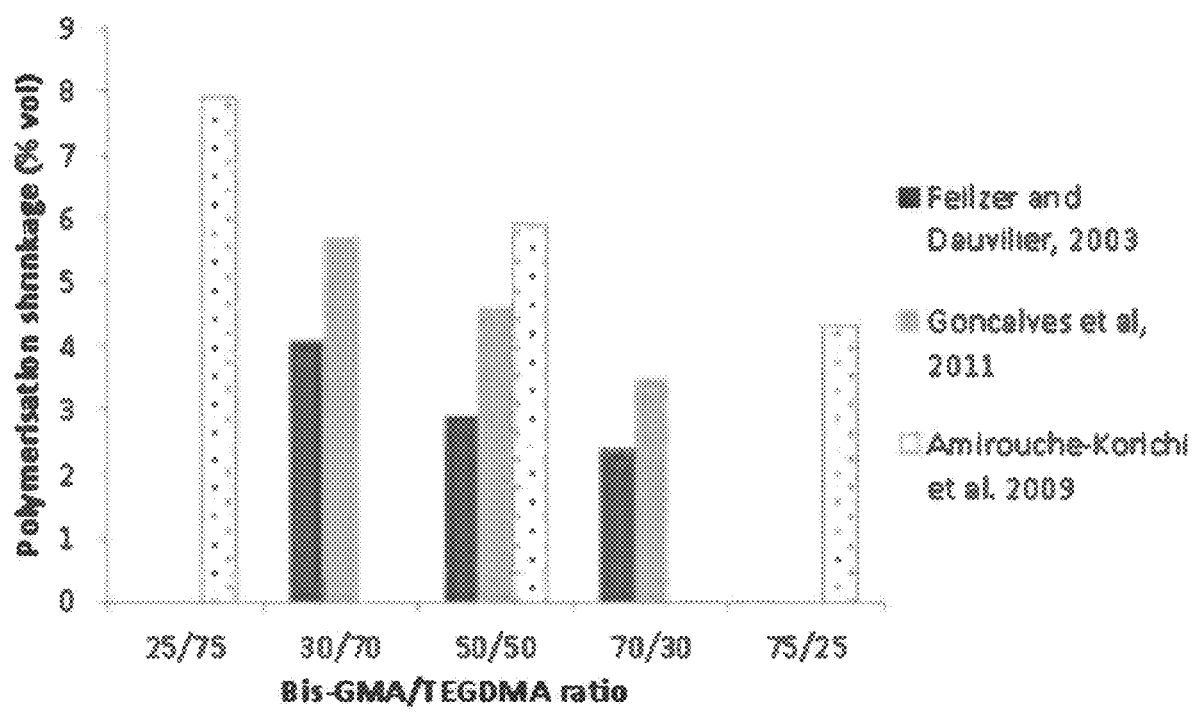
FIG. 12 is a summary of effect of bis-GMA/TEGDMA ratio on polymerization shrinkage based on previous studies.

Incorporation of fibers to a composite has been studied infrequently. One study found that placing unidirectional fibers strengthens the restoration but results in a higher shrinkage (0.41%) when compared with a commercially available PFC (0.32%), while biaxial fiber reinforced material shrank the least (0.03%) (Anttila, E. J., KrintilA, O. H., Laurila, T. K., Lassila, L. V., Vallittu, P. K., and Hernberg, R. G., "Evaluation of polymerization shrinkage and hydroscopic expansion of fiber-reinforced biocomposites using optical fiber Bragg grating sensors", dental materials, vol. 24, pp. 1720-1727, 2008, incorporated herein by reference in its entirety). Another study found that the shrinkage stress of fiber reinforced dental resin composites (2.45±0.11) was significantly lower than that of a PFC (2.04±0.09) (Garoushi, S., Vallittu, P. K., Watts, D. C., and Lassila, L. V., "Effect of nanofiller fractions and temperature on polymerization shrinkage on glass fiber reinforced filling material", dental materials, vol. 24, pp. 606-610, 2008a, incorporated herein by reference in its entirety). This could be explained by the orientation of fibers in the material. When the fibers are oriented in the same direction, the shrinkage appears to increase. Materials with randomly oriented fibers in the material showed a much lower shrinkage volume, which may result from formation of a three-dimensional network in the presence of randomly oriented fibers. It has been found that, similar to PFCs, the incorporation of nano-filler particles to an FRC reduce the polymerization shrinkage significantly (Garoushi, S., Vallittu, P. K., Watts, D. C., and Lassila, L. V., "Polymerization shrinkage of experimental short glass fiber-reinforced composite with semi-inter penetrating polymer network matrix", dental materials, vol. 24, pp. 211-215, 2008b, incorporated herein by reference in its entirety). Contraction is an intrinsic property of dimethacrylate-based resin composite. The concentration of diluent monomers in the bis-GMA based resin composites is found to affect shrinkage. As illustrated in FIG. 12, dental resin composites have shown higher contraction stress and volumetric shrinkage due to higher TEGDMA/bis-GMA ratios (Feilzer, A., and Dauvillier, B., "Effect of TEGDMA/Bis-GMA ratio on stress development and viscoelastic properties of experimental two-paste composites", Journal of Dental Research, vol. 82, pp. 824-828, 2003, incorporated herein by reference in its entirety). This is because of improved conversion leads to increased volume contraction. In addition, the low viscosity of diluent enhances mobility in the reaction system, which allows a more efficient conversion. The volumetric contraction of composites has also been indicated to be proportional to degree of conversion. Volumetric shrinkage and modulus of elasticity increase as the degree of polymerization of the polymer matrix increases (Silikas, N., Eliades, G., and Watts, D., "Light intensity effects on resin-composite degree of conversion and shrinkage strain", Dental Materials, vol. 16, pp. 292-2%, 2000, incorporated herein by reference in its entirety). The chemical property of monomers used can also impact polymerization contraction of resin-based dental composites. The polymerization reaction of methacrylates involves the conversion of carbon double bonds (C=C) to carbon single bonds (C—C), whereas other monomers may use a ring-opening reaction for monomer conversion.

A degree of conversion in a resin composite may be determined after curing. The degree of conversion (% DC) can be calculated by comparing the ratio of the aliphatic carbon-carbon double bond (C=C) relative to an internal standard, e.g. an aromatic or alkyl component for the cured and uncured dental composites. Useful analytical tools for determining % DC include Fourier-transform infrared (FT-IR) spectroscopy, near-infrared (NIR) spectroscopy, Raman spectroscopy, and nuclear magnetic resonance (NMR) spectroscopy. For example, DC % of the cured dental restoration described herein may be measured using a FT-IR spectrometer before and after curing. In some embodiments, wherein the polymerizable monomer comprises bis-GMA, DC % of the dental restorative may be calculated as: DC %=100×{1−[(A1637/A1608)$_{after\ curing}$/(A1637/A1608)$_{before\ curing}$]}, wherein A1637 and A1608 represent FT-IR peak height of aliphatic C≡C bond at 1637 cm$^{-1}$ and aromatic C=C at 1608 cm$^{-1}$, and "before curing" and "after curing" designate FT-IR spectra collected for resin composite before and after curing. In a preferred embodiment, the dental restoration formed by a cured resin composite of the present disclosure in any of its embodiments has a DC % in the range of 30%-99%, 35%-90%, 45% to 80%, or 55%-70%.

The mechanical property of a material is governed by laws of mechanics. Dental materials being static in nature has mechanical properties which can be measure as a function of the materials' resistance to either deformation or breakage under forces applied. Each part of any machine (e.g. a composite material) should be able to bear up applied forces in order to perform maximally. These forces are accordingly the ones a material face when it functions. The knowledge of these properties can help clinicians choose restorative materials and other prosthesis. Major forces which act upon a material can be grouped as tensile, compressive, shearing and torsional forces.

Figure 13:
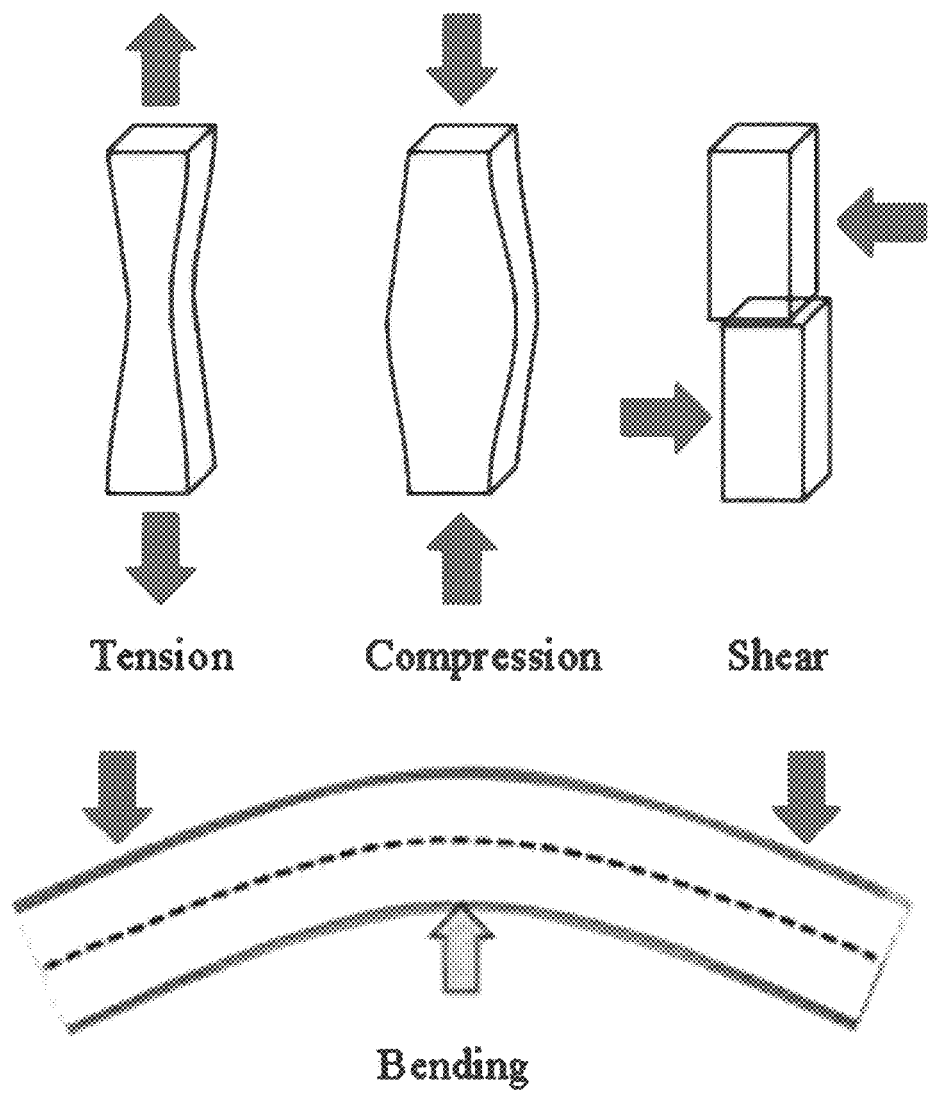
FIG. 13 demonstrates different types of force.

The elongation, shortening and deformation around a central axis and twisting around a central axis of a material is cause by application of these forces respectively. In addition bending forces, a compilation of tension, compression and shear forces, (sometimes called the combination stress) can also be observed. During the time of estimation of those stresses which is subjected to a dental restorative material intraorally, bending forces are routine. A visual demonstration of these forces is given in FIG. 13. In dentistry, stresses are restricted to tensile, compressive and shear stresses. There is some interplay between these stresses as evidenced during flexural loading (e.g. on a bridge-occlusal load between two fixed abutments). In cases like this, brittle dental materials are likely to fail because of the tensile stress generated. Levels of stress that cause elastic deformation in materials do not cause permanent deformation, while levels of stress that cause plastic deformation (non-elastic deformation) leads to some degree of permanent deformation. In the presence of permanent deformation, material fractures occur. For brittle materials that show only elastic deformation, a stress at or beyond the elastic limit will lead to a disastrous failure. Therefore, understanding of the mechanical properties of restorative or prosthetic materials is important.

Strain ($\varepsilon$) can defined as the deformation in a material when subjected to stress and it may either be elastic or plastic. Strain can also be defined as the change in length ($\Delta l$) per original length ($l_0$). Mathematically stress and strain can be written as the following equation:

$$\text{Strain}(\varepsilon) = \frac{\Delta l}{l0}.$$

Figure 14:
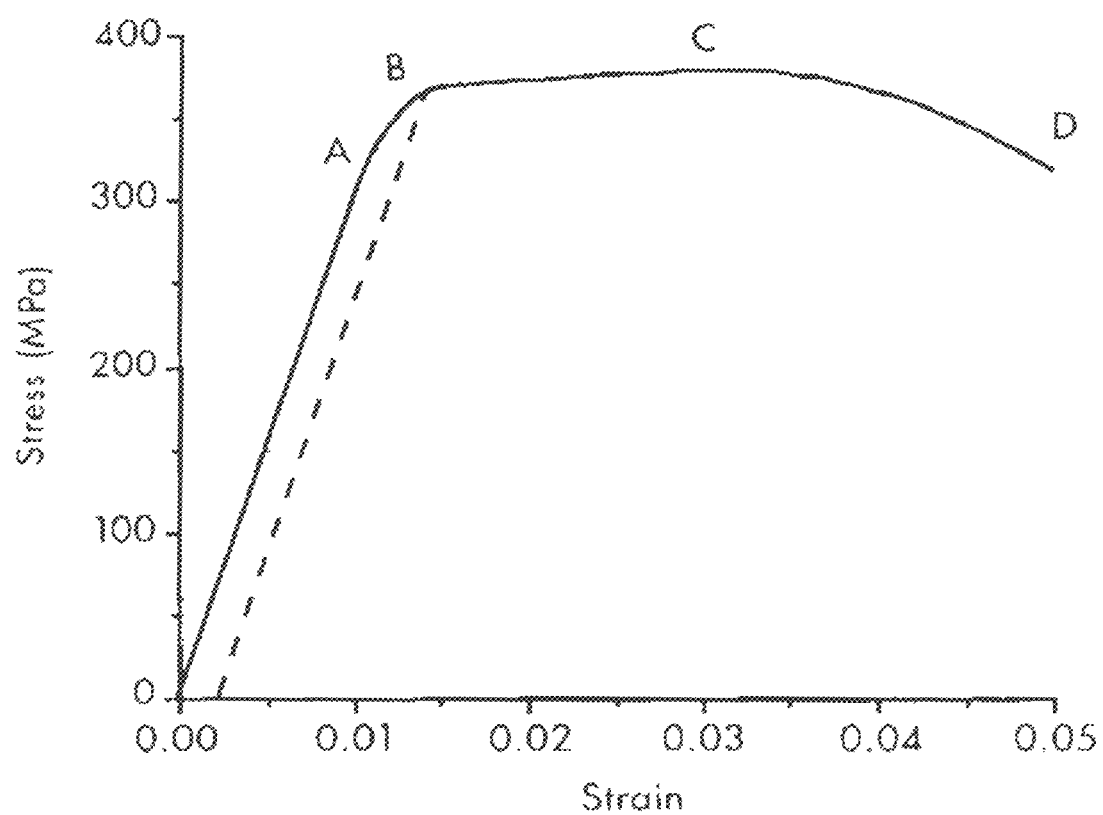
FIG. 14 shows the curve of stress-strain for a material under a tensile stress.

The relationship between stress and strain is unique for each material. This can be demonstrated graphically in the form of a stress-strain curve (FIG. 14). In addition, we can measure other mechanical properties from the curve. The slope from of the elastic region gives the elastic modulus, E, from the stress-strain curve (also known as Young's modulus of elasticity) and is a representation of the stiffness or rigidity of a material.

Figures 15, 16:
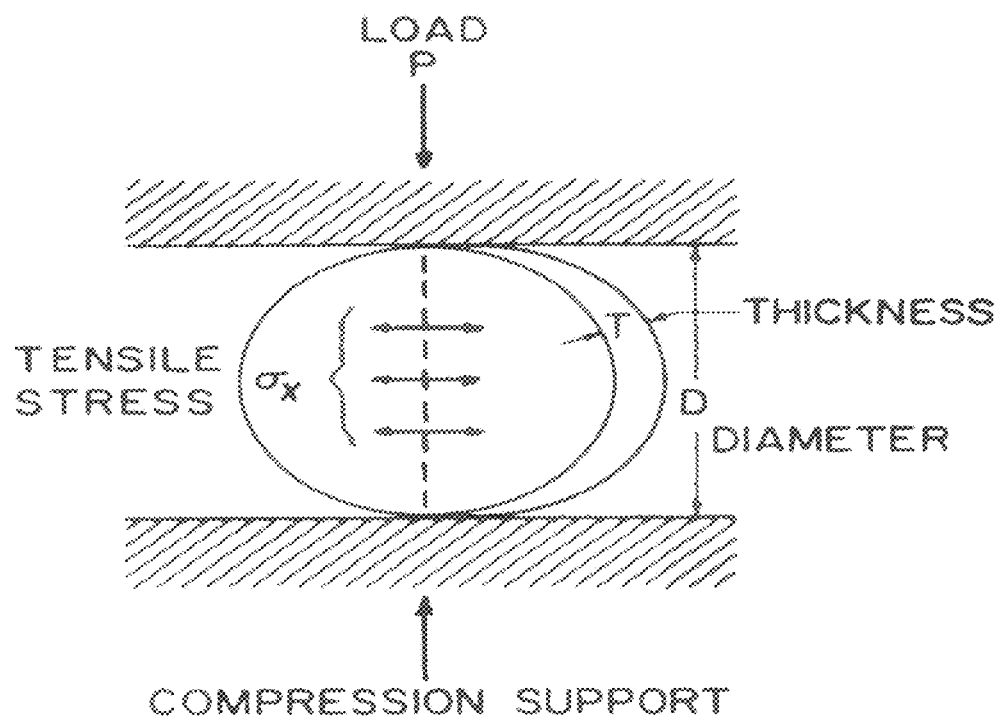
FIG. 15 is a drawing to illustrate tensile stress developed by a compression force in brittle materials (Sideridou, I. D. Dental polymer composites, Encyclopedia of Polymer Composites", Nova Science Publishers Inc: New York, 2009, incorporated herein by reference in its entirety).
FIG. 16 shows the equation for determining flexural strength.

Compressive strength, or compression strength, mainly occurs in the process of chewing because many of the forces of mastication are compressive. Materials which are generally brittle and weak in tension are evaluated mostly by using compressive strength. These materials are not use in places where tensile forces dominates. When a structure is subjected to compression, the failure of the body of the structure may happen due to the complex stress formations in the body. This is illustrated by a cross-sectional view of a right cylinder subjected to compression as shown in FIG. 15. It is apparent that the compression forces applied towards the sample resolves into shear forces along a cone-shaped area and also at the central position of the mass. In addition, tensile forces occur due to the action of two cones on the cylinder. Due to the resolution of these forces in the body of the material, using standard sizes and dimension has become necessary to get reproducible test results. FIG. 15 indicates that force distribution within a short sample is complex due to formation of cones that overlap at the cylinder ends. If a sample is long, buckling may occur. It is suggested that the length of a cylinder should be approximately two times that of the diameter (Sakaguchi, R. L., and Powers, J. M. Craig's restorative dental materials, Elsevier Health Sciences, 2012, incorporated herein by reference in its entirety). Compression strength is often measured on a universal testing machine (see example 4). In a preferred embodiment, the dental restoration formed by a cured resin composite of the present disclosure in any of its embodiments has a compression strength of 40-500 MPa, preferably 50-450 MPa, preferably 75-400 MPa, preferably 100-350 MPa, preferably 125-300 MPa, preferably 150-250 MPa, preferably 175-200 MPa.

Figure 17:
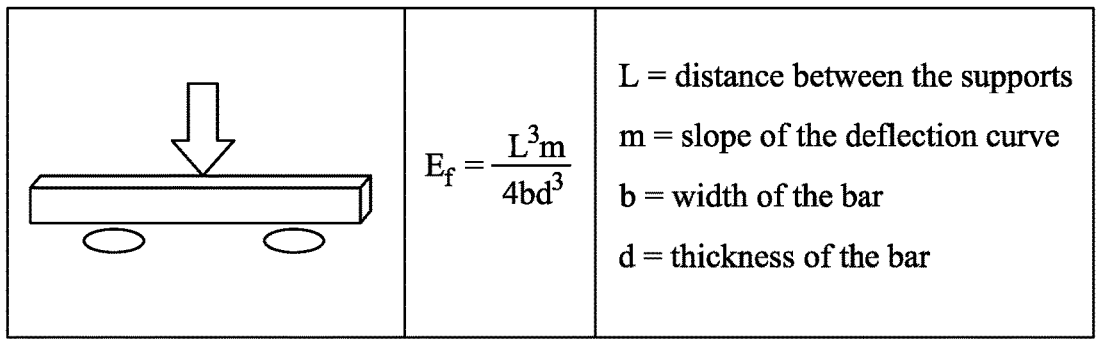
FIG. 17 shows the equation for determining flexural modulus.
Figure 18:
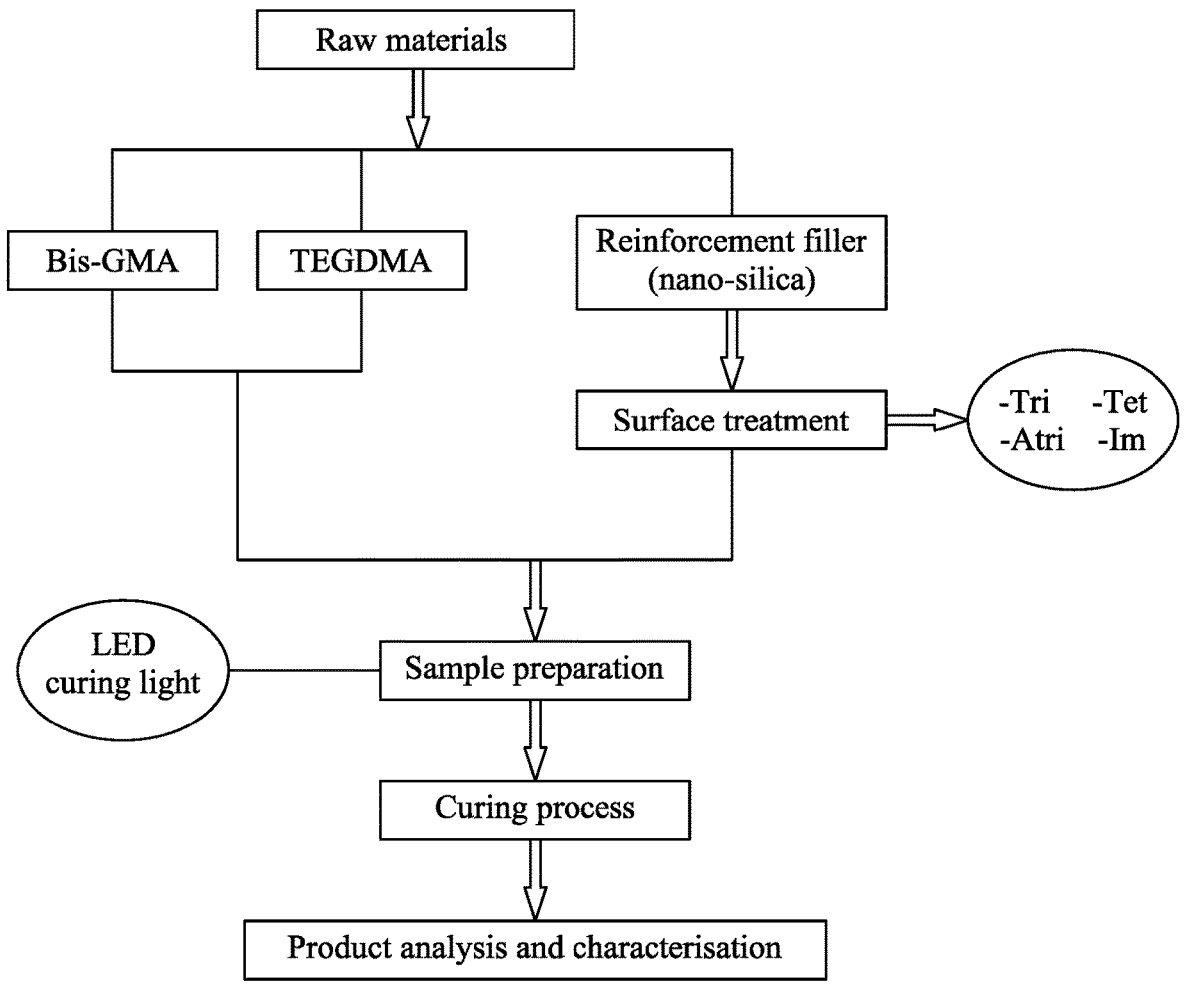
FIG. 18 is a flow chart diagram showing the steps in composite production.

The amount of force require to break a sample specimen gives the flexural strength of the material (FIG. 16). Materials generally deform upon the application of force in form of load. The extent of deformation under load gives its modulus of elasticity (FIG. 17).

Modulus of elasticity is measured at the same time when load is applied on material as it gets deformed. Lower modulus of elasticity occurs when there is a high deformation in the material. Low modulus of elasticity is an unwanted property for dental composites. High flexural strength in combination with a tooth-like, high modulus of elasticity is desirable for dental composites. The elastic modulus is usually measured by a three-point flexural strength test through analyzing the deflection of the material in relationship to the applied force. Elastic modulus is dominated by the amount of filler and increases exponentially with the volume fraction of filler. The stiffness of a material is represented by modulus of elastic in the elastic range. A low modulus indicates a flexible material. This stiffness is important in applications where high biting forces are involved and wear resistance is essential. The flexural modulus is evaluated by applying a load to a material specimen that is supported at each end (see example 5). Fracture stress is the stress which causes material to fracture. In FIG. 14, the test sample fractured at point D at the end of the curve. In a preferred embodiment, the dental restoration formed by a cured resin composite of the present disclosure in any of its embodiments has a strain at break of 3-20 GPa, preferably 4-18 GPa, preferably 5-15 GPa, preferably 6-12 GPa, preferably 7-10 GPa, preferably 8-9 GPa. In a preferred embodiment, the dental restoration formed by a cured resin composite of the present disclosure in any of its embodiments has an elastic modulus of 0.4-20 GPa, preferably 0.75-18 GPa, preferably 1.0-16 GPa, preferably 1.5-14 GPa, preferably 2-12 GPa, preferably 3-10 GPa, preferably 4-8 GPa, preferably 5-6 GPa.

Dental composites absorb water and may release unreacted monomer molecules in wet oral environment. Water sorption happens largely as a result of direct absorption from polymer matrix. Glass filler do not absorb water but can attract water onto the composite surface. The quantity of water sorption is dependent on the type of polymer matrix and the degree of interaction between the matrix and the filler. As a result, water sorption is affected by the matrix structure and composition of a composite. Absorption of liquid into the organic phase of a composite leads to two opposing processes, which are extraction of unreacted material and swelling of composite due uptake of water/solvent, respectively. The extraction of unreacted monomers by a solvent causes contraction, weight loss and reduced mechanical properties. While swelling due to solvent uptake causes a weight increase. Additionally, diffusion of solvent into the polymer network causes separation of the polymer chain. Since polymer chain networks contain micro-voids formed during polymerization and free volumes between chains, a part of the solvent is contained in the micro-voids with no volume change. Studies on water sorption of some light-cured resins including TEGDMA, bis-GMA, UDMA, and bis-EMA revealed that TEGDMA has the highest amount of water uptake and discharges the least amount of unreacted monomer. UDMA and bis-EMA absorb less water and discharge higher amount of unreacted monomer. Bis-GMA absorbs less water than the polymer of TEGDMA, however, it adsorbs higher amount of water than the polymers made by UDMA and bis-EMA (Sideridou, I., Tserki, V., and Papanastasiou, G., "Effect of chemical structure on degree of conversion in light-cured dimethacrylate-based dental resins", Biomaterials, vol. 23, pp. 1819-1829, 2002, incorporated herein by reference in its entirety). Solubility can be determined by measuring the quantity of dischargeable unreacted monomers in dental biomaterials absorbed by a solvent. The unreacted monomer is entrapped in a microgel between polymer chains during polymerization and absorbed to the surrounding network (monomer pools). Monomers trapped inside microspores are more prone to be discharged than monomers in the micro-gels. ISO 9000 standard suggests that a suitable dental restorative resin should have a water sorption that is lower than 50 $\mu g/mm^3$ and a solubility that is lower than 5 $\mu g/mm^3$. In a preferred embodiment, the dental restoration formed by a cured resin composite of the present disclosure in any of its embodiments has a water sorption of 0.01-0.4 mg/mL, preferably 0.02-0.3 mg/mL, preferably 0.03-0.2 mg/mL, preferably 0.04-0.1 mg/mL, preferably 0.05-0.08 mg/mL. In a preferred embodiment, the dental restoration formed by a cured resin composite of the present disclosure in any of its embodiments has a water solubility of 0.002-0.4 mg/mL, preferably 0.003-0.2 mg/mL, preferably 0.004-0.1 mg/mL, preferably 0.005-0.05 mg/mL, preferably 0.01-0.02 mg/mL.

Polymer composites are complex structures from which various components can be released including degradation products, impurities of monomers, unreacted monomers, and additives. Such release might irritate soft tissue, trigger bacteria growth, and promote allergic reactions. The released materials from glass ionomer cements (GIC) and polymer composites have been recently evaluated by Geurtsen (Geurtsen, W., Lehmann, F., Spahl, W., and Leyhausen, G., "Cytotoxicity of 35 dental resin composite monomers/additives in permanent 3T3 and three human primary fibroblast cultures", Journal of biomedical materials research, vol. 41, pp. 474-480, 1998, incorporated herein by reference in its entirety). It was found in a number of in vitro studies that some demonstrated genotoxic, cytotoxic, mutagenic or estrogenic effects, and gingival/oral mucosa and pulpal reactions (Schmalz, G., "The biocompatibility of non-amalgam dental filling materials", European journal of oral sciences, vol. 106, pp. 696-706, 1998, incorporated herein by reference in its entirety). Methacrylates and acrylates are often found to cause cytotoxic effects. Cytotoxicity assessment of 39 methacrylates and acrylates used in dental polymer composites has revealed a connection between the degree of cytotoxicity and their chemical structure. TEGDMA, bis-GMA, and UDMA showed high cytotoxicity. It was found recently that TEGDMA is moderately mutagenic in V79 cells at sub-toxic concentrations. At low concentrations of 0.02 mM and 0.6 mM, bis-GMA has also shown positive responses in DNA-synthesis inhibition test, which is used to evaluate the mutagenic effects of substances in human genes. In addition, it was reported that TEGDMA might promote the growth of major cariogenic microorganisms such as *Lactobacillus acidophilus* and *Streptococcus sobrinus* (Sideridou, I. D., and Achilias, D. S., "Elution study of unreacted Bis-GMA, TEGDMA, UDMA, and Bis-EMA from light-cured dental resins and resin composites using HPLC", Journal of Biomedical Materials Research Part B: Applied Biomaterials, vol. 74, pp. 617-626, 2005, incorporated herein by reference in its entirety). In one or more embodiments, the cytotoxicity of the dental restoration formed by a cured resin composite of the present disclosure increases as the weight percentage of the azole-functionalized silica nanoparticles relative to the total weight of the resin composite increases.

The surface hardness of a dental material can be analyzed readily by a number of techniques including Brinell, Knoop, Vickers, Rockwell, and Shore A hardness tests. These hardness tests have various parameters such as indenter material, geometry and load. Material type, desired degree of localization, and expected hardness range are factors deciding which hardness test to perform. The general procedure for testing hardness independent of the specific test is as follows. On the surface of the dental material a standard force is applied. The applied force causes indentation due to the penetrating force. The depth, width and area of this indentation (symmetrical) can be measured by using a microscope. The tabulated hardness values are related to indentation dimensions. Under a fixed force applied using a standardized indenter, the dimension of indentation is inversely related to the material's penetration resistance. Hence a softer material endures a lighter weight.

Wear is the process by which a material is removed or displaced by interfacial forces which are produced when two surfaces rubbing against each other. In an oral environment, the following types of wear may occur, including adhesive wear, corrosive wear, surface fatigue, and abrasive wear. Adhesive wear is characterized by the formation and disruption of micro junctions. Corrosive wear is secondary process which involves physical removal of a protective layer, which depends on the chemical activity of the wear surface. The sliding action of surfaces removes any surface barriers and causes accelerated corrosion. Fatigue wear may be caused by repetitive loading which produces cyclic stresses leading to growth of fatigue cracks. These cracks often form below the surface and develop parallel to it before bending towards the surface or coalescing with other cracks. Abrasive wear involves a soft surface being in contact with a harder surface. In this type of wear particles are pulled off of one surface and stick to the other during sliding. When two surfaces rub together, the harder surface may indent, grooves in, or cut away materials from the softer surface.

The expansion due to a change in temperature is a critical issue that may impact bonding between a restoration and tooth structure. As a result of a large variation between their coefficients of linear thermal expansion (CLTE), when the temperature changes around a restored tooth, dimensional changes can occur at the tooth and restorative substance. The expansion and contraction due to temperature increase and/or decrease lead to stress forming at the border between the restorative and tooth. A micro-leakage may be produced at the margins of the restoration which can harbor acids and microorganism. Acids and microorganisms further lead to sensitivity and eventually secondary caries. In addition, toxic products released by microorganisms can damage pulp. Furthermore, gathering of debris will lead to staining at the margin of restorations. There is a strong connection between micro-leakages and coefficient of linear thermal expansion. It was found that a driving force that causes failure in restoration is the difference in CLTEs between tooth structure and restoration. Accordingly, a restorative material is preferred to have a similar coefficient of thermal expansion as enamel and dentine of tooth. For commercial polymer composites, the coefficient was found to range from $26 \times 10^{-6}$ to $35 \times 10^{-6}/°$ C., from $26 \times 10^{-6}$ to $83.5 \times 10^{-6}/°$ C., or from $20 \times 110^6$ to $80 \times 10^{-6}/°$ C. at a temperature range of 0-600° C. Enamel and dentine have coefficients of thermal expansion of $17 \times 10^{-6}/°$ C. and about $1 \times 10^{-6}/°$ C., respectively (Sideridou, I., Achilias, D. S., and Kyrikou, E., "Thermal expansion characteristics of light-cured dental resins and resin composites", Biomaterials, vol. 25, pp. 3087-3097, 2004, incorporated herein by reference in its entirety). Since the thermal expansion of composites is higher than that of tooth structure, composite restorations experience a higher change in dimensions with changing oral temperature than a tooth structure does. A composite containing a higher percentage of polymer matrix usually has a higher CLTE as the polymer has a larger CLTE value than fillers (Powers, J. M., and Wataha, J. C. Dental Materials: Properties and Manipulation, Elsevier Health Sciences, 2014, incorporated herein by reference in its entirety). The thermal conductivity of composite is much lower than that for metallic restorations and closely matches that of enamel and dentine. Therefore composites provide good thermal insulation for dental pulp.

Because of their quartz fillers, early composites were characteristically radiolucent. A clinical assessment was conducted either by direct observation or by trans-illumination. Later, composites containing glasses made up of atoms with high atomic numbers, e.g. strontium, barium, and zirconium were introduced. Fillers made from lithium, aluminium glasses, quartz or silica are not radiopaque, and they must be mixed with other fillers to obtain radiopacity. A reference standard of radiopacity is aluminium. Dentine of 2 mm thickness has a radiopacity equal to 2.5 mm of aluminium, while enamel is equal to 4 mm of aluminium. Internationally accepted standard for acceptable radiopacity is equal to 2 mm of aluminium. Amalgam has a radiopacity higher than 10 mm of aluminium which exceeds all the composite materials obtainable.

The color of a material is changed by the translucency or opacity of the material not only by the intensity and shade of the pigment or coloring agent. The body tissues vary in the degree of opacity that they exhibit. Most of them possess a degree of translucency. This is particularly true for tooth enamel and the soft supporting tissues neighboring the teeth. Earlier composites suffered from discoloration in one of three ways, including marginal discoloration, general surface discoloration, and bulk discoloration. Marginal discoloration is generally due to the presence of a marginal gap amid the restoration and the tooth tissues. Debris penetrates the gap and leads to an unsightly marginal stain; elimination of the marginal gap would completely avoid this type of staining. General surface discoloration may be related to the surface roughness of the composite and is more likely to occur with those composites employing large filler particles. Debris gets trapped in the spaces between the protruding filler particles and is not readily removed by tooth brushing. Polishing with a suitable abrasive should remove this surface stain.

The examples below are intended to further illustrate protocols for preparing and characterizing azole-functionalized silica nanoparticles and resin composites, and assessing the properties of the dental restoration formed by the cured resin composite. They are not intended to limit the scope of the claims.

Example 1

Synthesis of Silica Nanoparticles

Figure 19:
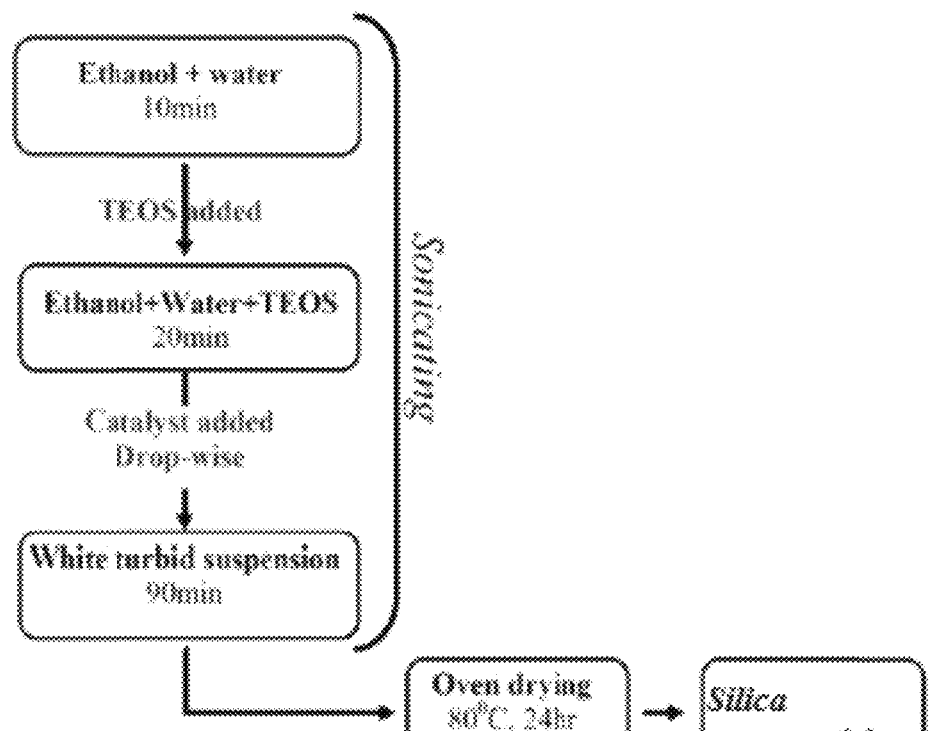
FIG. 19 is a flow diagram showing the synthesis of silica nanoparticles.
Figure 20:
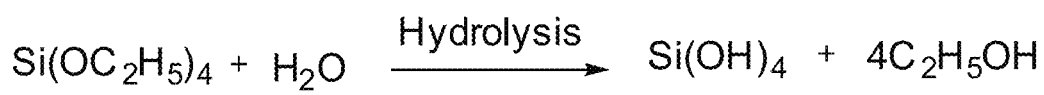
FIG. 20 is a synthetic scheme of silica nanoparticles.
Figure 20:
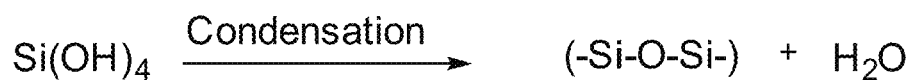
Figure 21:
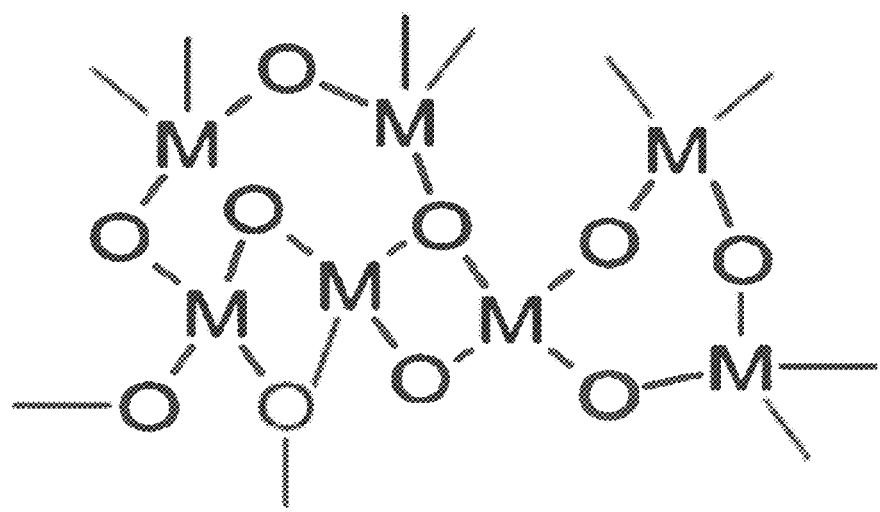
FIG. 21 shows three-dimensional cross-linked network structure of silica (M: Si).
Figure 22:
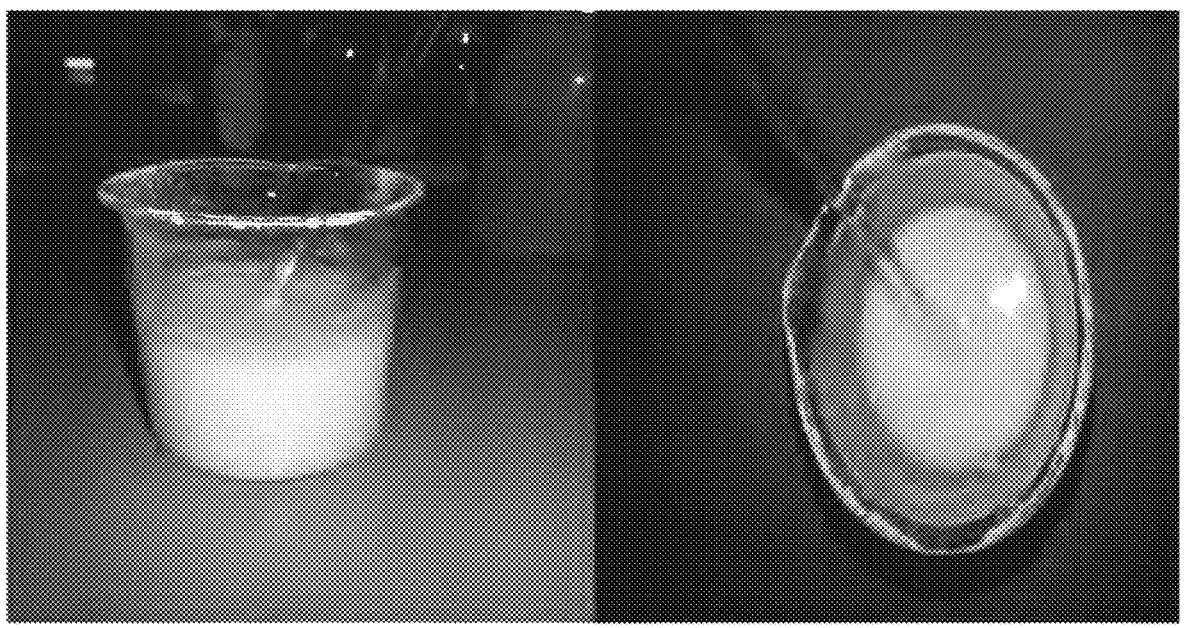
FIG. 22 shows pictures of gelatinous silica nanoparticles before vacuum drying.

To synthesize silica nanoparticles, TEOS was utilized as the starting material (Rahman, I., Vejayakumaran, P., Sipaut, C., Ismail, J., Bakar, M. A., Adnan, R., and Chee, C., "An optimized sol-gel synthesis of stable primary equivalent silica particles", Colloids and Surfaces A: Physicochemical and Engineering Aspects, vol. 294, pp. 102-110, 2007; Rao, K. S., El-Hami, K., Kodaki, T., Matsushige, K., and Makino, K., "A novel method for synthesis of silica nanoparticles", Journal of Colloid and Interface Science, vol. 289, pp. 125-131, 2005; and Stöber, W., Fink, A., and Bohn, E., "Controlled growth of monodisperse silica spheres in the micron size range", Journal of colloid and interface science, vol. 26, pp. 62-69, 1968, each incorporated herein by reference in their entirety). Synthesis of silica nanoparticles was carried out in a two-step procedure as shown in FIGS. 19 and 20. First, stoichiometric amount of ethanol and distilled water was mixed which was followed by the addition of TEOS to the mixture. Ethanol fastens the solubility of TEOS in the mixture. Second, ammonium hydroxide was added dropwise to the mixture to serve as a catalyst. The ratio of ethanol:water:TEOS:ammonium hydroxide used was 1:2:1:0.5 by weight. A gelatinous precipitate was formed during the addition of the catalyst. A formation of turbid suspension indicates the success of the reaction. To ensure uniform dispersity and obtain small size nanoparticles with a narrow size distribution, the process was conducted in an ultrasonicator to prevent particle aggregation and agglomeration. The white turbid suspension (FIGS. 21 and 22) was collected and dried in an oven at 80° C.

Example 2

Surface Modification of Silica Nanoparticles

Functionalization can be defined as the chemical reaction to treat and modify the surface of inorganic fillers to make them compatible with the organic polymer matrix of the composite. Modification of the surface of silica nanoparticles is required because these nanoparticles are very fine and can easily agglomerate. On the other hand, dispersion of nano-silica in organic solvents is difficult (Mohsen, N., and Craig, R., "Hydrolytic stability of silanated zirconia-silica-urethane dimethacrylate composites", Journal of Oral Rehabilitation, vol. 22, pp. 213-220, 1995, incorporated herein by reference in its entirety). Silica nanoparticles were surface-modified with (1) 1H-1,2,4-triazole (Tri-), (2) 3-amino-1,2,4-triazole (ATri-), (3) 5-aminotetrazole (Tet-), and (4) imidazole (Im-) after reaction with epichlorohydrin.

Figure 23:
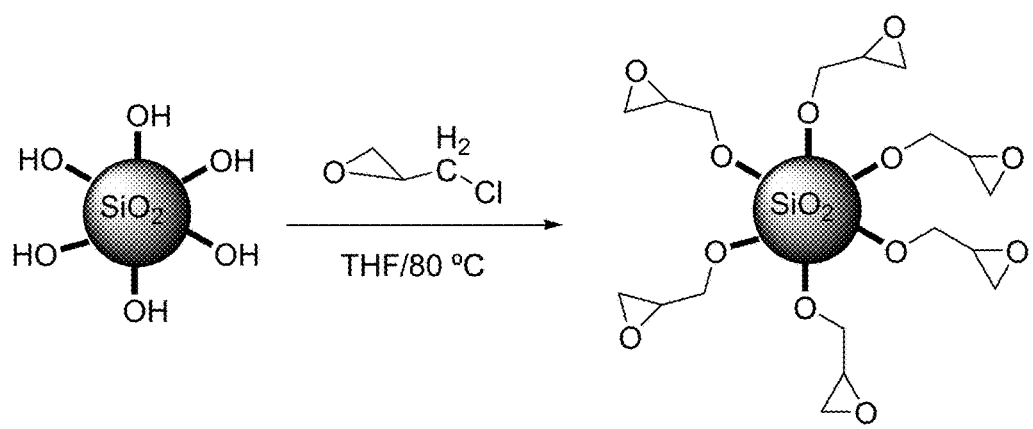
FIG. 23 shows the reaction of silica nanoparticles with epichlorohydrin.

(i) Reaction of Silica Nanoparticles with Epichlorohydrin (FIG. 23)

1 g of $SiO_2$ was dispersed in 10 mL THF, and 9 g of epichlorohydrin was added to solution. HCl gas was released which indicated that reaction had occurred between epichlorohydrin and the surface of silica. The modification ratio with epichloroydrin can be calculated by back titration method of the released HCl gas, which was bubbled to NaOH solution. The temperature was set at 50° C. After reaction completion, the modified nanosilica was collected and washed many times with a 1/4 ethanol/water mixture and dried in an oven at 80° C.

Figure 24:
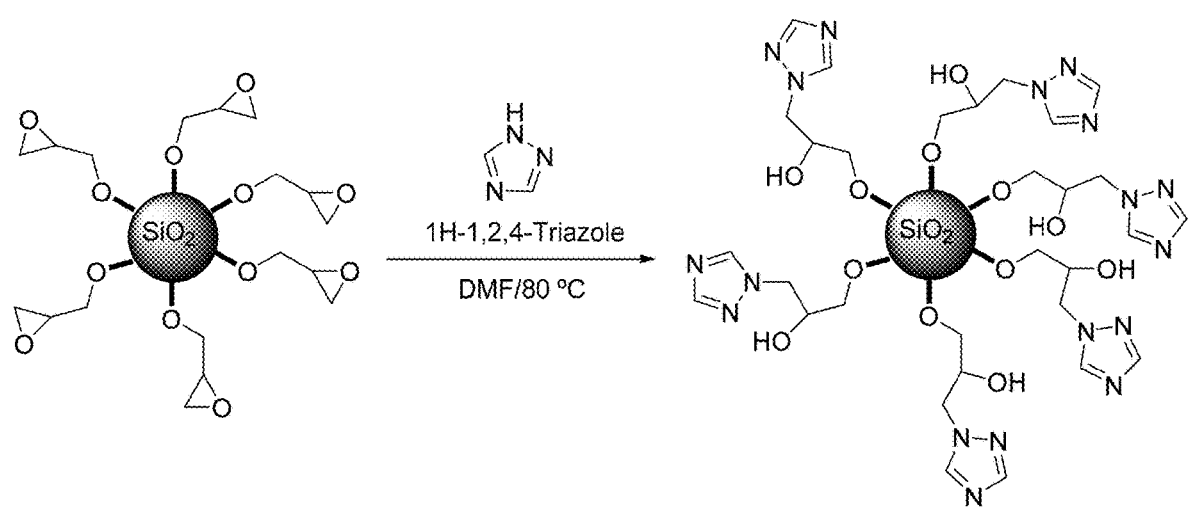
FIG. 24 shows the reaction of epoxy modified silica nanoparticle with 1H-1,2,4-triazole.

(ii) Modification with Triazole (FIG. 24)

To synthesize 1H-1,2,4-triazole functionalized nanosilica, modified epoxy silica nanoparticles was dispersed in 10 mL dimethylformamide (DMF) and an excess amount of 1H-1, 2,4-triazole was added to the reaction system, which was heated at a temperature of 80° C. The mixture was stirred under a nitrogen environment for 24 hrs. A solid mixture was formed which was collected and washed several times with a mixture of 1/4 ethanol/distilled water. This was done to remove unreacted starting materials. The solid mixture was then dried in an oven at 80° C.

Figure 25:
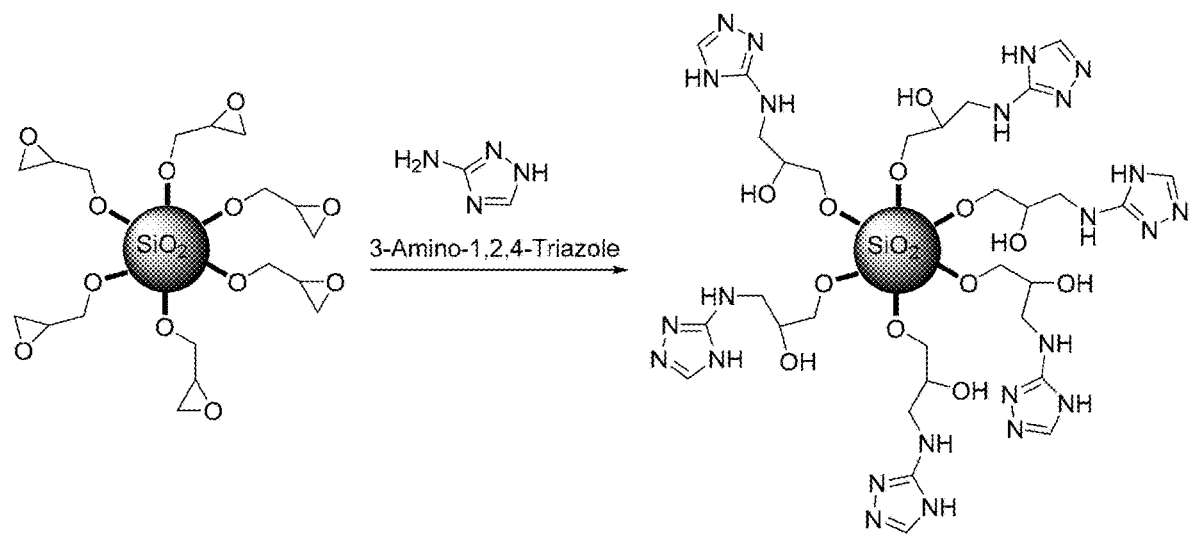
FIG. 25 shows the reaction of epoxy modified silica nanoparticles with 3-amino-1,2,4-triazole.

(iii) Modification with 3-Amino-1,2,4-Triazole (FIG. 25)

To synthesize 3-amino-1,2,4-triazole functionalized nanosilica, modified epoxy silica nanoparticles was dispersed in 10 mL dimethylformamide (DMF) and an excess amount of the 3-amino-1,2,4-triazole was added to the reaction system, which was heated at a temperature of 80° C. The mixture was stirred under a nitrogen environment for 24 hrs. A solid mixture was formed which was collected and washed several times with a mixture of 1/4 ethanol/distilled water. This was done to remove unreacted starting materials. The solid mixture was then dried in an oven at 80° C.

Figure 26:
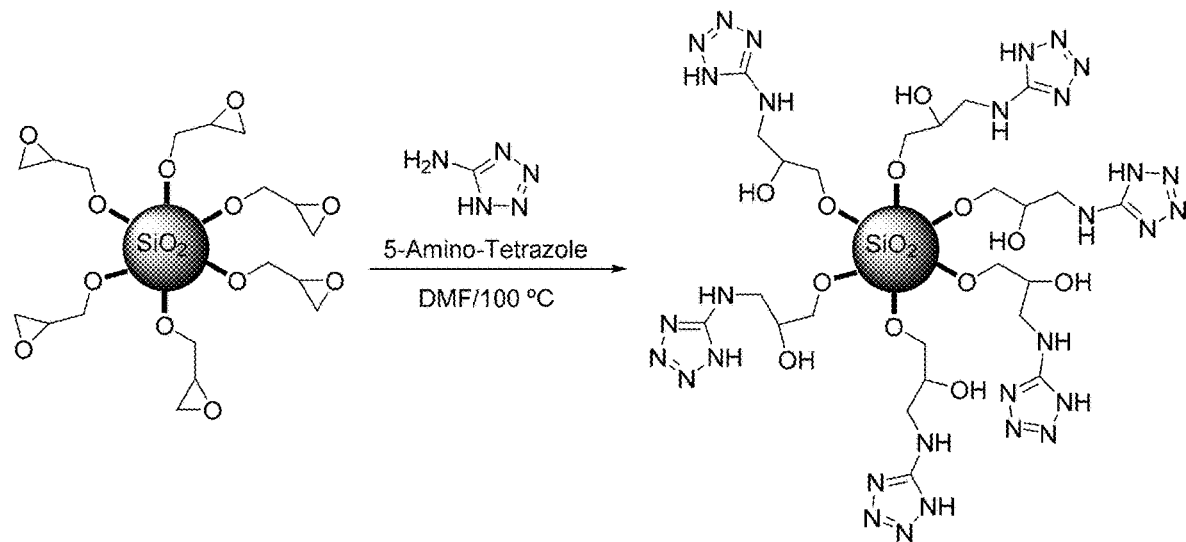
FIG. 26 shows the reaction of epoxy modified silica nanoparticles with 5-aminotetrazole.

(iv) Modification with 5-Amino-Tetrazole (FIG. 26)

To synthesize 5-amino-tetrazole functionalized nanosilica, modified epoxy silica nanoparticles was dispersed in 10 mL dimethylsulfuoxide (DMF) and an excess amount of the 5-amino-tetrazole was added to the reaction system, which was heated at a temperature of 100° C. The mixture was stirred under a nitrogen environment for 24 hrs. A solid mixture was formed which was collected and washed several times with a mixture of 1/4 ethanol/distilled water. This was done to remove unreacted starting materials. The solid mixture was then dried in an oven at 80° C.

Figure 27:
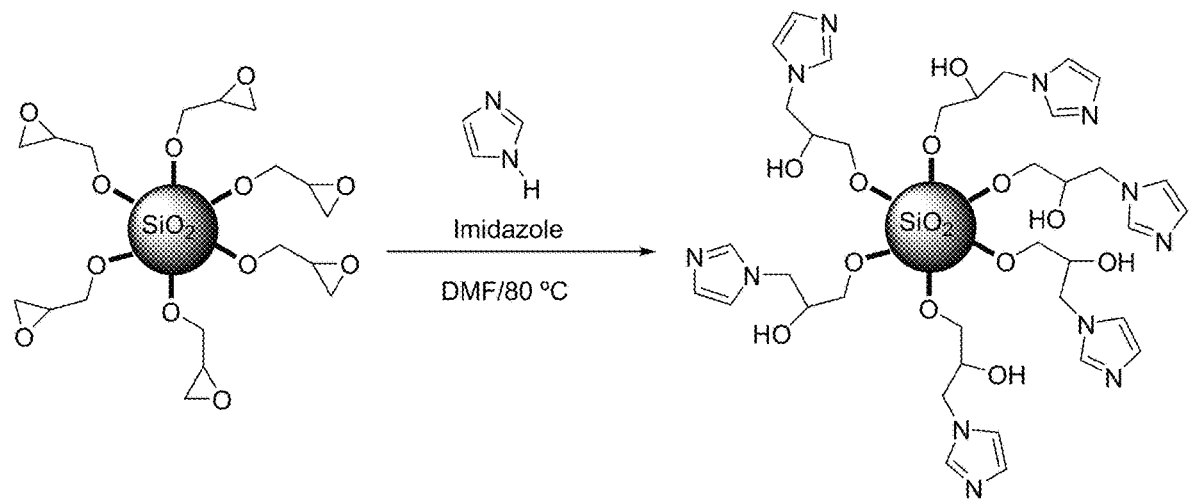
FIG. 27 shows the reaction of epoxy modified silica nanoparticles with imidazole.

(v) Modification with Imidazole (FIG. 27)

To synthesize imidazole functionalized nanosilica, modified epoxy silica nanopartiles was dispersed in 10 mL dimethylsulfuoxide (DMF) and an excess amount of imidazole was added to the reaction system, which was heated at a temperature of 80° C. The mixture was stirred under a nitrogen environment for 24 hrs. A solid mixture was formed which was collected and washed several times with a mixture of 1/4 ethanol/distilled water. This was done to remove unreacted starting materials. The solid mixture was then dried in an oven at 80° C.

Example 3

Preparation of Resin Composites

Nanocomposites were synthesized and named as series A1-A6, B1-B6, C1-C6 and D1-D6 (table 9 and 10). The naming was based on the types of functional nanoparticle used and the volume fraction of the functional nanoparticles. First, bis-GMA and TEGDMA (50:50 wt %) monomers were blended by stirring at a temperature of 500° C. Functionalized silica nanoparticles were added at different weight percentages (10-60 wt %). The mixing was done by stirring and mixing by a spatula for about 30 min until a homogenous mixture was obtained. Second, the initiator/co-initiator system of CQ (0.01 wt %) and EDMAB (0.04 wt %) was added to the homogenous mixture by continuous stirring until a transparent paste was obtained. The paste was casted in a Teflon mold. A curing LED light source was used to irradiate the paste for 60 seconds for each formulation.

TABLE 9

Different formulations of resin composites series A and B.

| Nanoparticles-type | wt % | Series | Nanoparticles-type | wt % | Series |
|---|---|---|---|---|---|
| 1H-1,2,4-triazole functional silica nanoparticles | 10 | A1 | 3-amino-1,2,4-triazole functional silica nanoparticles. | 10 | B1 |
| | 20 | A2 | | 20 | B2 |
| | 30 | A3 | | 30 | B3 |
| | 40 | A4 | | 40 | B4 |
| | 50 | A5 | | 50 | B5 |
| | 60 | A6 | | 60 | B6 |

TABLE 10

Different formulations of resin composites series C & D.

| Nanoparticles-type | wt % | Series | Nanoparticles-type | wt % | Series |
|---|---|---|---|---|---|
| 5-aminotetrazole functional silica nanoparticle | 10 | C1 | Imidazole functional silica nanoparticles | 10 | D1 |
| | 20 | C2 | | 20 | D2 |
| | 30 | C3 | | 30 | D3 |
| | 40 | C4 | | 40 | D4 |
| | 50 | C5 | | 50 | D5 |
| | 60 | C6 | | — | — |

Example 4

Compressive Strength (i) Specimen Preparation

Figure 28A:
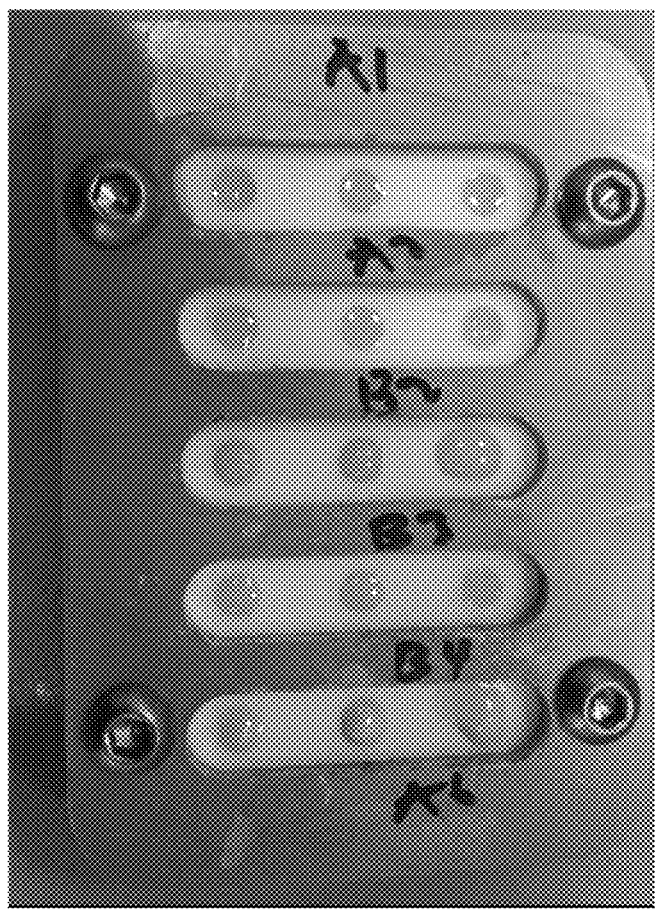
FIG. 28A is a picture showing a Teflon mold (5 mm diameter×3 mm height) containing different formulations of composite paste.
Figure 28B:
FIG. 28B is a picture showing the curing process of a resin composite.
Figure 28C:
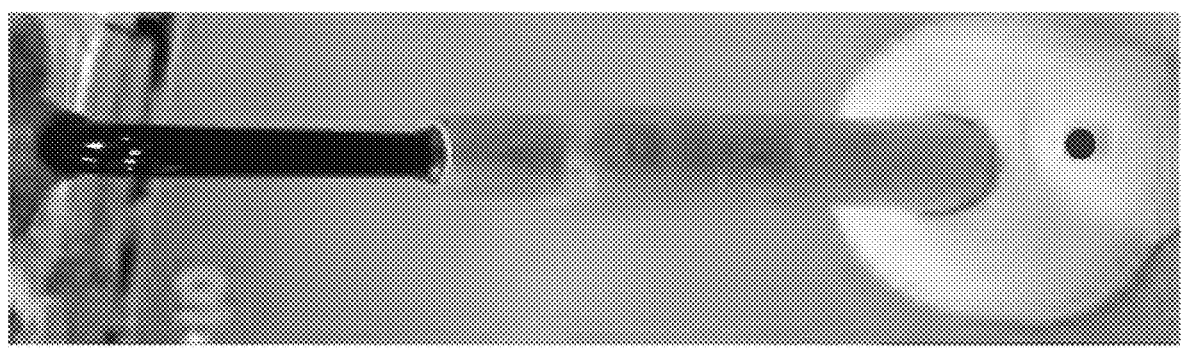
FIG. 28C is a picture showing the LED curing light (power density=1000 mW/cm$^2$, wavelength=450-500 nm).

Cylindrical specimens (n=3) with 5 mm in diameter and 3 mm in height were prepared by using a Teflon mold (FIGS. 28A-C). LED curing light was irradiated on the surface of the casted paste for 60 s. A rigid material was obtained for all formations.

(ii) Compressive Strength Test

Figure 29:
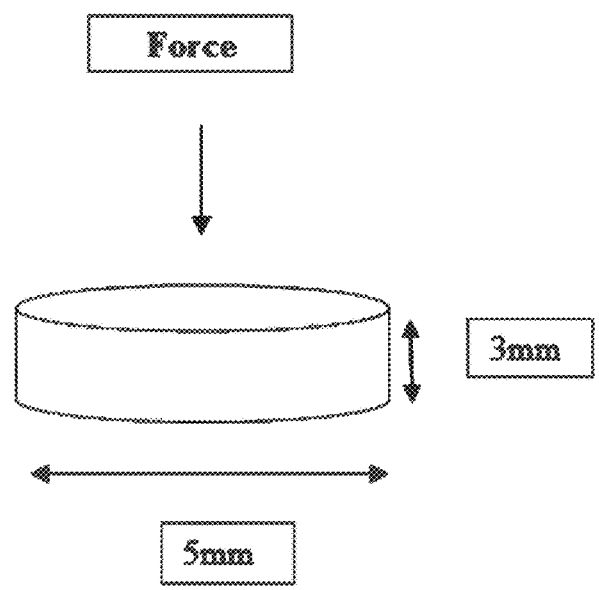
FIG. 29 is a schematic diagram of a specimen in the compressive strength test.
Figure 30:
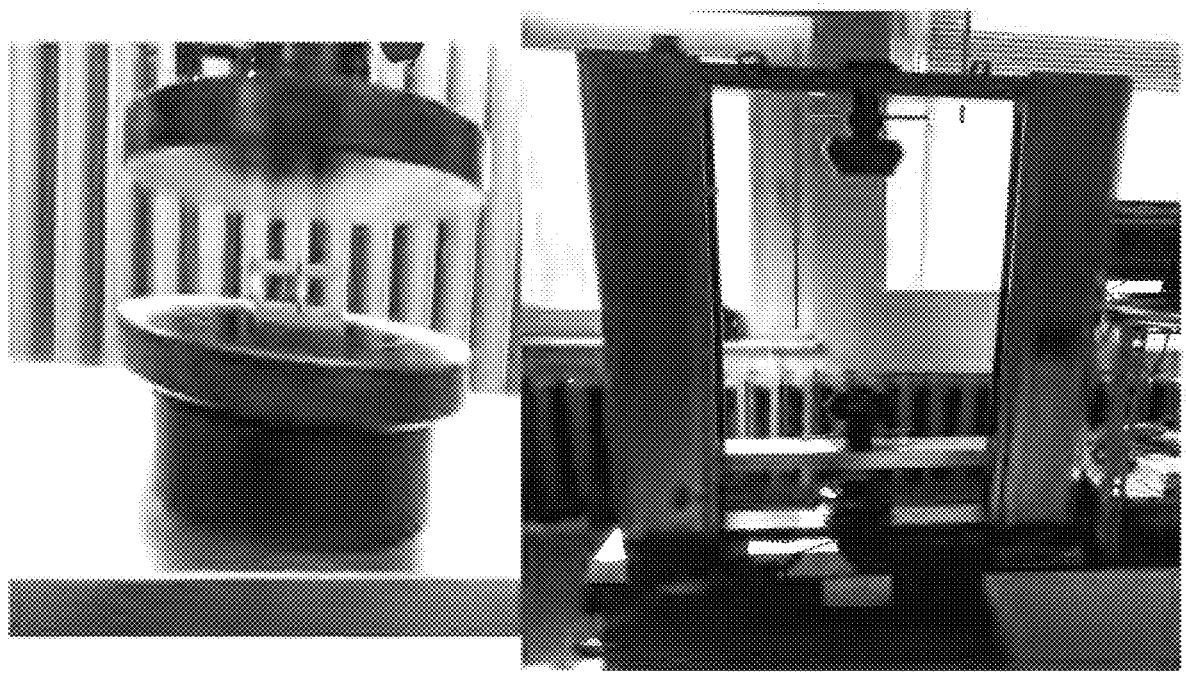
FIG. 30 shows pictures of a universal testing machine and load applied on the composite.

Mechanical properties of the disc-shaped specimens with 5 mm in diameter and 3 mm in thickness were tested in a universal testing machine (FIGS. 29 and 30) by using a compression fixture. The upper and bottom surfaces of test specimens were properly and gently polished, and then placed onto metal plates. Then, the testing fixture was moved to a particular or initial gap by applying a small compression force onto the sample. The speed of cross-head was 0.1 mm/min. Stress (MPa)-strain (%) curves were recorded and the mechanical parameters of "Young's modulus (E)", "compression strength or maximum stress" and "strain at break or failure" were determined. For each composition, three specimens were tested and average values were reported with the standard deviation.

Evaluation of compressive strength was done by comparing the diameter of the specimen to the peak load by using the following formula: F/A, in which F is the force at failure point, and A is the cross sectional area.

Example 5

Mechanical Analysis

Table 11-14 and FIGS. 58A, 59A, 60A and 61A show that composite D1 has the highest compression strength mean value of 408±29 MPa, while composites C1, B1, blank and A1 have a compression strength of 318±50 MPa, 303.5±58.7 MPa, 253±66 MPa, and 241±33.3 MPa, respectively. Composite C1 has the highest elastic modulus of 9.71869±0.87 GPa, followed by D1 of 8.22802±0.39 GPa, B3 of 5.66365±0.42 GPa, blank of 5.37±1.1 GPa, and A4 of 4.4628 f 0.89 GPa (FIGS. 58C, 59C, 60C and 61C). Conventional dental composites which are filled with hybrid fillers have elastic modulus and compression strength in the range of 5 to 10 GPa, and 150 to 250 MPa, respectively (Cramer, N. B., Couch, C. L., Schreck, K. M., Carioscia, J. A., Boulden, J. E., Stansbury, J. W., and Bowman, C. N., "Investigation of thiol-ene and thiol-ene-methacrylate based resins as dental restorative materials", dental materials, vol. 26, pp. 21-28, 2010; Leprince, J., Palin, W., Mullier, T., Devaux, J., Vreven, J., and Leloup, G., "Investigating filler morphology and mechanical properties of new low-shrinkage resin composite types", Journal of oral rehabilitation, vol. 37, pp. 364-376, 2010; Samuel, S. P., Li, S., Mukherjee, I., Guo, Y., Patel, A. C., Baran, G., and Wei, Y., "Mechanical properties of experimental dental composites containing a combination of mesoporous and nonporous spherical silica as fillers", dental materials, vol. 25, pp. 296-301, 2009; and Wang, H I., Zhu, M., Li, Y., Zhang, Q., and Wang, H I., "Mechanical properties of dental resin composites by co-filling diatomite and nanosized silica particles", Materials Science and Engineering: C, vol. 31, pp. 600-605, 2011, each incorporated herein by reference in their entirety). These mean compression strength values for currently disclosed composites show a considerable enhancement in mechanical properties when compared to dental composites containing hybrid fillers.

TABLE 11

Mean and standard deviation values of compression strength, strain at break and Elastic Modulus for blank & A composites series.

| Composites A | Filler fraction (wt %) | Compression strength (MPa) | Strain at break (GPa) | Elastic modulus (GPa) |
|---|---|---|---|---|
| A$_0$(blank) | 0 | 253 ± 66 | 5.975 ± 0.08 | 5.37 ± 1.1 |
| A1 | 10 | 241 ± 33.3 | 5.98 ± 1.06 | 2.92333 ± 0.30 |
| A2 | 20 | 189.33 ± 18.34 | 6.68 ± 0.35 | 3.57068 ± 0.83 |
| A3 | 30 | 141.33 ± 15.31 | 7.67 ± 1.67 | 2.50474 ± 0.13 |
| A4 | 40 | 138.67 ± 21.13 | 5.13 ± 0.42 | 4.4628 ± 0.89 |
| A5 | 50 | 136 ± 18.25 | 6.17 ± 0.97 | 3.71468 ± 1.01 |
| A6 | 60 | 67 ± 14.14 | 6.85 ± 0.64 | 4.00 ± 1.36 |

TABLE 12

Mean and standard deviation values of compression strength, strain at break and Elastic Modulus for blank & B composites series.

| Composites B | Filler fraction (wt %) | Compression strength (MPa) | Strain at break (GPa) | Elastic modulus (GPa) |
|---|---|---|---|---|
| B$_0$(blank) | 0 | 253 ± 66 | 5.98 ± 0.1 | 5.37 ± 1.1 |
| B1 | 10 | 303.5 ± 58.7 | 5.45 ± 0.23 | 5.63 ± 0.35 |
| B2 | 20 | 267.33 ± 38.1 | 5.53 ± 0.31 | 2.9 ± 0.46 |
| B3 | 30 | 222.7 ± 21.13 | 5.67 ± 0.15 | 5.66365 ± 0.42 |
| B4 | 40 | 155 ± 12.5 | 6.33 ± 0.12 | 4.41126 ± 0.58 |
| B5 | 50 | 135.33 ± 5.5 | 6.9 ± 0.78 | 2.18103 ± 0.76 |
| B6 | 60 | 55 ± 9.85 | 5.41 ± 1.07 | 2.18164 ± 0.57 |

TABLE 13

Mean and standard deviation values of compression strength, strain at break and Elastic Modulus for blank & C composites series.

| Composites C | Filler fraction (wt %) | Compression strength (MPa) | Strain at break (GPa) | Elastic modulus (GPa) |
|---|---|---|---|---|
| C$_0$(blank) | 0 | 253 ± 66.00 | 5.98 ± 5.98 | 5.37 ± 1.1 |
| C1 | 10 | 318 ± 50.00 | 6.1 ± 6.10 | 9.71869 ± 0.87 |
| C2 | 20 | 302 ± 0.00 | 7 ± 7.00 | 6.63657 ± 0.75 |
| C3 | 30 | 228 ± 52.00 | 7 ± 7.00 | 4.63185 ± 1.28 |
| C4 | 40 | 156 ± 14.00 | 8.55 ± 8.55 | 3.94148 ± 0.55 |
| C5 | 50 | 104 ± 13.00 | 7 ± 7.00 | 2.88571 ± 0.27 |
| C6 | 60 | 60 ± 5.00 | 6.03 ± 6.03 | 1.26866 ± 0.22 |

TABLE 14

Mean and standard deviation values of compression strength, strain at break and Elastic Modulus for blank & D composites series.

| Composites D | Filler fraction (wt %) | Compression strength (MPa) | Strain at break (GPa) | Elastic modulus (GPa) |
|---|---|---|---|---|
| D$_0$(blank) | 0 | 253 ± 66 | 5.98 ± 0.10 | 5.37 ± 1.1 |
| D1 | 10 | 408 ± 29 | 6.53 ± 0.52 | 8.22802 ± 0.39 |

TABLE 14-continued

Mean and standard deviation values of compression strength, strain at break and Elastic Modulus for blank & D composites series.

| Composites D | Filler fraction (wt %) | Compression strength (MPa) | Strain at break (GPa) | Elastic modulus (GPa) |
|---|---|---|---|---|
| D2 | 20 | 271 ± 13 | 9.12 ± 0.67 | 3.03495 ± 0.63 |
| D3 | 30 | 87 ± 15 | 12.1 ± 1.00 | 0.62319 ± 0.05 |
| D4 | 40 | 85 ± 26 | 11.5 ± 11.5 | 1.21554 ± 0.49 |
| D5 | 50 | 48.5 ± 5 | 8.57 ± 8.57 | 0.44452 ± 0.20 |

Example 6

Solubility and Sorption

Before solubility and sorption test, cured composite samples were kept in an oven at 37° C. to dry for 24 hrs. These samples were further placed in desiccators to dry for 2 hrs. For each formulation composition, dried samples were measured continuously till a constant mass m° was observed. Samples were immersed in water in separate sample bottles and kept in oven at 37° C. for 3 weeks before taken out and rinsed with water.

The water on the surface of the specimen was gently wiped out till there is no visible moisture. These samples were waved in air for 15 seconds and then weighed. For all the samples the mass (m) were recorded. These samples were again kept in the desiccators to dry following the same cycle as mention above at the temperature of 58° C. The specimen was weighed again and the mass ($m^2$) was obtained. To obtain a constant mass for each test sample, the above steps were repeated accordingly. These procedures were carried out to investigate water sorption (A) and water solubility (S) of the dental composite material based on the oysaed & Ruyter formula, which is given as $A=(m^1-m^2)/V$ and $S=(m^0-m^2)/V$, in which $m^0$ is the sample weight before immersion, $m^1$ is the sample weight after immersion, $m^2$ is the sample weight after immersion and desiccation, and V is the volume of the specimen in cubic millimeters. Data were analyzed by comparing mean values in sorption and solubility of different composite groups.

Example 7

Sorption and Solubility Analysis

As shown in table 15 and 16 and FIGS. 50A-B, 51A-B, 52A-B, and 53A-B, the analysis of the series of composites indicates an increase in both sorption and solubility of the composite as the amount of functional nanoparticle increases. Composite series D shows the least water sorption and solubility values after storage in water in an oven at 37° C. for 3 weeks. Composites A, B and C show similar water sorption and solubility values with different amounts of functional nanoparticles.

TABLE 15

Sorption values of composites series after 3 weeks storage in water at 37° C.

| A SERIES (mg/mm³) | B SERIES (mg/mm³) | C SERIES (mg/mm³) | D SERIES (mg/mm³) |
|---|---|---|---|
| 0.072 | 0.058 | 0.054 | 0.014 |
| 0.088 | 0.083 | 0.043 | 0.018 |
| 0.123 | 0.092 | 0.069 | 0.025 |
| 0.148 | 0.154 | 0.161 | 0.050 |
| 0.138 | 0.197 | 0.315 | 0.077 |
| 0.376 | 0.333 | 0.354 | |

TABLE 16

Solubility values of composites series after 3 weeks storage in water at 37° C.

| A SERIES (mg/mm³) | B SERIES (mg/mm³) | C SERIES (mg/mm³) | D SERIES (mg/mm³) |
|---|---|---|---|
| 0.052 | 0.032 | 0.045 | 0.040 |
| 0.099 | 0.082 | 0.004 | 0.006 |
| 0.068 | 0.078 | 0.034 | 0.103 |
| 0.138 | 0.214 | 0.153 | 0.123 |
| 0.257 | 0.351 | 0.416 | |

Example 8

Cytotoxicity Assay

Dental composites were casted in the form of discs by using a Teflon-based mold containing wells of 3 mm in thickness and 5 mm in diameter. The control samples used in the same measurements were made of the Teflon mold as well. In the tissue culture hood, the discs were sterilized for 20 minutes with UV light and then transferred into 15 mL conical tubes. The specimens were later washed using 70% ethanol and deionized water, and left to dry in the hood for 5 minutes. Each disc was then placed into individual wells of a 24-well plate and pre-incubated in 1 mL of DMEM for 15 minutes.

HepG2 cells (ATCC) seeded at 1×105 cells/well in a 24-well plate containing DMEM supplemented with 4.5 g/L glucose, 10% FBS, 2 mM L-glutamine, 100 U/mL penicillin, and 100 µg/mL streptomycin were pre-incubated overnight at 37° C. with 5% $CO_2$. The cells were then added to the discs of various formulations and incubated for 24 hours.

After incubation, all wells were washed with 500 µL of 1×PBS and incubated with 0.3 mg/mL of MTT (3-(4,5-dimethylthiazol-2-yl)-2,5-diphenyltetrazolium bromide) in 1×PBS at 37° C. for 3 hours. The resulting formazan crystals were solubilized by removing MTT solution and adding 450 µL of DMSO. The absorbance at 570 nm was measured by a spectrophotometer (Thermo Scientific).

Example 9

Cytotoxicity Analysis

Cytotoxicity analysis of various formulations reveals potently toxic and safe candidates. Potent cytotoxicity are complete absence of cytotoxicity are equally useful in different applications of dental composites. To investigate in vitro cytotoxic potential of presently disclosed silica nanoparticle-based dental composites, each of freshly synthesized composites was prepared in the shape of a disc using a mold of 5 mm in diameter and 3 mm in thickness and incubated with HepG2 cells. Assessment of cellular viability was done using a MIT assay followed by 24 hrs cell incubation of each formulation with increasing concentration of functionalized silica nanoparticles. Controls were prepared by using the same-size discs of the Teflon mold. It was observed that formulation A-1/hBN, and formulations D-1 through D-5 are nontoxic, formulations A1, A2, A3, B1 through B4, and C1 through C4 are moderately toxic, and formulations A4, A5, A6, B5, B6, C5, and C6 are very toxic compared to the controls (FIGS. 54-57).

Example 10

X-Ray Diffraction (XRD)

XRD was utilized to characterize the structure and composition of the functionalized filler nanoparticles. Each material has its own XRD pattern caused by diffraction of an incident X-ray beam when it interferes with the atomic planes of a crystal. Crystal structures of elements, unknown materials or mixtures can be identified by XRD comparing the experimental data with databases (Langford, J. I., and Louer, D., "Powder diffraction", Reports on Progress in Physics, vol. 59, p. 131, 1996, incorporated herein by reference in its entirety). XRD patterns of $SiO_2$ nanoparticles vary based on their crystal structures. Each pattern results from interaction between the incident X-rays and the sample creating diffraction beams. These diffracted beams are related to inter-planar spacing (d-space) in a crystalline powder. According to Bragg's Law: $A=2d \sin \theta$ in which A is the wavelength of X-rays (Å), d is the inter-planar spacing (Å), and $\theta$ is the diffraction angle (degrees). X-ray powder diffraction (XRD) patterns were conducted by a X-ray diffraction instrument, Rigaku Smart Lab Diffractometer, operated at 40 kV and 35 mA using Cu K $\alpha$ radiation.

Example 11

Energy Dispersive X-Ray Spectroscopy (EDX)

EDX is a common analytical method used in elemental chemical analysis. It depends on the interaction between X-rays and a sample. Each element has a characteristic atomic structure which results in a unique set of peaks.

Example 12

EDX Analysis

EDX analysis reports the elemental analysis (weight % and atomic %) of each functional nanoparticles used herein. FIGS. 46-49 also confirm the modification of silica nanoparticles with azoles units.

Example 13

Fourier-Transform Infrared Spectroscopy (FT-IR)

Confirmation of bonding between silica nanoparticles and different azole units via different functional groups was done by FT-IR spectroscopy. Determination of the existence of functional groups in molecules was also conducted by comparing the experimental FT-IR absorbance or transmission peaks with databases. When new fillers are introduced to a composite, FT-IR is a valuable method in evaluating the functional groups that bind the fillers with polymer matrix. Many studies were conducted in literature to understand bonding between functionalized fillers and resin matrix. All samples were dried under vacuum and stored in a glove box before FT-IR analysis. FT-IR spectra with the range of 4000-400 $cm^{-1}$ and a resolution of 4 $cm^{-1}$ were recorded with an ATR system of Bruker Alpha-P.

Example 14

FT-IR Analysis
(i) Functionalized Fillers

Figure 31:
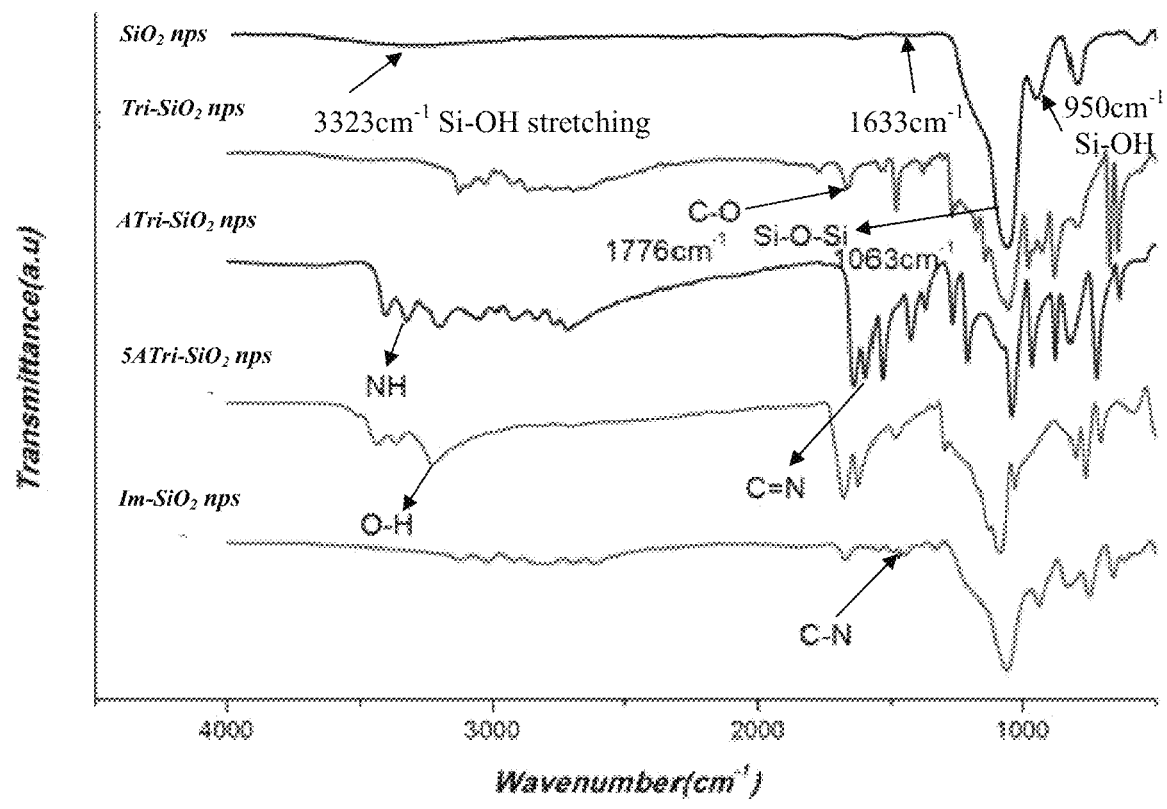
FIG. 31 is an overlay of FT-IR spectra of the silica nanoparticles, Tri-SiO$_2$ nanoparticles, ATri-SiO$_2$ nanoparticles, Tet-SiO$_2$ nanoparticles, and Im-SiO$_2$ nanoparticles.
Figure 32:
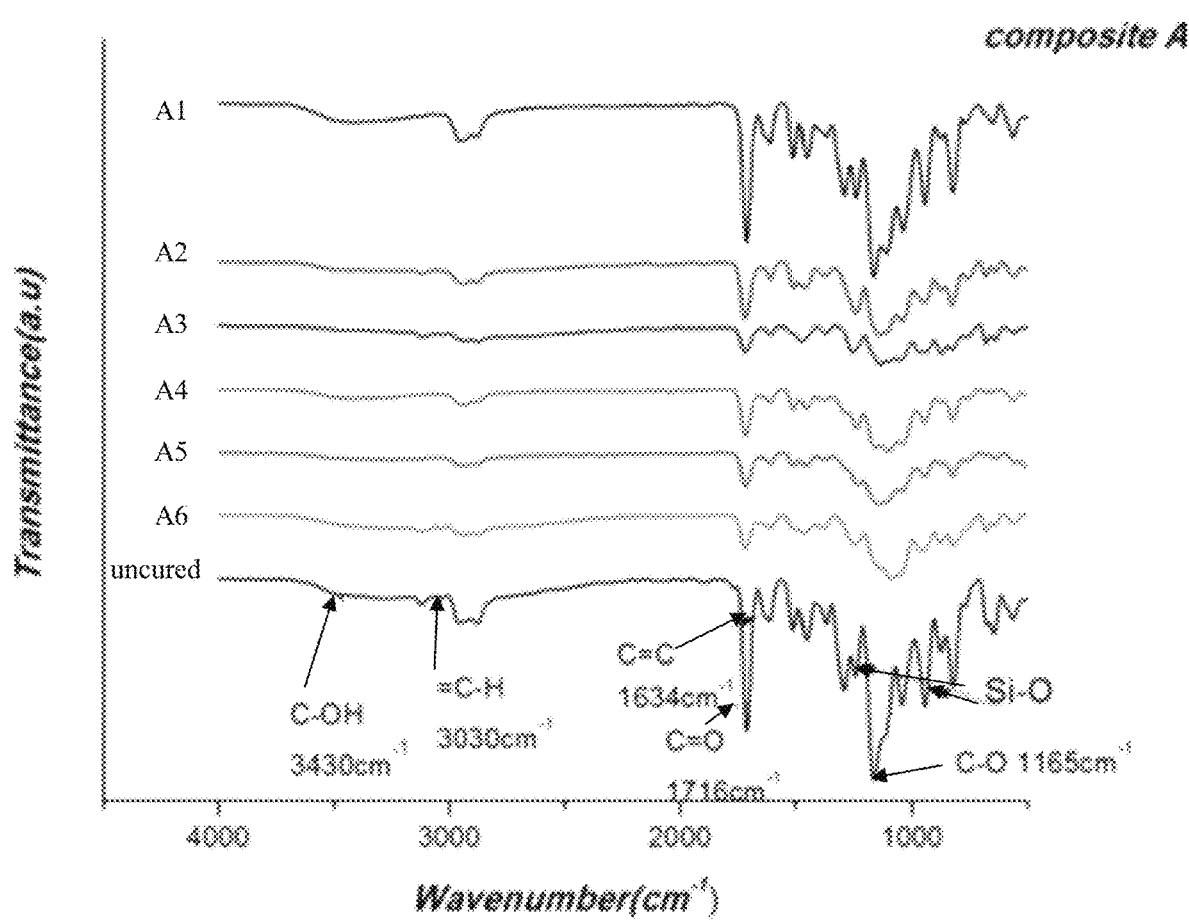
FIG. 32 is an overlay of FT-IR spectra of composite A series and an uncured sample.
Figure 33:
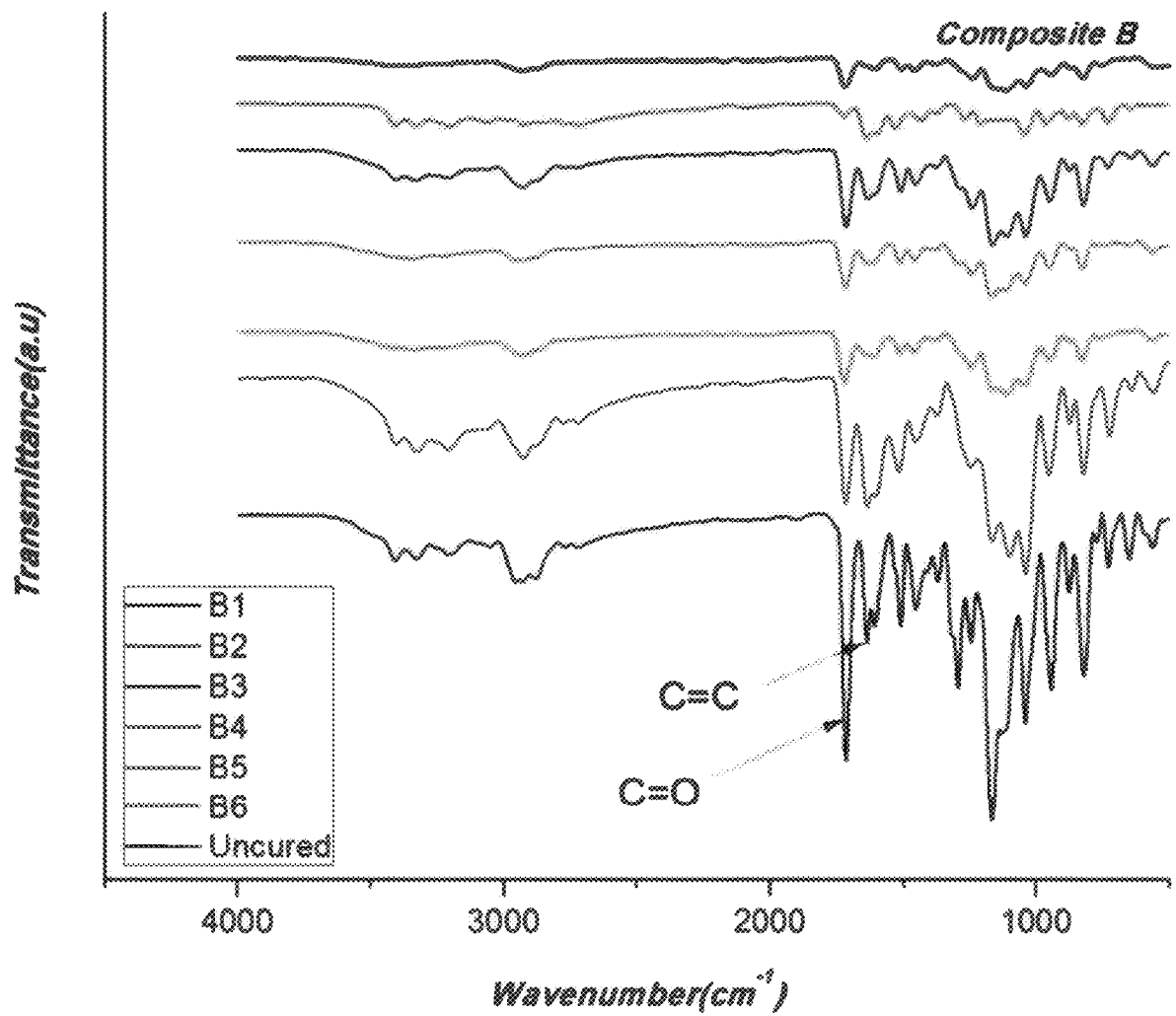
FIG. 33 is an overlay of FT-IR spectra of composite B series and an uncured sample.
Figure 34:
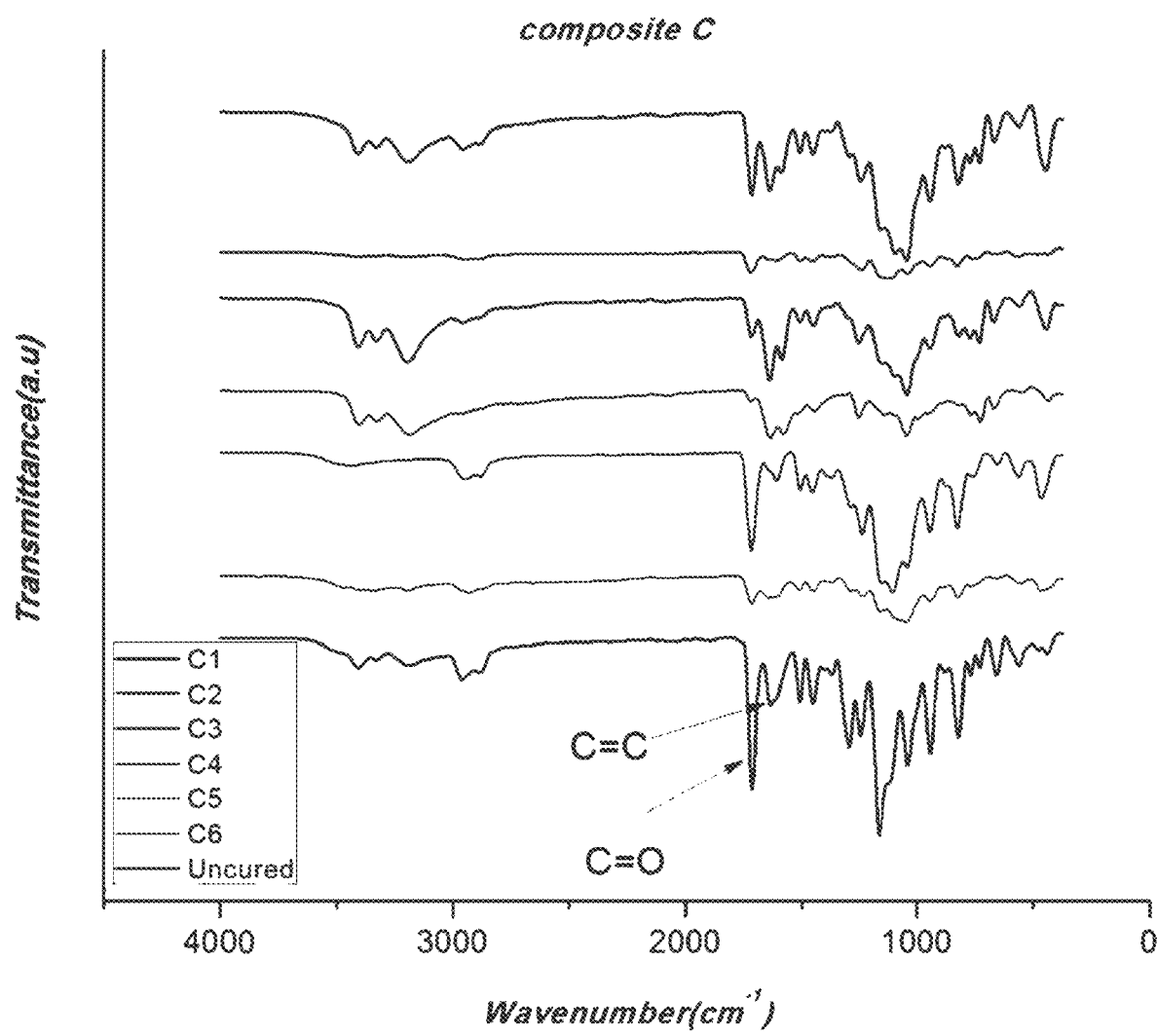
FIG. 34 is an overlay of FT-IR spectra of composite C series and an uncured sample.
Figure 35:
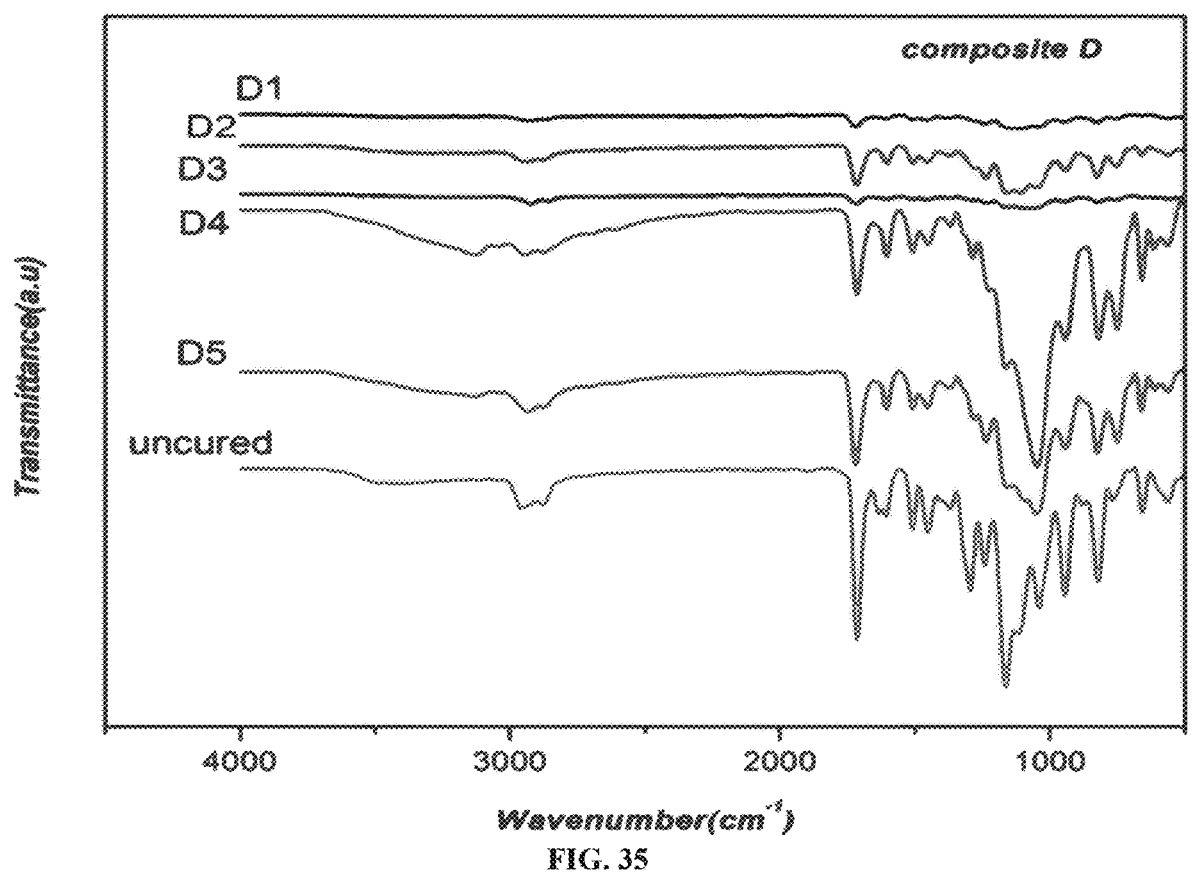
FIG. 35 is an overlay of FT-IR spectra of composite D series and an uncured sample.
Figure 36A:
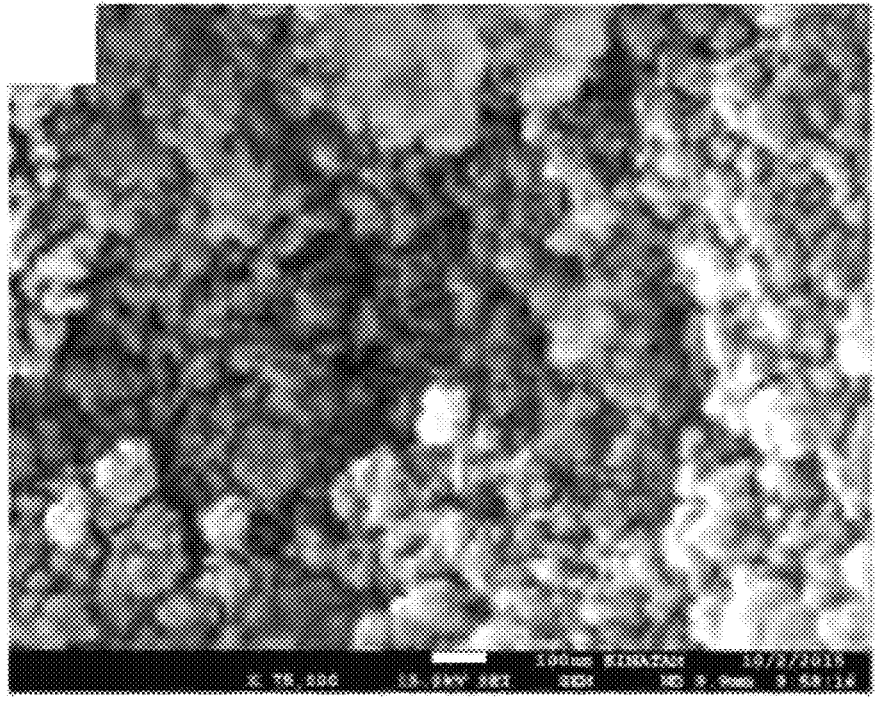
FIG. 36A is a scanning electron microscope (SEM) micrograph of the silica nanoparticles.
Figure 36B:
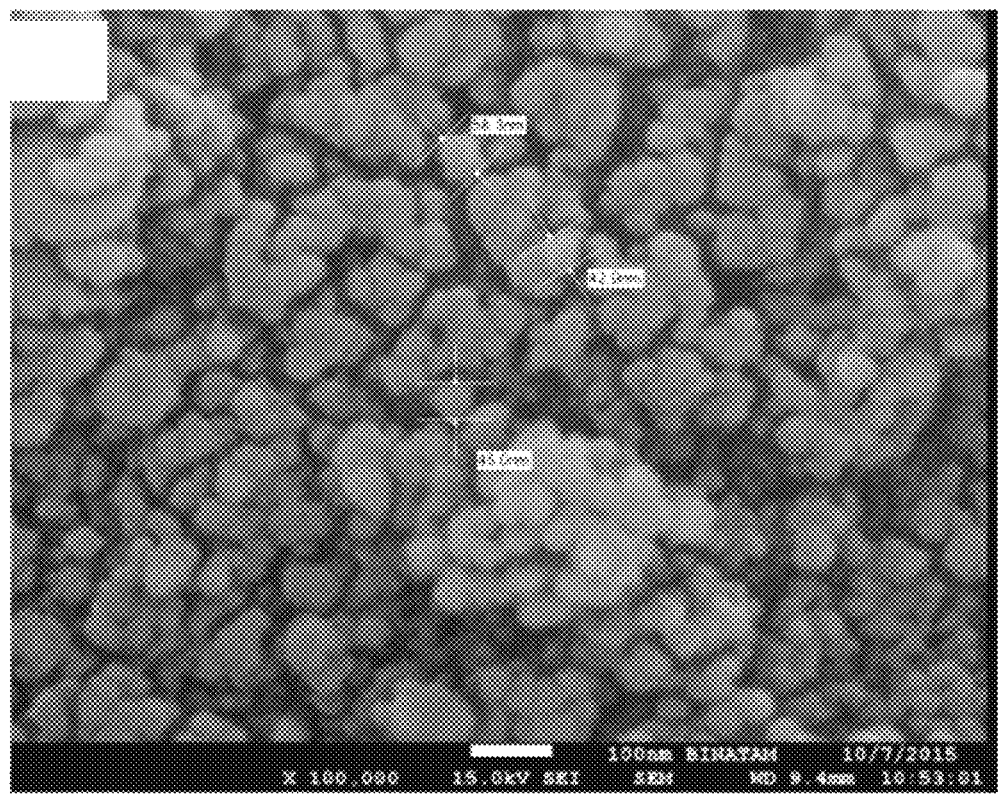
FIG. 36B is a SEM micrograph of the epoxy modified silica nanoparticles.
Figure 36C:
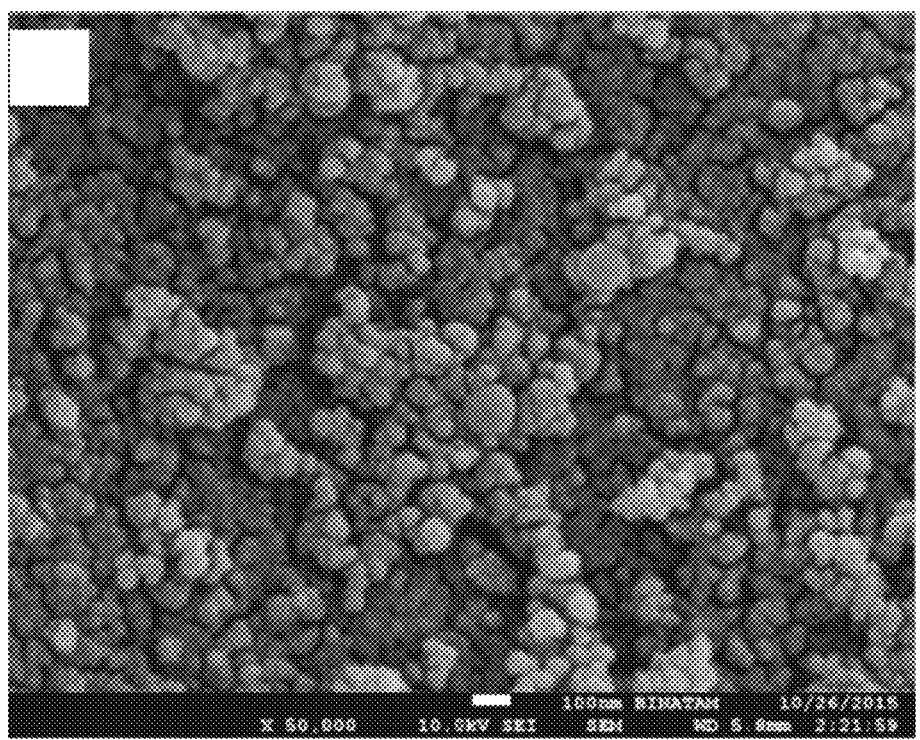
FIG. 36C is a SEM micrograph of Tri-SiO$_2$ nanoparticles.
Figure 36D:
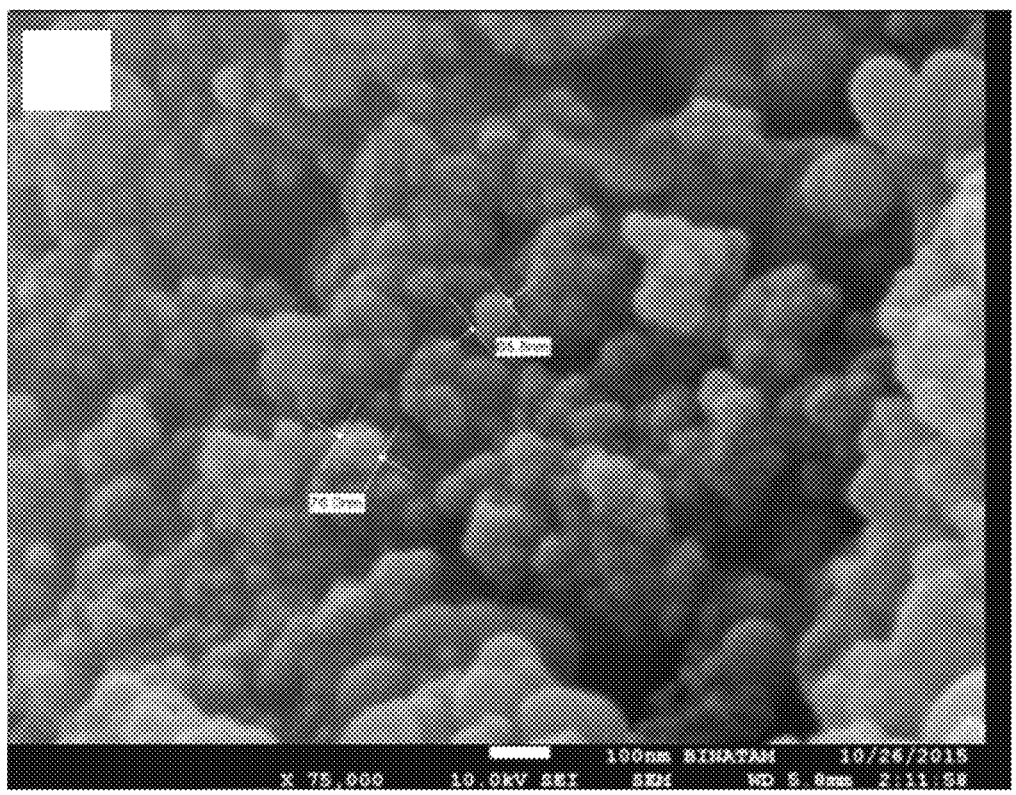
FIG. 36D is a SEM micrograph of ATri-SiO$_2$ nanoparticles.
Figure 36E:
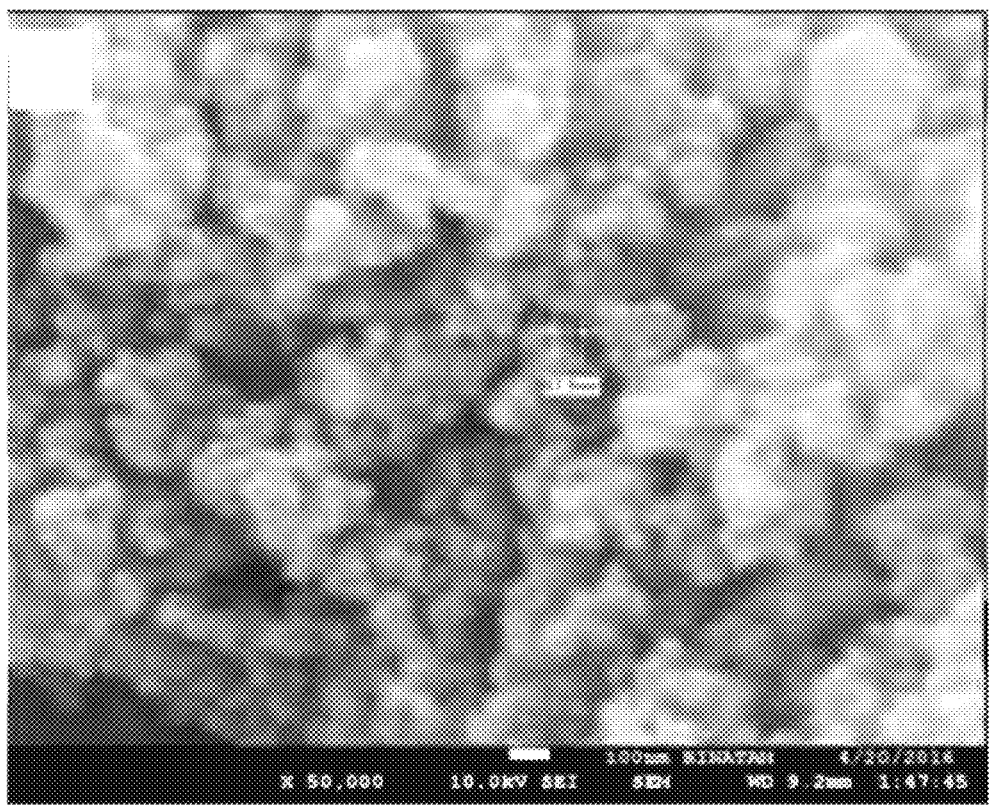
FIG. 36E is a SEM micrograph of Tet-SiO$_2$ nanoparticles
Figure 36F:
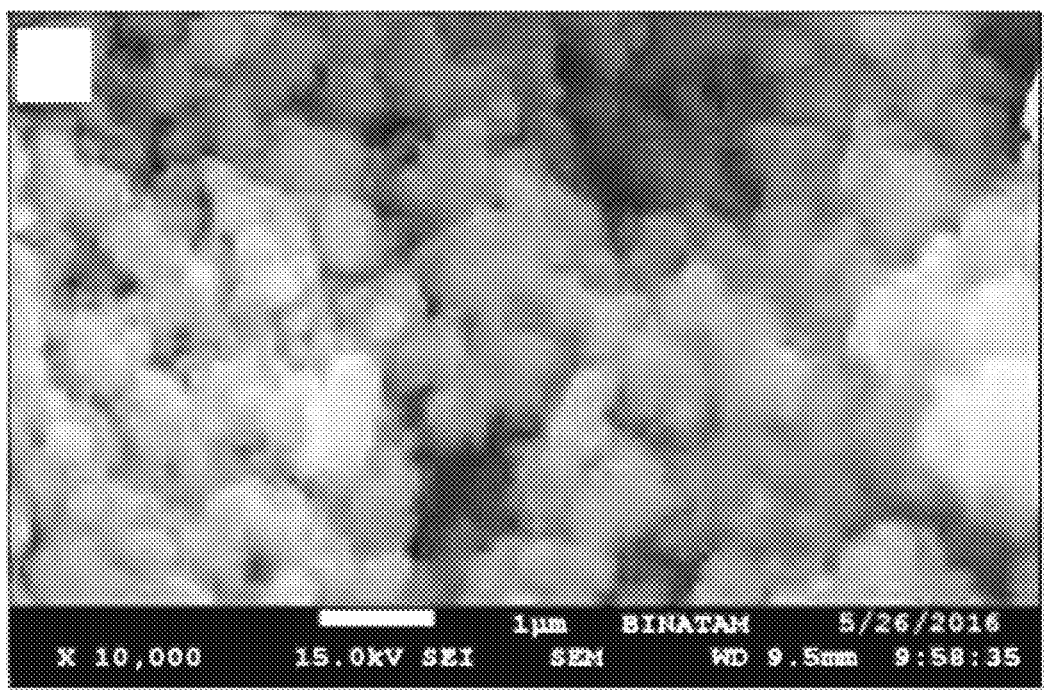
FIG. 36F is a SEM micrograph of Im-SiO$_2$ nanoparticles.
Figure 37A:
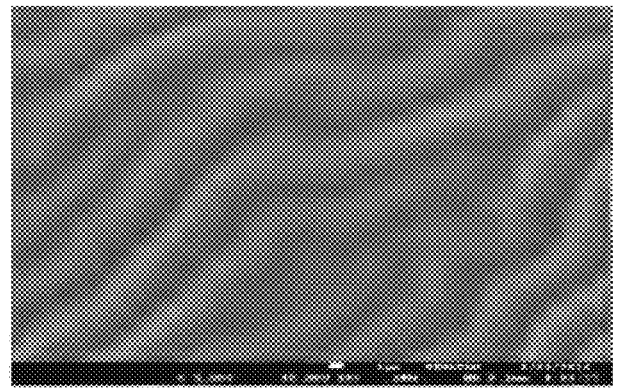
FIG. 37A shows a SEM image of a fractured surface of composites A series.
Figure 37B:
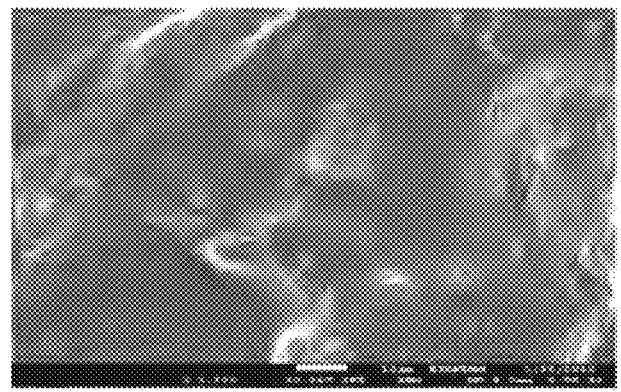
FIG. 37B shows a SEM image of a fractured surface of composites A series.
Figure 37C:
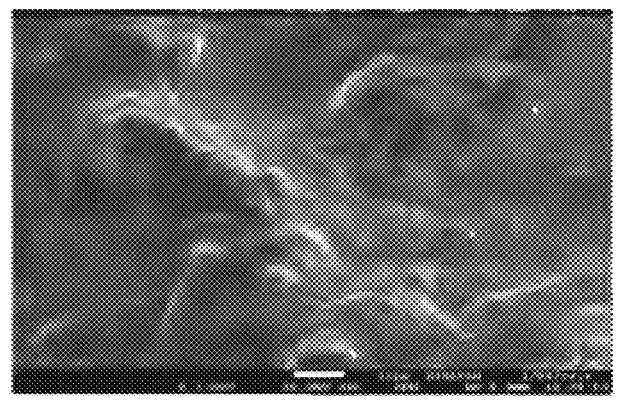
FIG. 37C shows a SEM image of a fractured surface of composites A series.
Figure 37D:
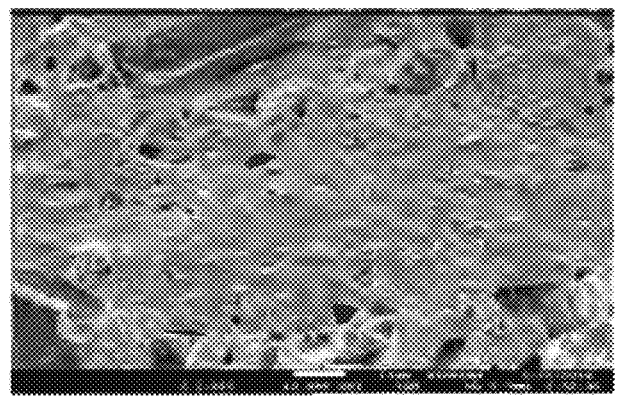
FIG. 37D shows a SEM image of a fractured surface of composites A series.
Figure 37E:
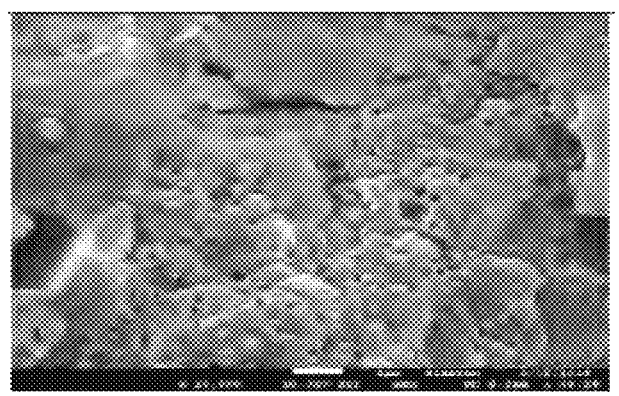
FIG. 37E shows a SEM image of a fractured surface of composites A series.
Figure 38A:
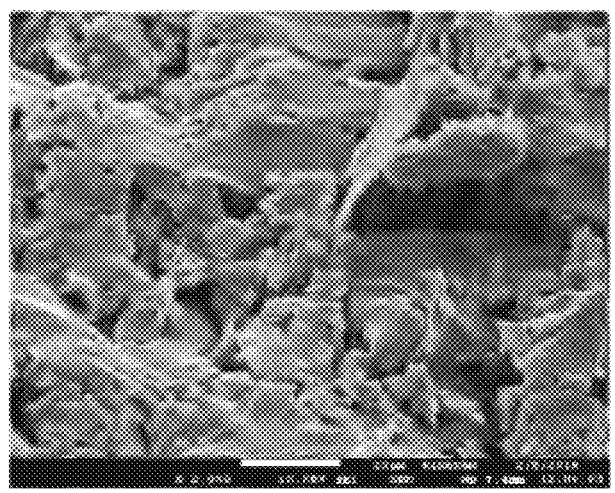
FIG. 38A shows a SEM image of a fractured surface of composites B series.
Figure 38B:
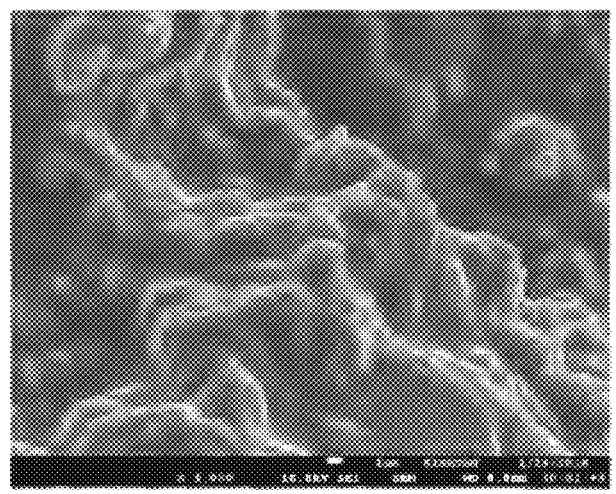
FIG. 38B shows a SEM image of a fractured surface of composites B series.
Figure 38C:
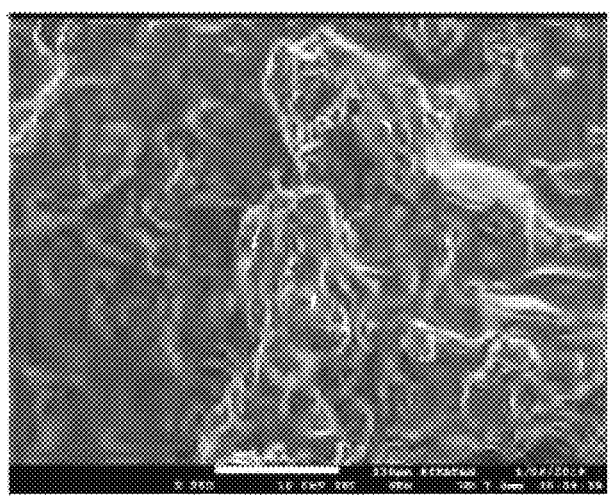
FIG. 38C shows a SEM image of a fractured surface of composites B series.
Figure 38D:
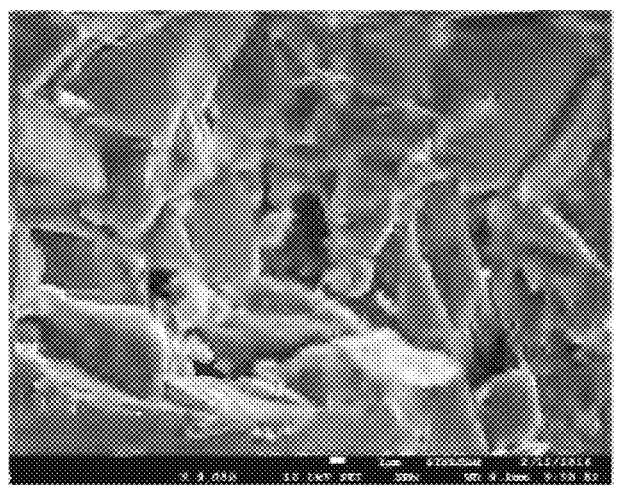
FIG. 38D shows a SEM image of a fractured surface of composites B series.
Figure 38E:
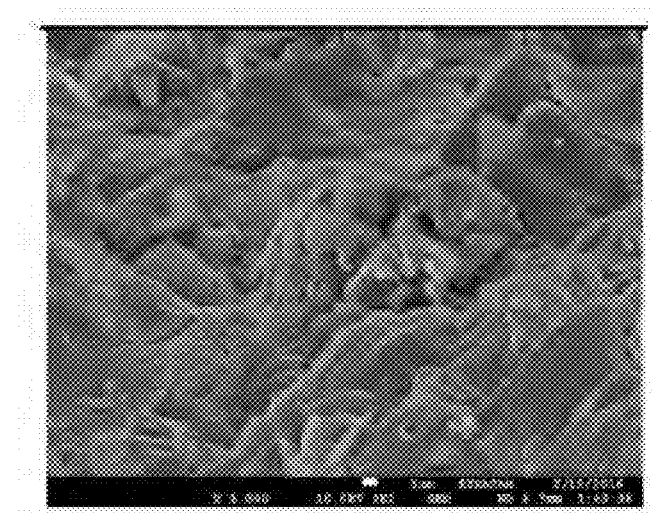
FIG. 38E shows a SEM image of a fractured surface of composites B series.
Figure 39A:
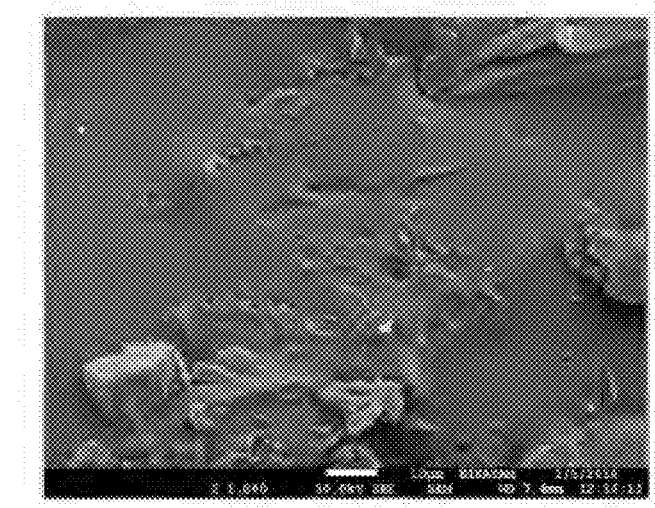
FIG. 39A shows a SEM image of a fractured surface of composites C series.
Figure 39B:
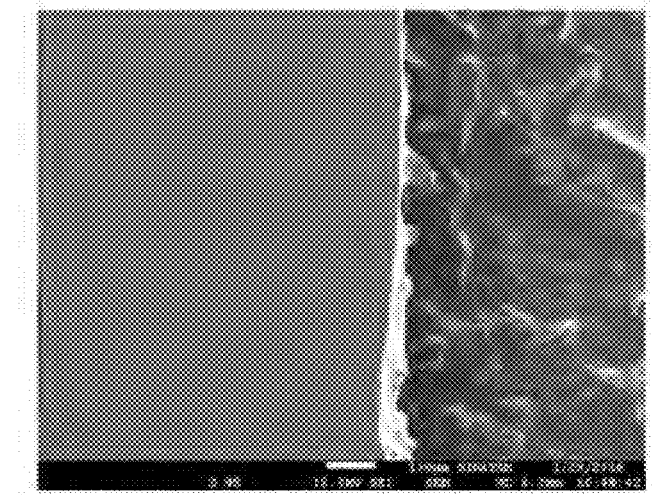
FIG. 39B shows a SEM image of a fractured surface of composites C series.
Figure 39C:
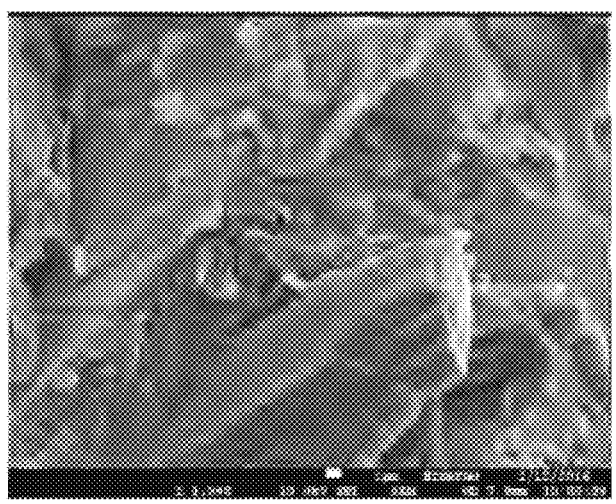
FIG. 39C shows a SEM image of a fractured surface of composites C series.
Figure 39D:
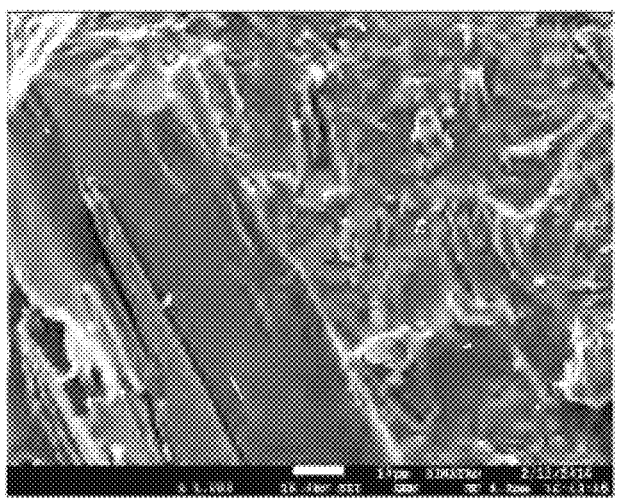
FIG. 39D shows a SEM image of a fractured surface of composites C series.
Figure 40A:
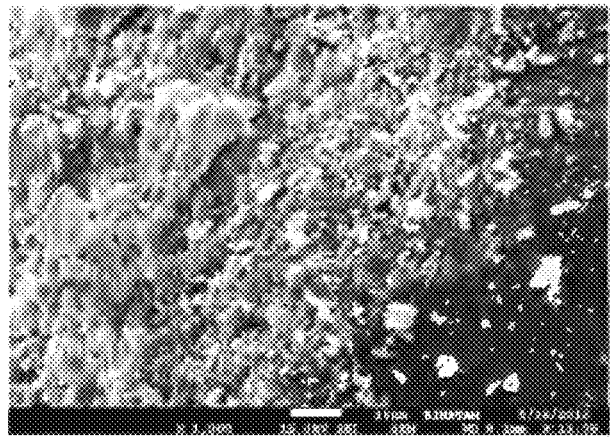
FIG. 40A shows a SEM image of a fractured surface of composites D series.
Figure 40B:
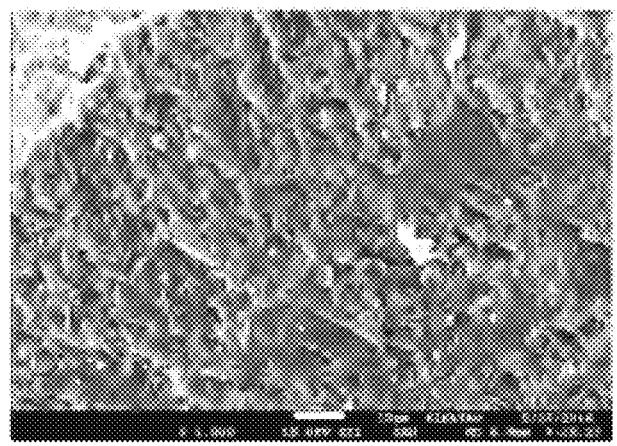
FIG. 40B shows a SEM image of a fractured surface of composites D series.
Figure 40C:
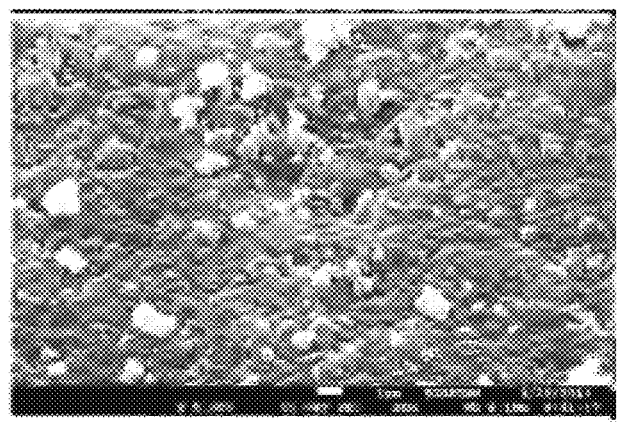
FIG. 40C shows a SEM image of a fractured surface of composites D series.
Figure 40D:
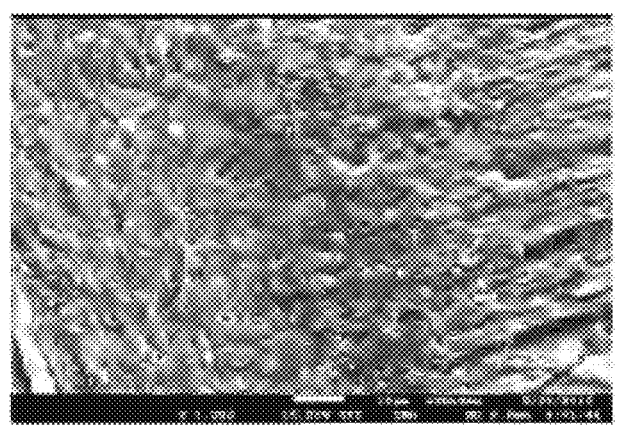
FIG. 40D shows a SEM image of a fractured surface of composites D series.
Figure 40E:
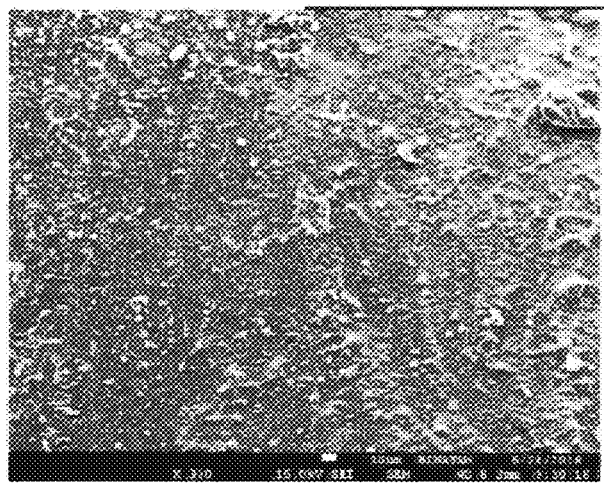
FIG. 40E shows a SEM image of a fractured surface of composites D series.

FT-IR spectra of silica nanoparticles and functionalized silica nanoparticles are shown in FIG. 31. Silica nanoparticles showed strong absorption bands at 3332 $cm^{-1}$ and 1633 $cm^{-1}$ which were assigned to O—H stretching vibration and O—H distorting vibration, respectively. The broad peak at 1063 $cm^{-1}$ is attributed to formation of Si—O—Si. These observed peaks are characteristic silica fingerprint peaks (Cao, X. L., and Fischer, G., "New infrared spectra and the tautomeric studies of purine and alpha L-alanine with an innovative sampling technique", Spectrochimica Acta Part a—Molecular and Biomolecular Spectroscopy, vol. 55, pp. 2329-2342, Sep. 20, 1999; Ma, X.-k., Lee, N.-H., Oh, H.-J., Kim, J.-W., Rhee, C.-K., Park, K.-S., and Kim, S.-J., "Surface modification and characterization of highly dispersed silica nanoparticles by a cationic surfactant", Colloids and Surfaces A: Physicochemical and Engineering Aspects, vol. 358, pp. 172-176, Apr. 5, 2010; and Won, J., Cho, H., and Kang, Y., "The effect of annealing on sSEBS/polyrotaxanes electrolyte membranes for direct methanol fuel cells", Macromolecular Research, vol. 17, pp. 729-733, 2009 Oct. 1, 2009, each incorporated herein by reference in their entirety). Peaks at 1220 $cm^{-1}$ and 1083 $cm^{-1}$ were assigned to Si—O stretching. Absorption peaks at the middle of 954 $cm^{-1}$ is due to stretching of Si—O and Si—O non-bridging oxide. The absorption band at around 795 $cm^{-1}$ is attributed to stretching symmetry of Si—O—Si mode. The absorption bands at 550 $cm^{-1}$ and 470 $cm^{-1}$ were resulted from perpendicular rocking motions to the Si—O—Si plane and the bridging oxygen adjacent to two Si atoms that formed tri- or tetra-siloxane rings (Chuang, S.-W., Hsu, S. L.-C., and Liu, Y.-H., "Synthesis and properties of fluorine-containing polybenzimidazole/silica nanocomposite membranes for proton exchange membrane fuel cells", Journal of Membrane Science, vol. 305, pp. 353-363, Nov. 15, 2007, incorporated herein by reference in its entirety).

The peak at 900 $cm^{-1}$ was due to stretching vibration of epoxy groups. This peak disappeared as a result of azole functionalization (Aslan, A., and Bozkurt, A., "Bioinspired blend membranes based on adenine and guanine functional poly(glycidyl methacrylate)", Langmuir, vol. 26, pp. 13655-61, Aug. 17, 2010; and Nanjundan, S., Unnithan, C. S., Selvamalar, C. S. J., and Penlidis, A., "Homopolymer of 4-benzoylphenyl methacrylate and its copolymers with glycidyl methacrylate: synthesis, characterization, monomer reactivity ratios and application as adhesives", Reactive & Functional Polymers, vol. 62, pp. 11-24, 2005, each incorporated herein by reference in their entirety). The appearance of absorption bands in the high frequency region from 4000 to 1800 $cm^{-1}$ is resulted from stretching vibrations of —OH, —NH and —$CH_2$ groups. Aromatic and aliphatic C—H absorption modes were observed between 2900 cm$^{-1}$ and 2600 cm$^{-1}$. Intermolecular hydrogen bonding in the form of N—H . . . N were observed as a broad band between 2700 cm$^{-1}$ and 2300 cm$^{-1}$. Azole-functionalized SiO$_2$ exhibits characteristic absorptions at 1577 cm$^{-1}$ and 1450 cm$^{-1}$ corresponding to C=N and C—N stretching of a triazole ring, respectively (Angell, C. L., "100. An infrared spectroscopic investigation of nucleic acid constituents", Journal of the Chemical Society (Resumed), pp. 504-515, 1961, incorporated herein by reference in its entirety). Absorption bands around 1800 cm$^{-1}$ were due to chains and ring skeletal vibrations of H—C—H, C—O, H—N—H, and C—N functionalities. Peaks at 1604 cm$^{-1}$ and 1571 cm$^{-1}$ each belongs to in plane N—H vibration and C—O stretching, whereas an intensive band observed at 1630 cm$^{-1}$ is resulted from the in-plane deformation mode of the NH$_2$ group. Ring vibrations of C—N and C=N bonds as well as deformation mode of CH groups were assigned to a series of five intermediate strong absorptions between 1500 cm$^{-1}$ and 1300 cm$^{-1}$. An additional new peak at 1640 cm$^{-1}$ was assigned to the amine bending vibration.

(ii) Nanocomposites

As shown in FIGS. 32-35, to verify the chemical structure of the functional groups and the filler in each composite series, FT-IR analysis was carried out and the spectra were obtained. The characteristic peaks for dimethacrylate monomers in the composite matrix (bis-GMA-co-TEGDMA) were found in the FT-IR spectra at around 3479 cm$^{-1}$ (medium, wide) due to C—OH groups of bis-GMA (vibration due to stretch), while the small peaks at 3050-3038 cm$^{-1}$ are due to the =C—H bonds. Peaks at 2963-2850 cm$^{-1}$ correspond to —CH$_3$ and —CH$_2$ groups (asymmetric and symmetric stretching, strong and sharp) of all monomers. The strong and narrow peak at 1717-1715 cm$^{-1}$ is due to the C=O group of all methacrylates while the medium, narrow peak at 1637-1635 cm$^{-1}$ is due to the stretch vibration of C=C. An absorbance at 1609-1608 cm$^{-1}$ is also shown and attributed to the aromatic C=C bonds of bis-GMA composite matrix. The peaks at 1170-1169 cm$^{-1}$ are mostly due to C—O bonds. The characteristic asymmetric stretching vibrations of the Si—O bonds are in the range of 1250-950 cm$^{-1}$, whereas the fingerprint region includes many peaks due to vibrations between inorganic atoms and oxygen in the filler. The 4000-500 cm$^{-1}$ regions of each FT-IR spectra are very similar, all showing spectral features related to the chemical structure of bis-GMA and TEGDMA based matrix. FT-IR analysis of all composite series indicates a decreased in the intensity of carbonyl C=O peak at around 1700 cm$^{-1}$ compared to the uncured material. The change in the intensity of the carbonyl C=O stretching is directly related to the composition and degree of polymerization of the dental composites (SOANCA, A., Roman, A., MOLDOVANb, I. P., TUDORAN, L.-B., and ROMINU, M., "Study on thermal behavior, structure and filler morphology of some indirect composite resins", Dig J Nanomater Biostruct, vol. 7, pp. 1071-1081, 2012, incorporated herein by reference in its entirety).

Example 15

Thermo-Gravimetric Analysis (TGA)

TGA is one of the mostly used analytical techniques to determine weight loss of a test sample when it is heated or cooled in a controlled system. It can be used in evaluating thermal resistivity and decomposition temperature of a test material. A typical TGA curve is generated by plotting a percentage of weight loss (% wt) on the X-axis and temperature on the Y-axis. Results from TGA are determined by a number of factors such as mass, volume and physical form of the test sample, the shape and type of use, rate of scan, and surrounding pressure. TGA analysis has several application areas in petrochemical, pharmaceuticals and food industries. Thermal stabilities of composites and modification percentage of functionalized fillers of composites were examined by thermo-gravimetric analysis (TGA) with a Perkin Elmer STA 6000. The sample (~5 mg) was heated from room temperature to 700° C. under N$_2$ atmosphere at a heating rate of 10° C. min$^{-1}$.

Example 16

TGA Analysis (i) Functionalized Filler

Figure 41:
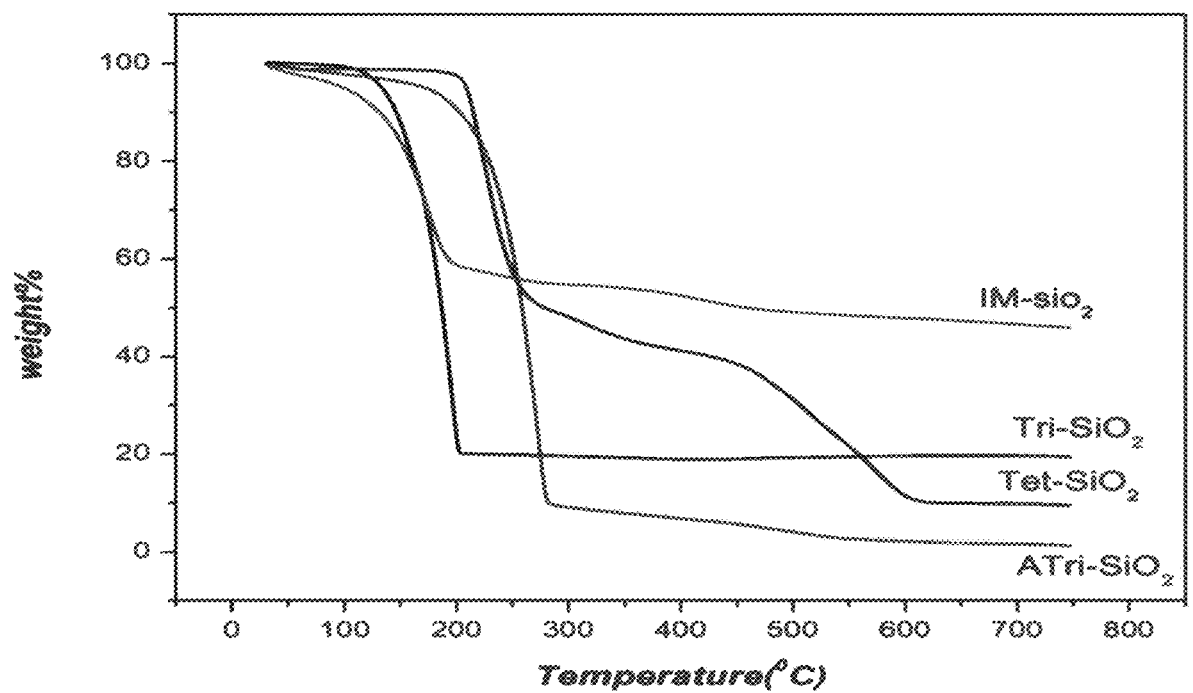
FIG. 41 is an overlay of thermos-gravimetric analysis (TGA) thermo-grams of Tri-SiO$_2$ nanoparticles, ATri-SiO$_2$ nanoparticles, Tet-SiO$_2$ nanoparticles, and Im-SiO$_2$ nanoparticles.
Figure 42:
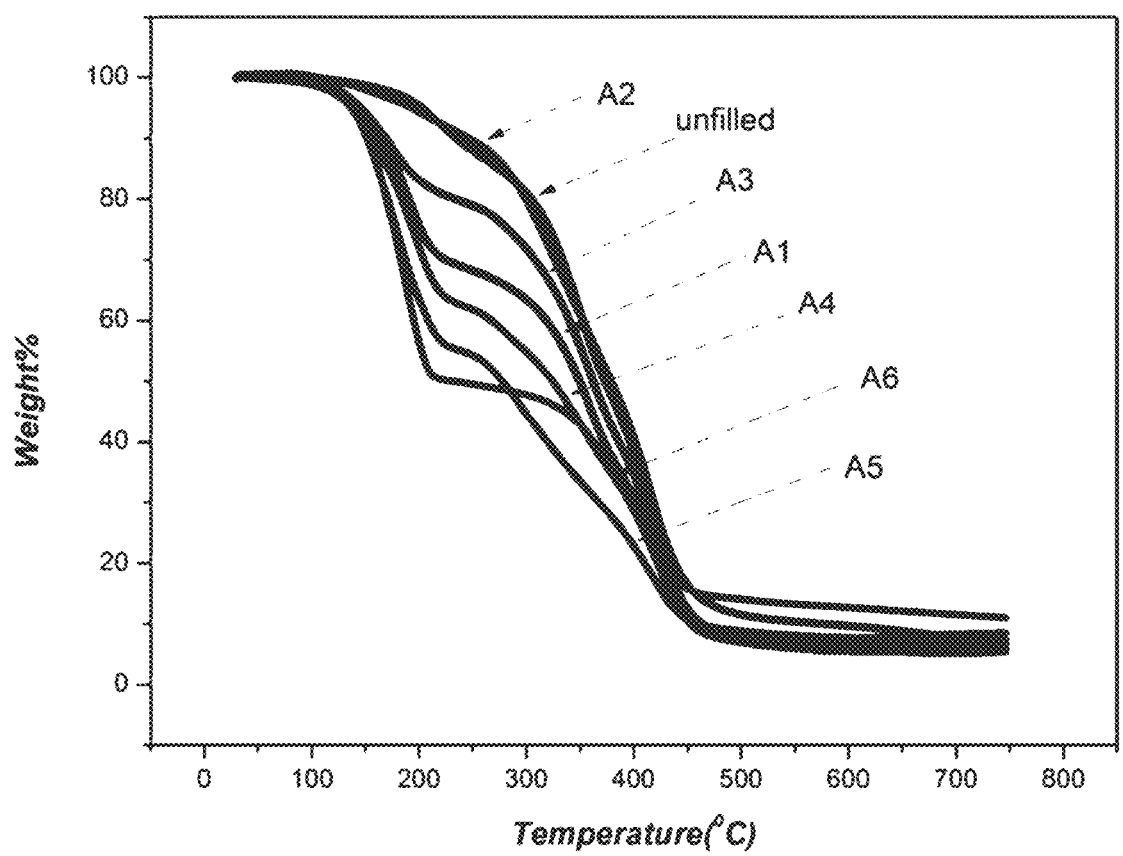
FIG. 42 is an overlay of TGA thermos-grams of composite A series and an unfilled sample.
Figure 43:
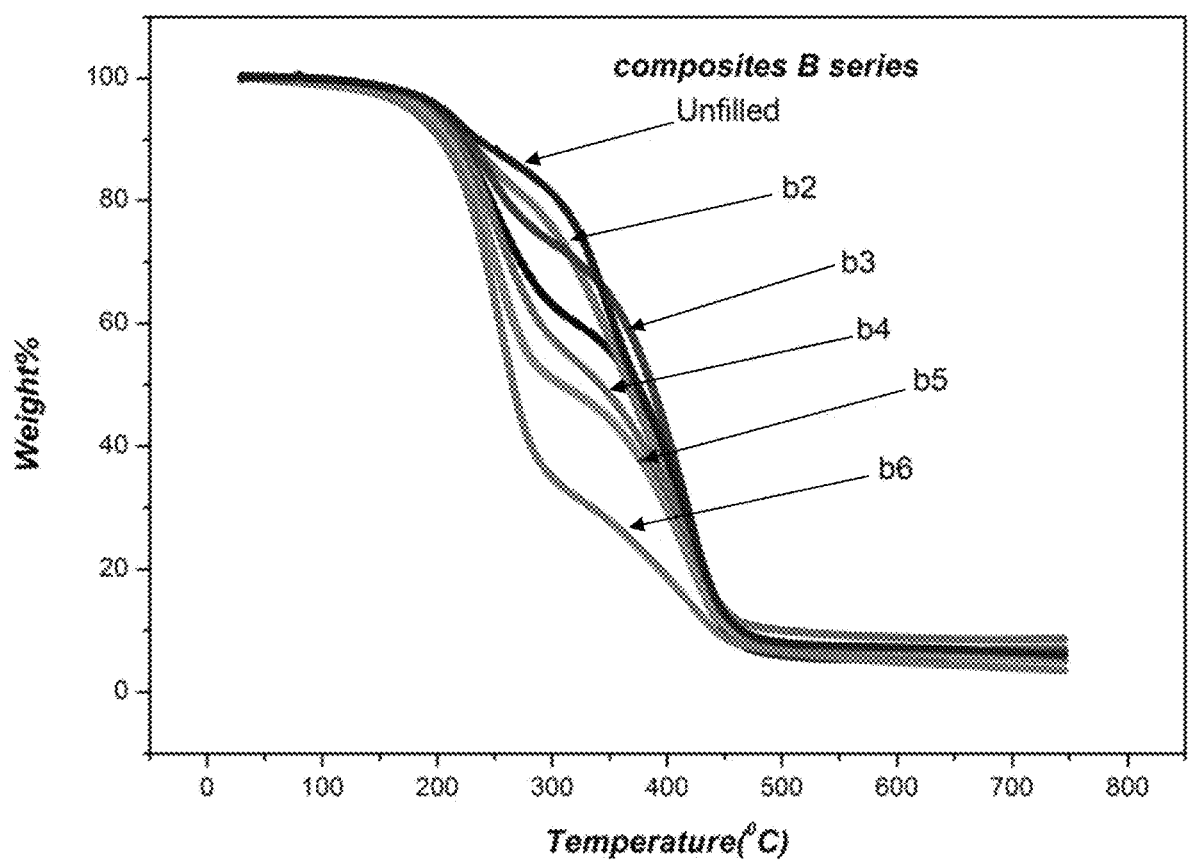
FIG. 43 is an overlay of TGA thermos-grams of composite B series and an unfilled sample.
Figure 44:
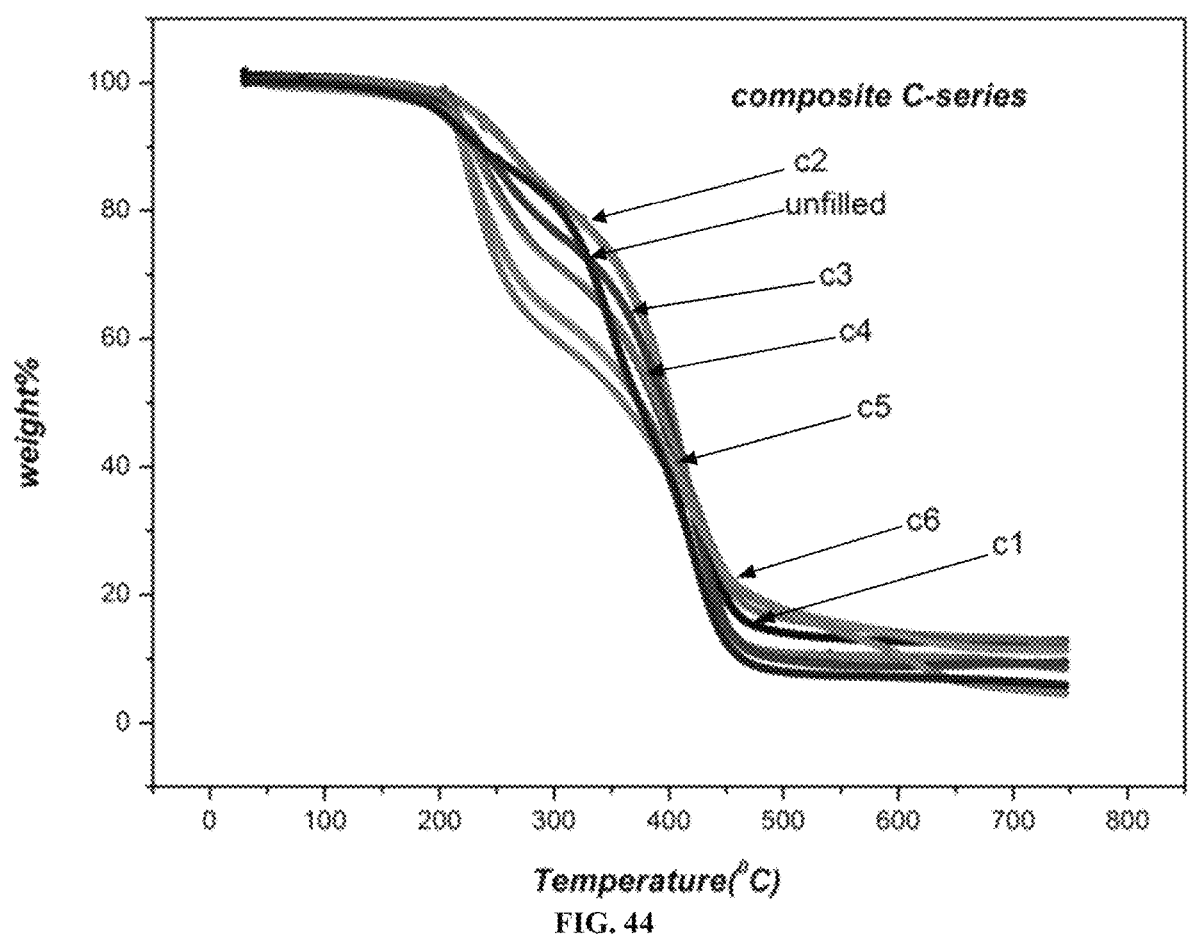
FIG. 44 is an overlay of TGA thermos-grams of composite C series and an unfilled sample.
Figure 45:
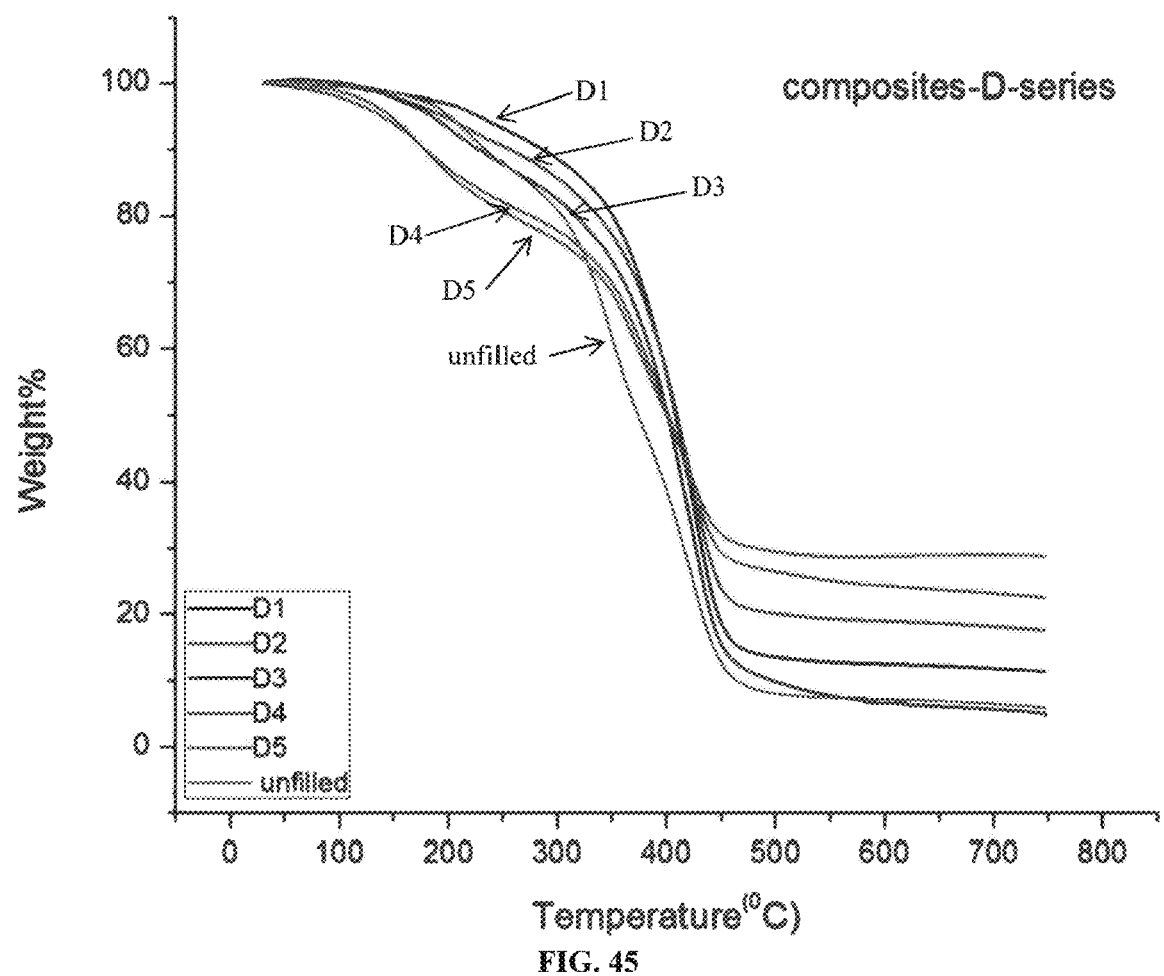
FIG. 45 is an overlay of TGA thermos-grams of composite D series and an unfilled sample.
Figure 46:
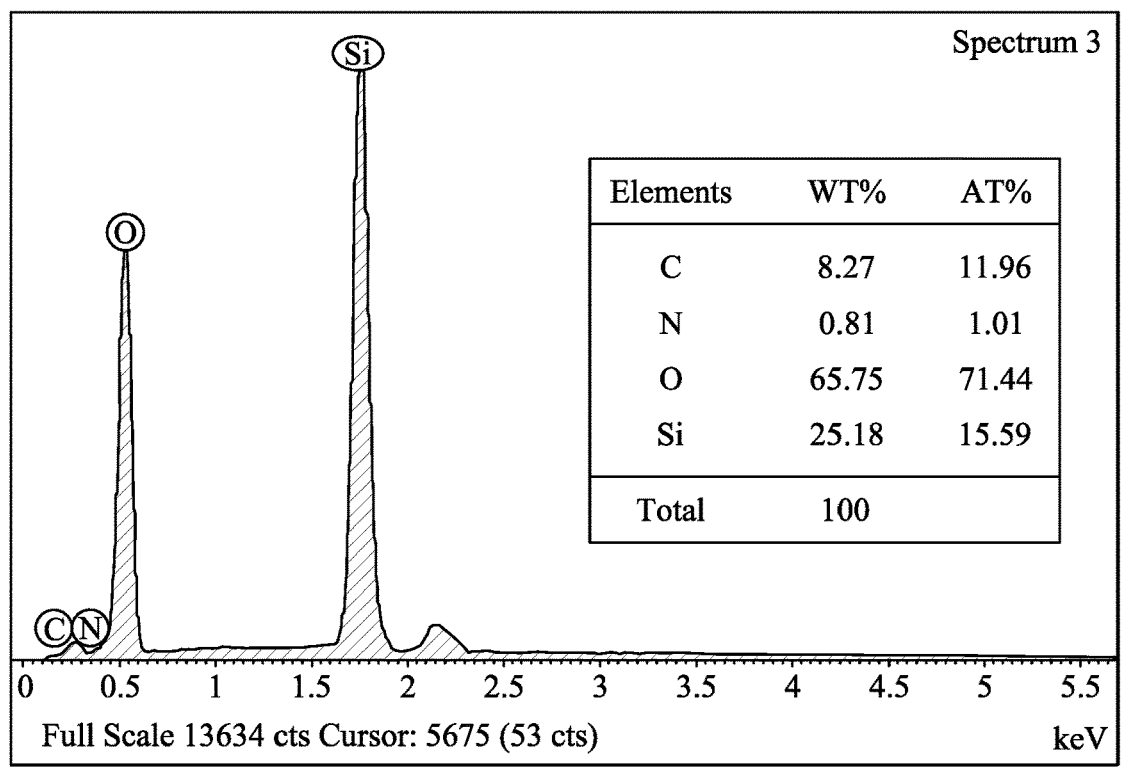
FIG. 46 is an energy-dispersive X-ray spectroscopy (EDX) analysis of Tri-SiO$_2$ nanoparticles.
Figure 47:
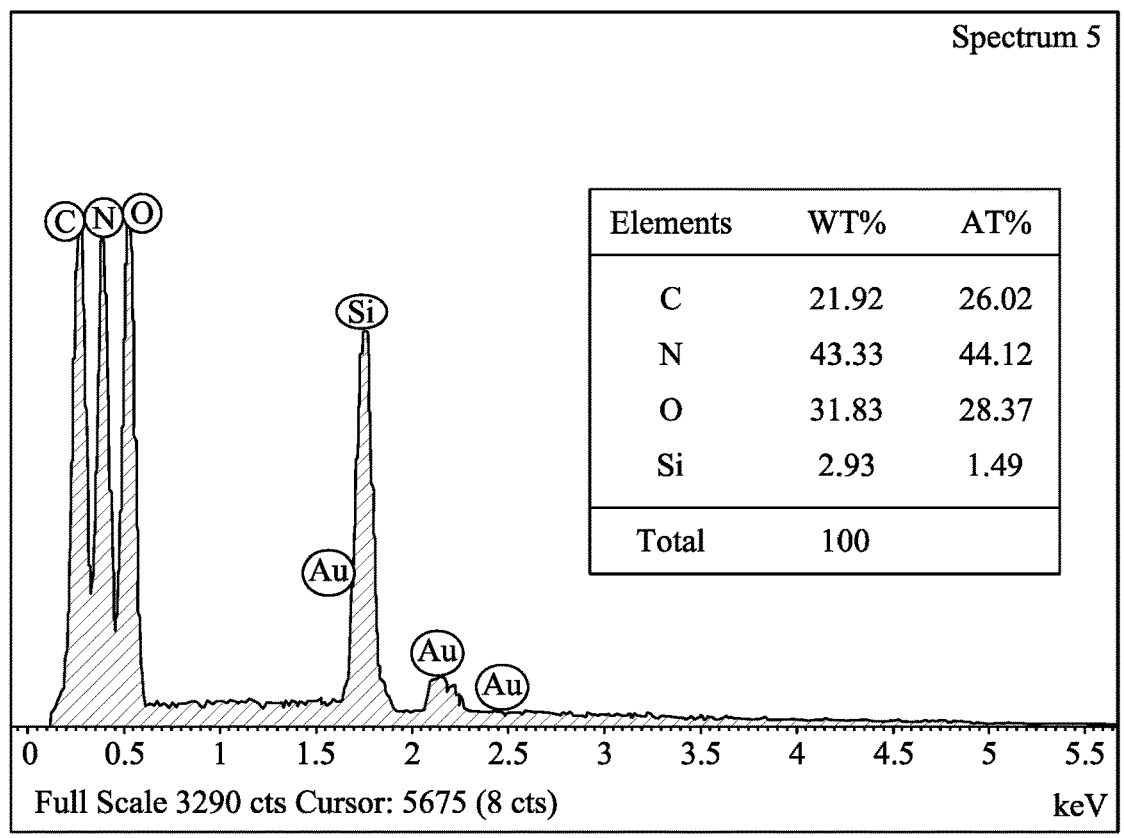
FIG. 47 is an EDX analysis of ATri-SiO$_2$ nanoparticles.
Figure 48:
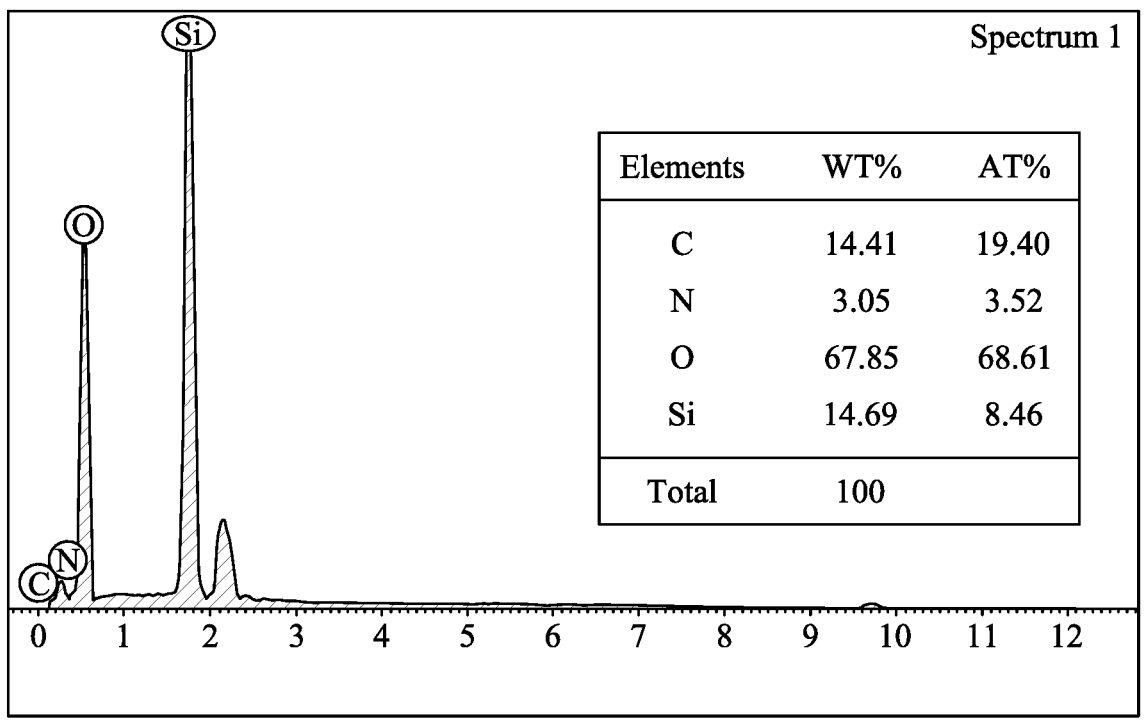
FIG. 48 is an EDX analysis of Tet-SiO$_2$ nanoparticles.
Figure 49:
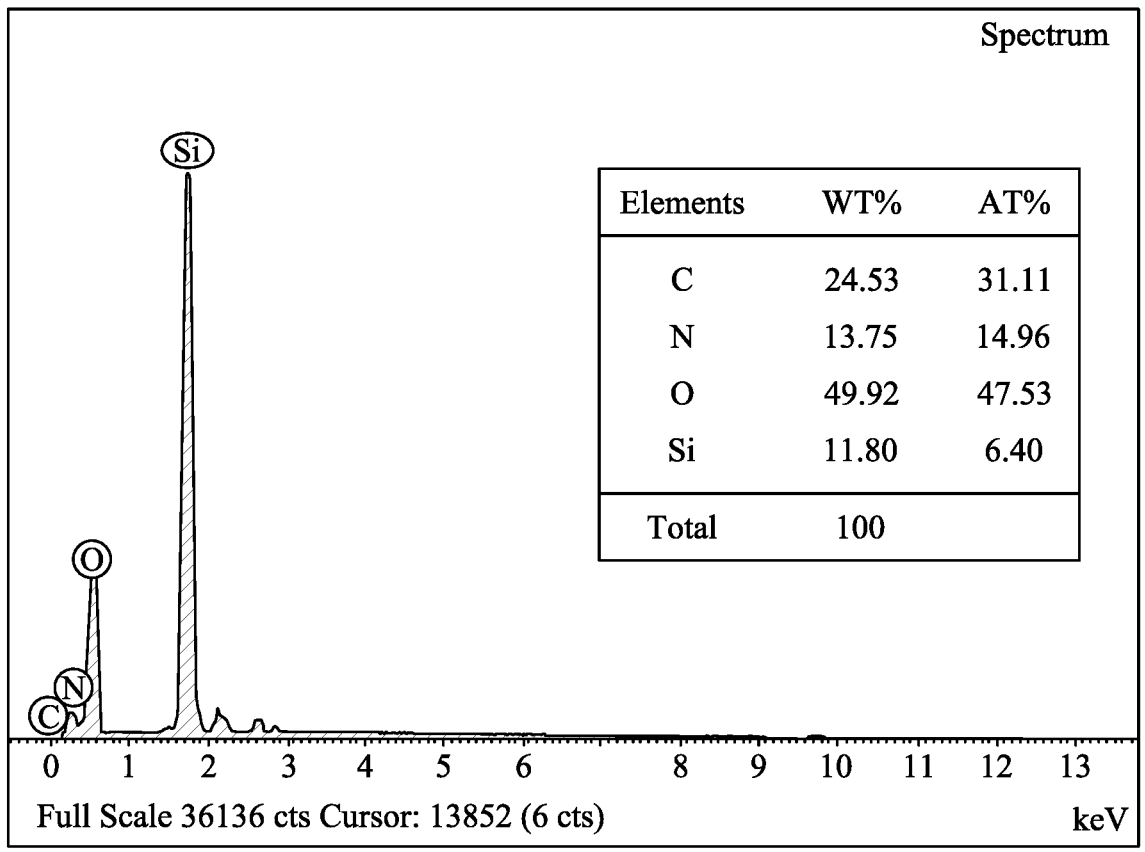
FIG. 49 is an EDX analysis of Im-SiO$_2$ nanoparticles.
Figure 50A:
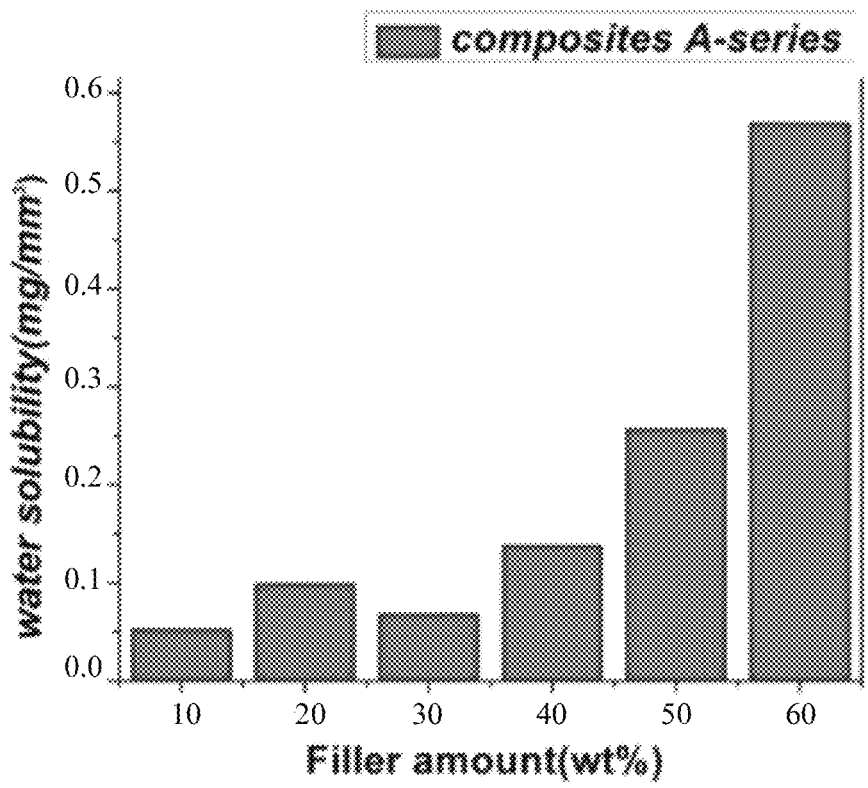
FIG. 50A is a bar graph summarizing water solubility of composite A series.
Figure 50B:
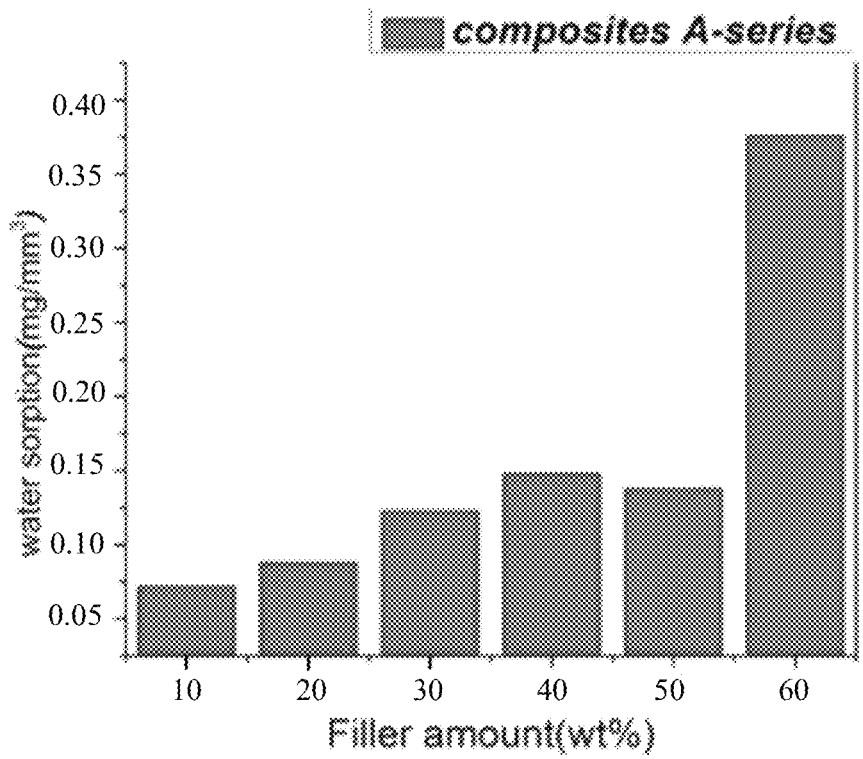
FIG. 50B is a bra graph summarizing water sorption of composite A series.
Figure 51A:
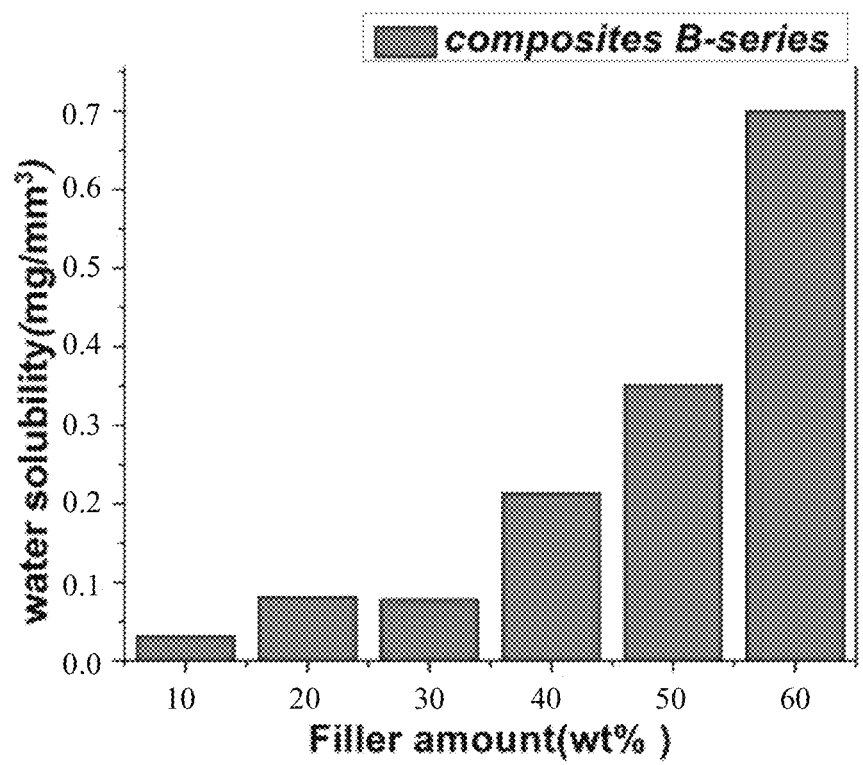
FIG. 51A is a bar graph summarizing water solubility of composite B series.
Figure 51B:
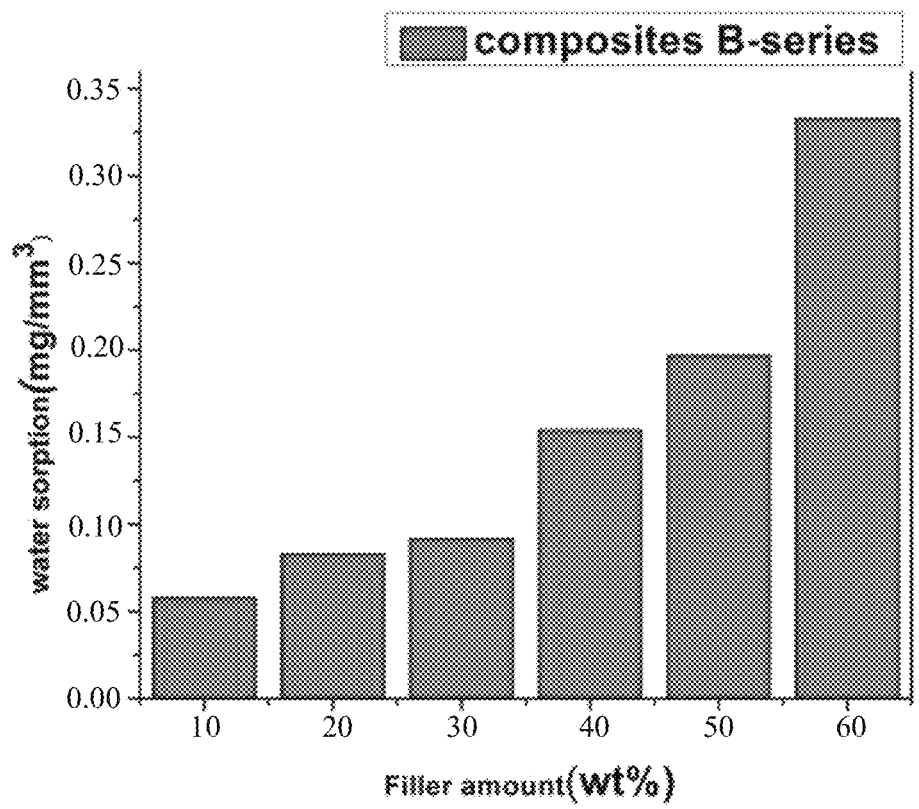
FIG. 51B is a bra graph summarizing water sorption of composite B series.
Figure 52A:
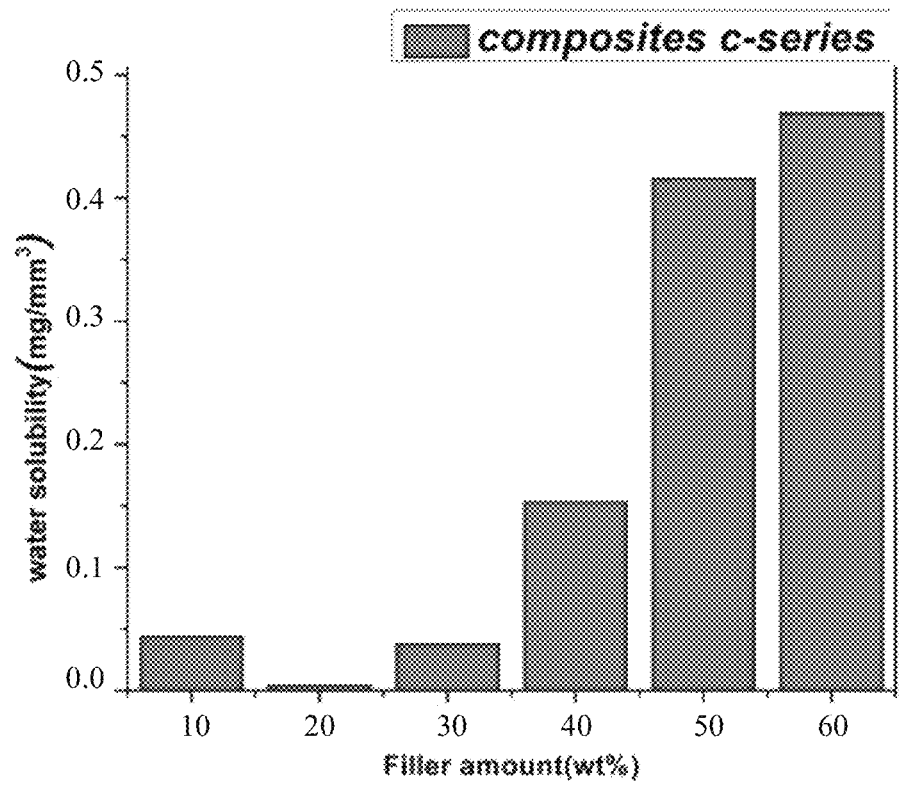
FIG. 52A is a bar graph summarizing water solubility of composite C series.
Figure 52B:
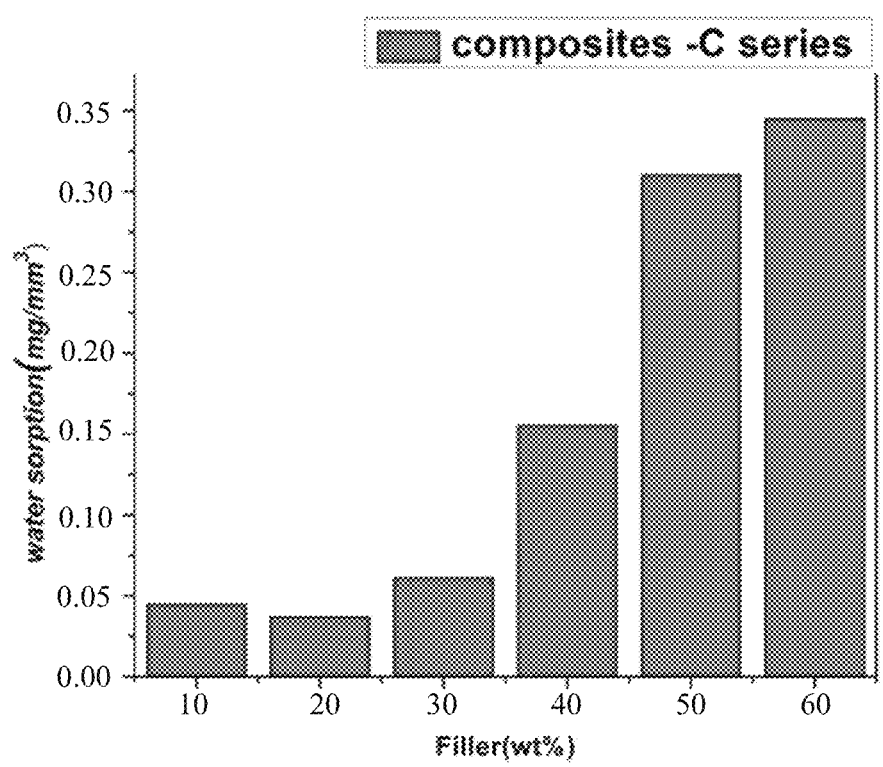
FIG. 52B is a bra graph summarizing water sorption of composite C series.
Figure 53A:
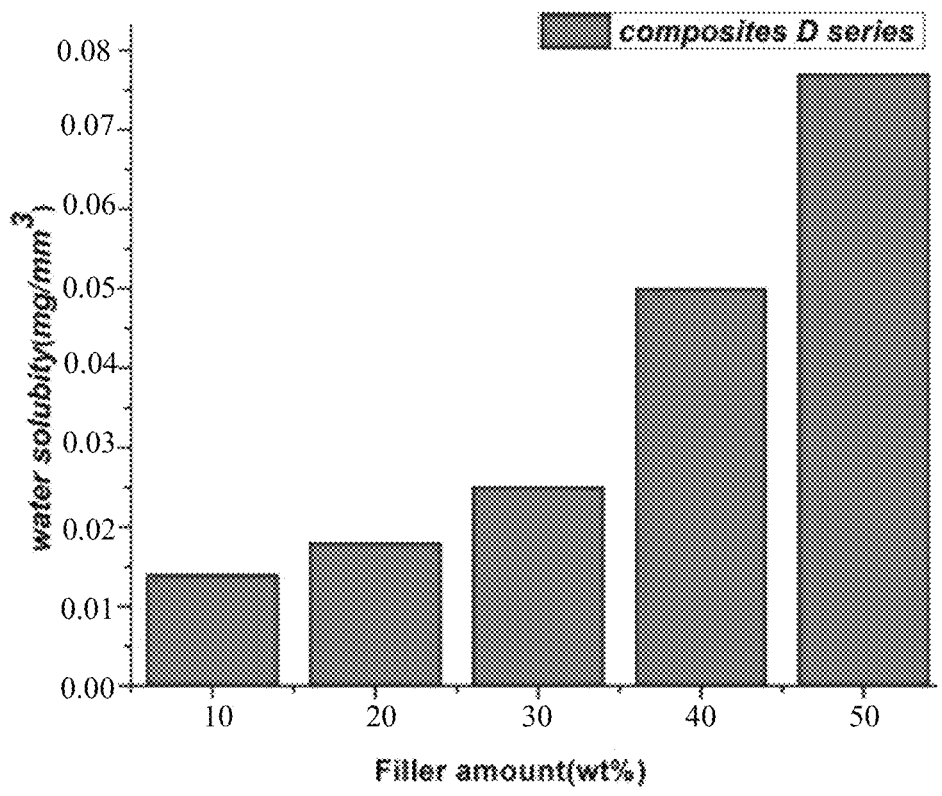
FIG. 53A is a bar graph summarizing water solubility of composite D series.
Figure 53B:
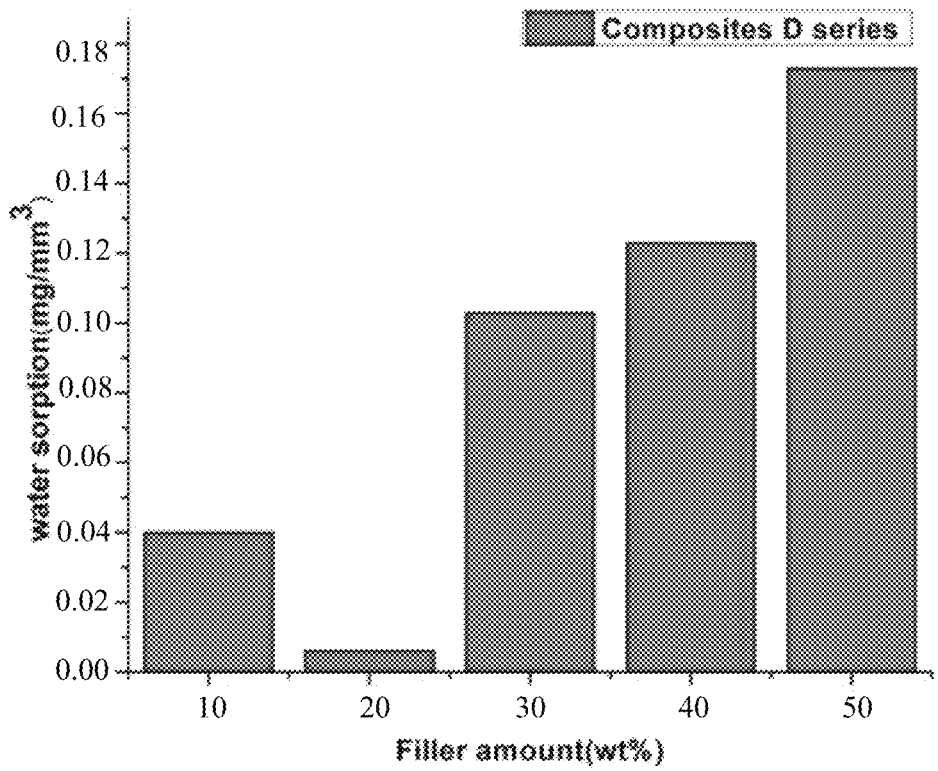
FIG. 53B is a bra graph summarizing water sorption of composite D series.
Figure 54:
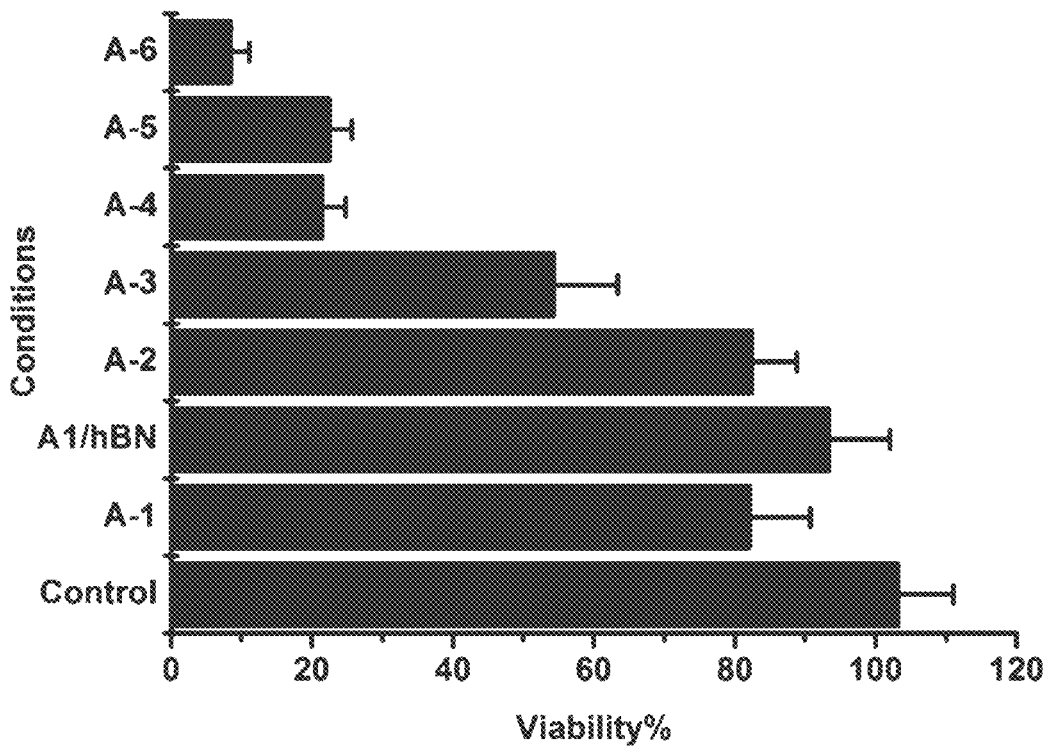
FIG. 54 is bar graph summarizing cell viability mean and standard deviation (SD) of composite A series.
Figure 55:
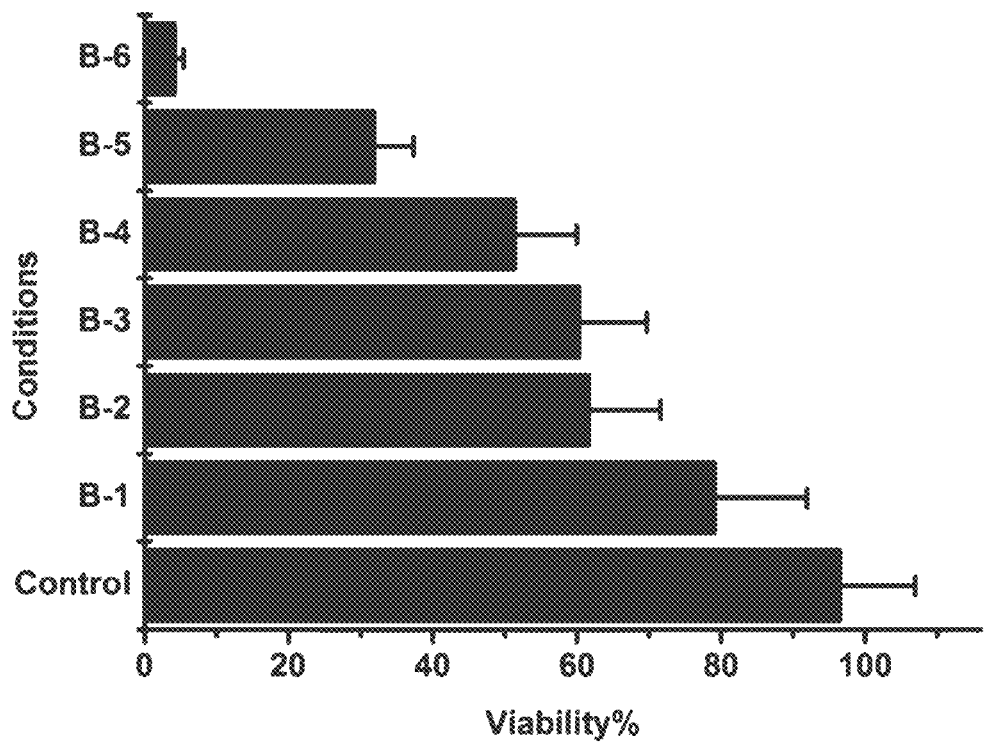
FIG. 55 is bar graph summarizing cell viability mean wand SD of composite B series.
Figure 56:
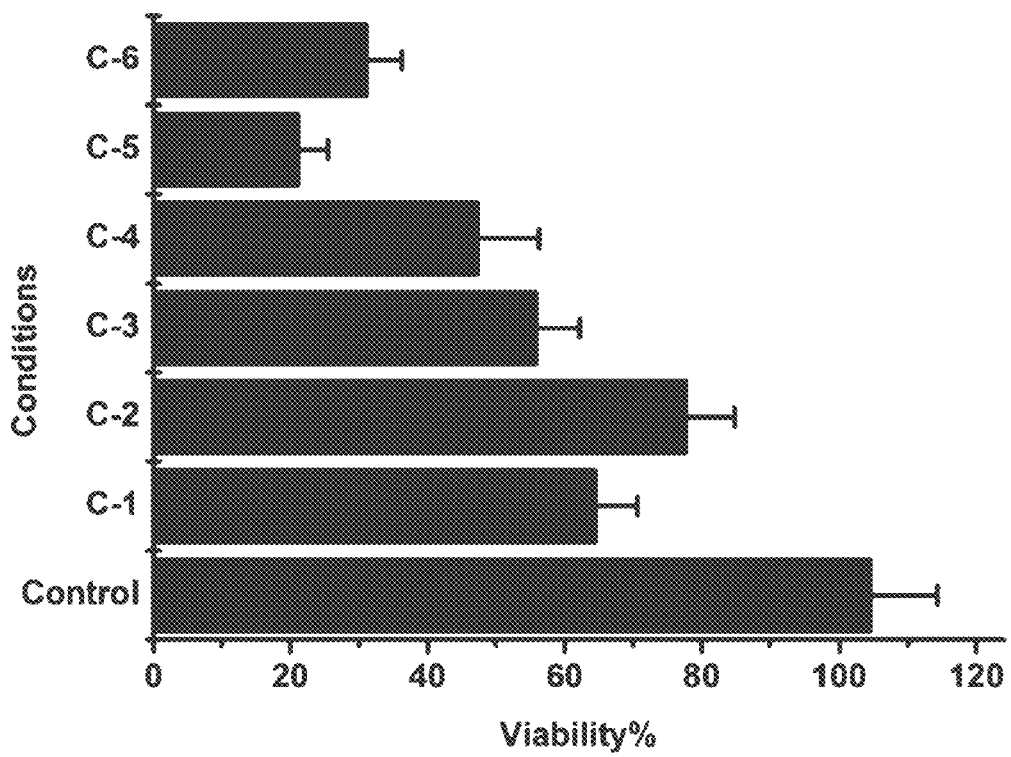
FIG. 56 is bar graph summarizing cell viability mean and SD of composite C series.
Figure 57:
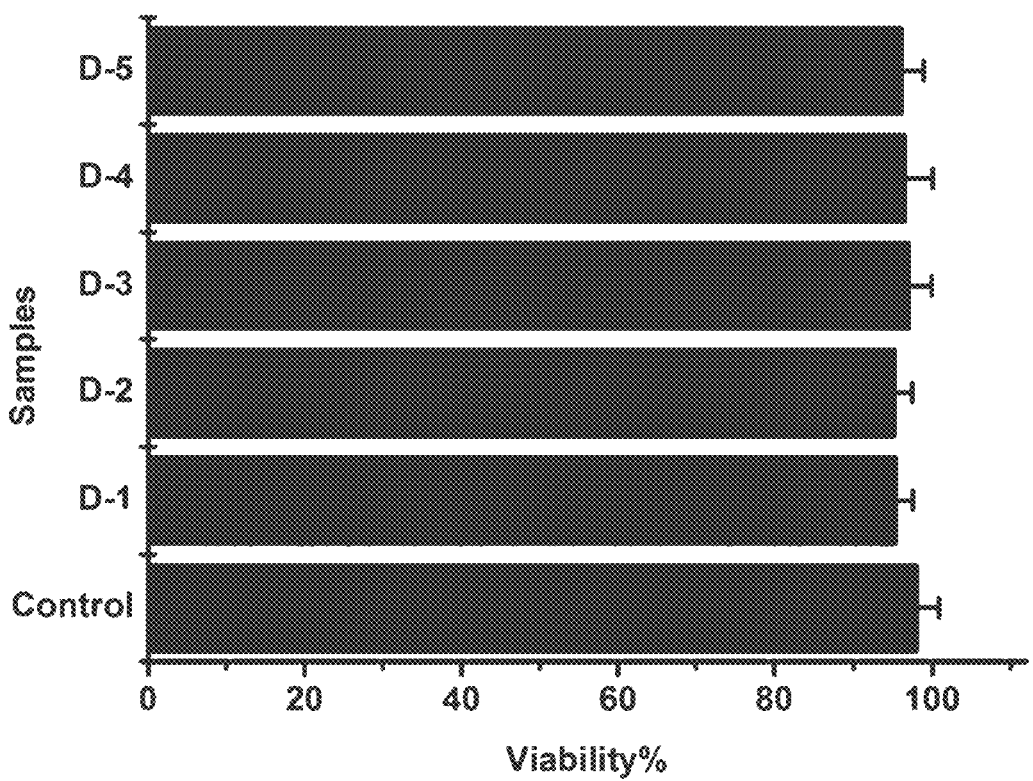
FIG. 57 is bar graph summarizing cell viability mean and SD of composite D series.
Figure 58A:
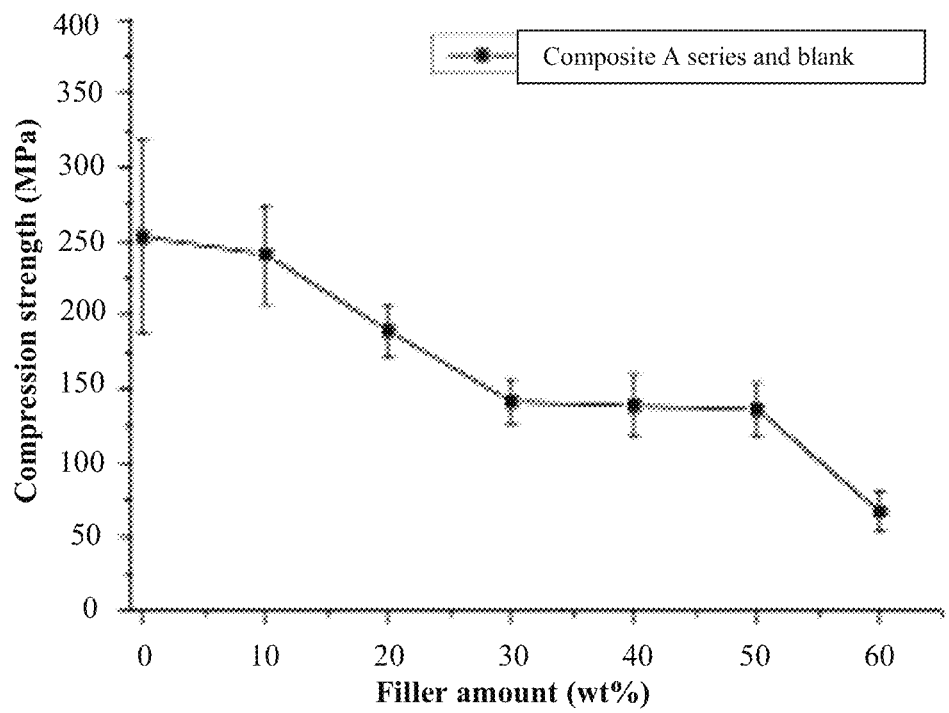
FIG. 58A is a plot of mean and SD summarizing compression strength of composite A series and a blank.
Figure 58B:
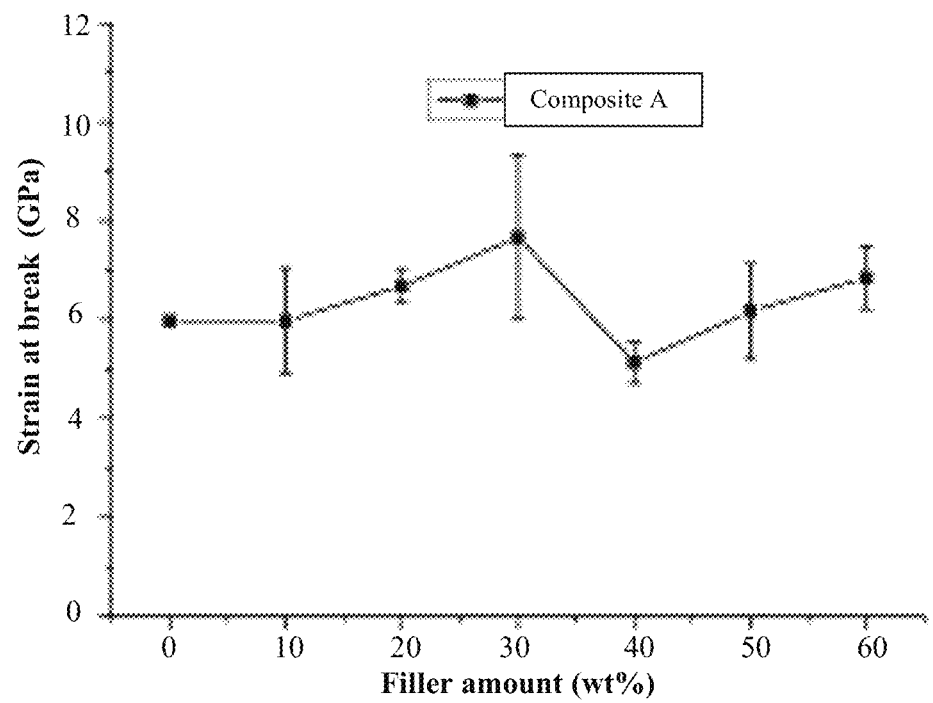
FIG. 58B is a plot of mean and SD summarizing strain at break of composite A series and a blank.
Figure 58C:
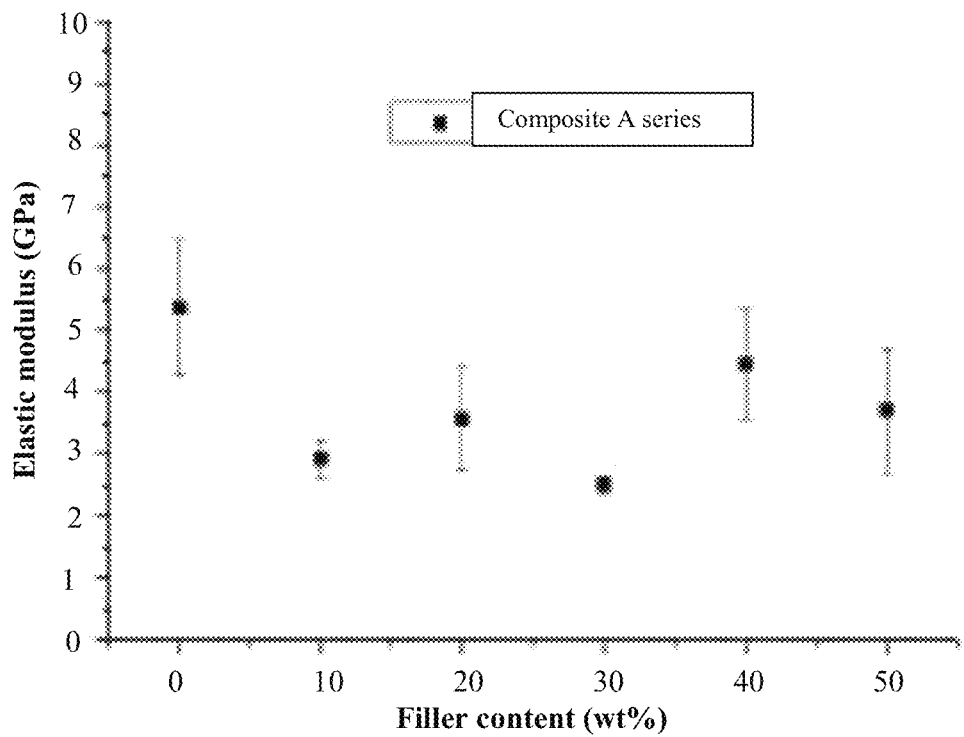
FIG. 58C is a plot of mean and SD summarizing elastic modulus of composite A series and a blank.
Figure 59A:
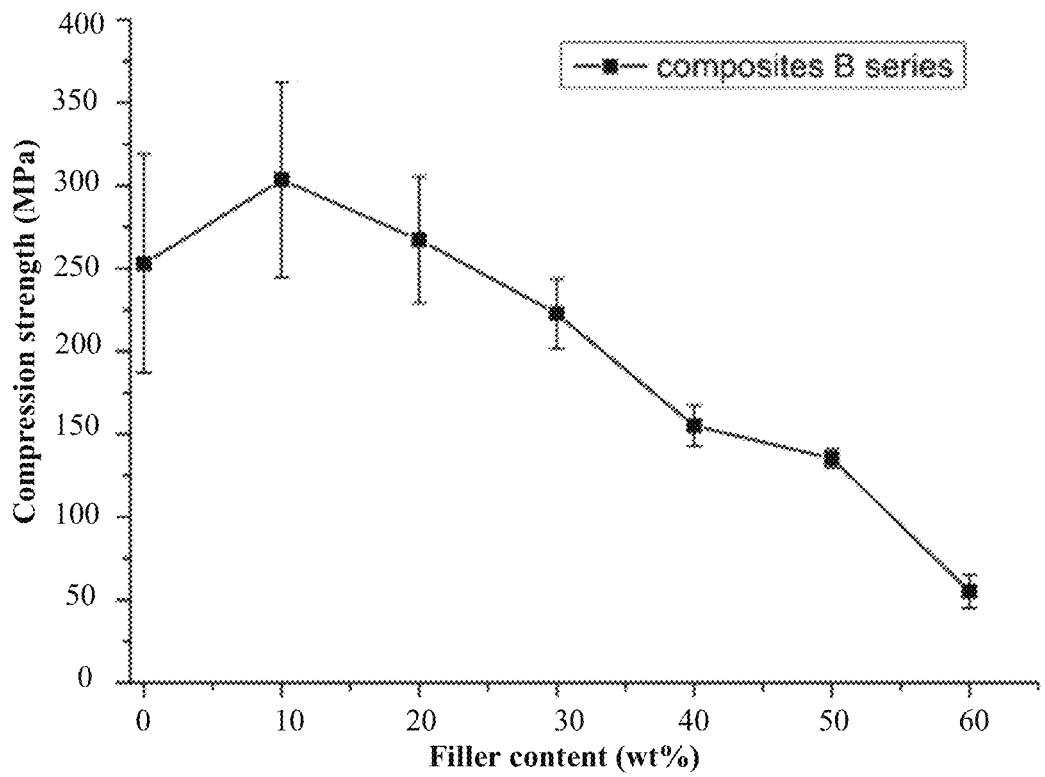
FIG. 59A is a plot of mean and SD summarizing compression strength of composite B series and a blank.
Figure 59B:
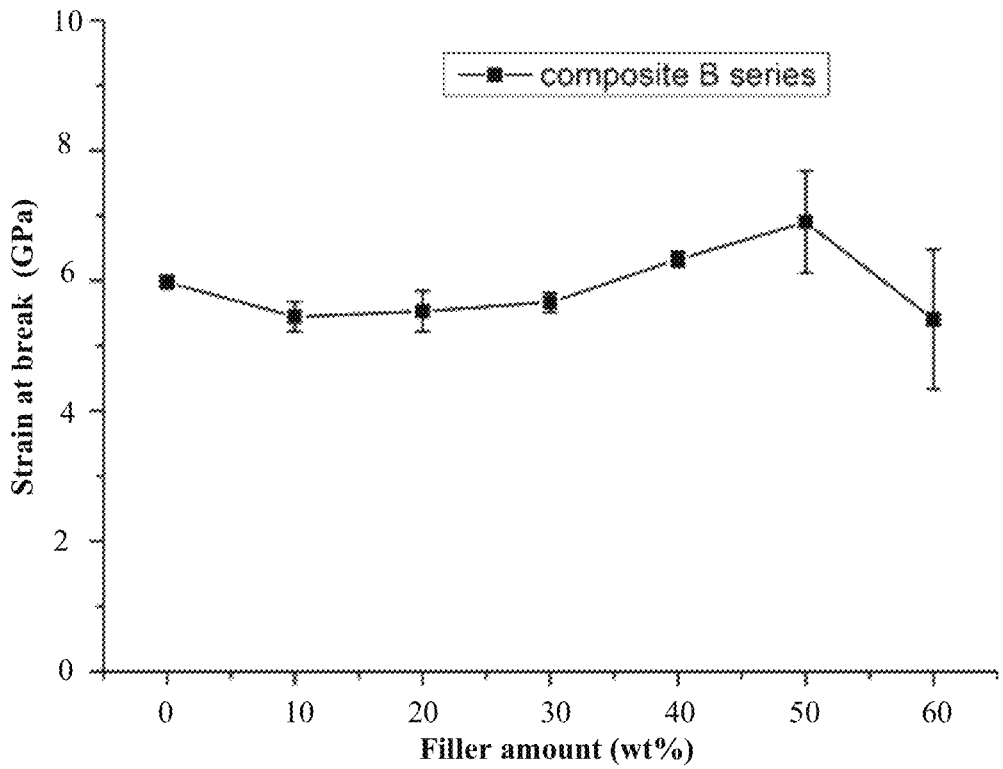
FIG. 59B is a plot of mean and SD summarizing strain at break of composite B series and a blank.
Figure 59C:
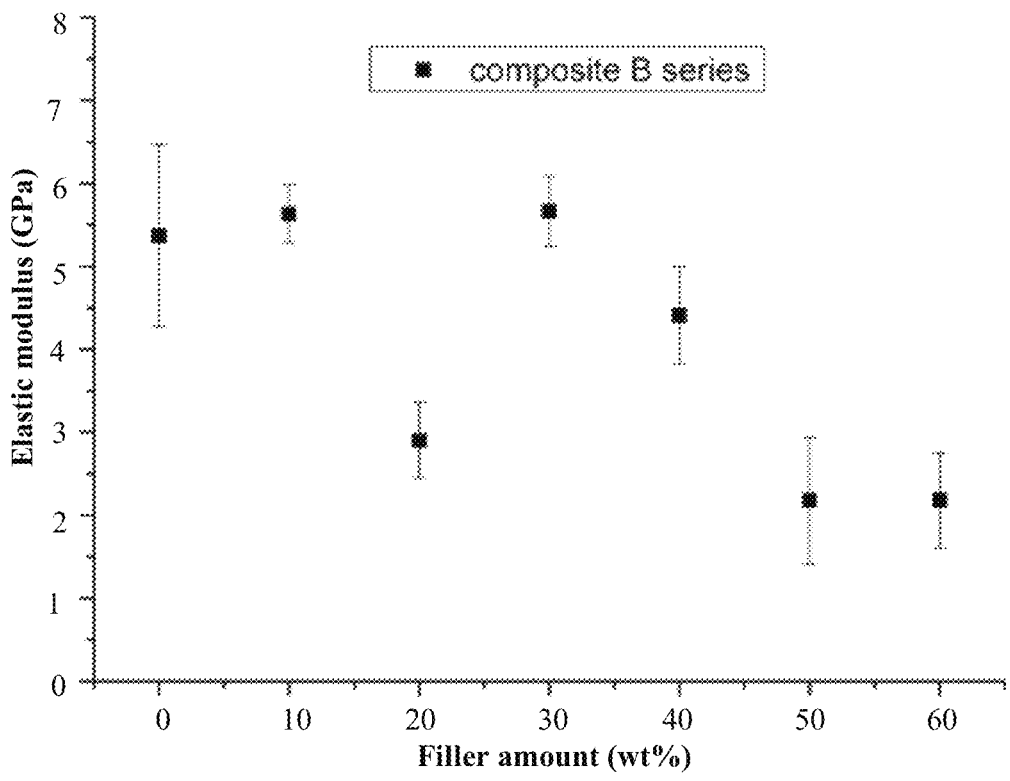
FIG. 59C is a plot of mean and SD summarizing elastic modulus of composite B series and a blank.
Figure 60A:
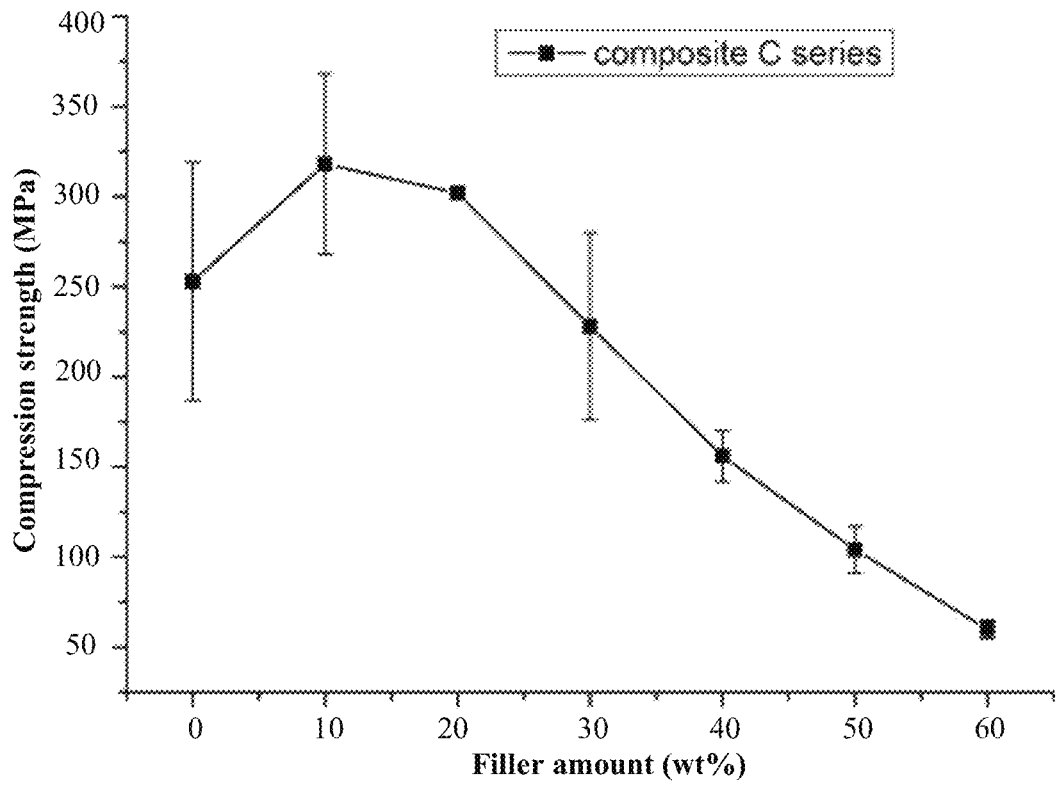
FIG. 60A is a plot of mean and SD summarizing compression strength of composite C series and a blank.
Figure 60B:
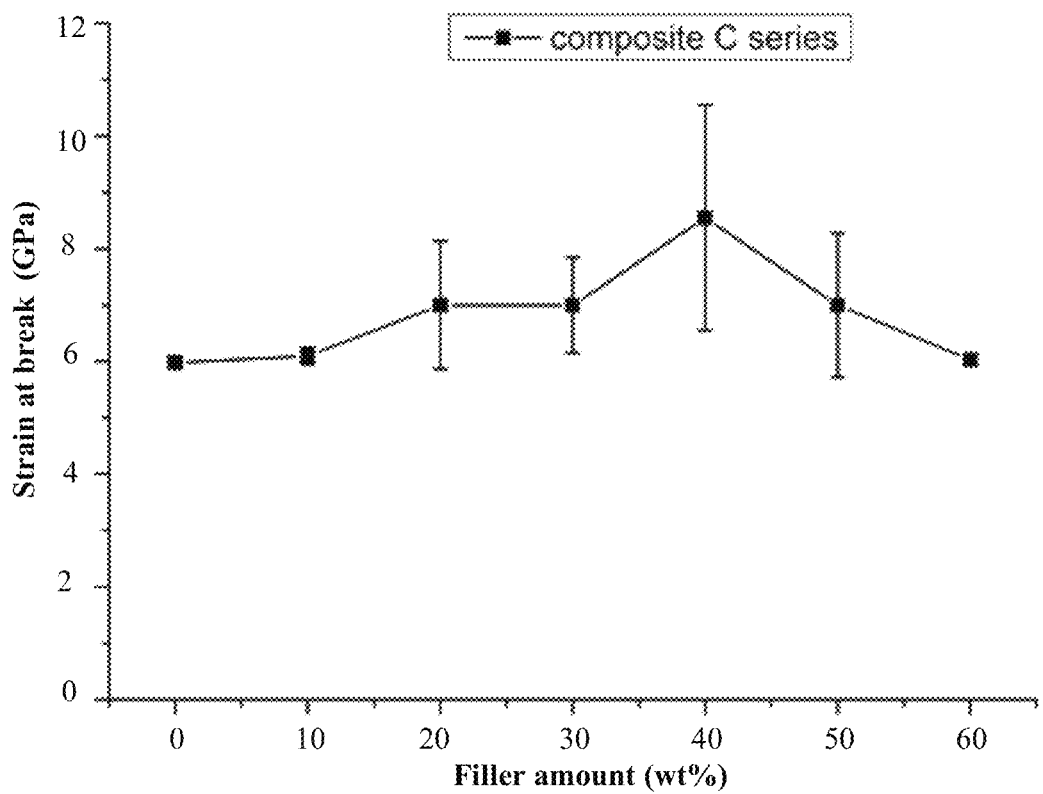
FIG. 60B is a plot of mean and SD summarizing strain at break of composite C series and a blank.
Figure 60C:
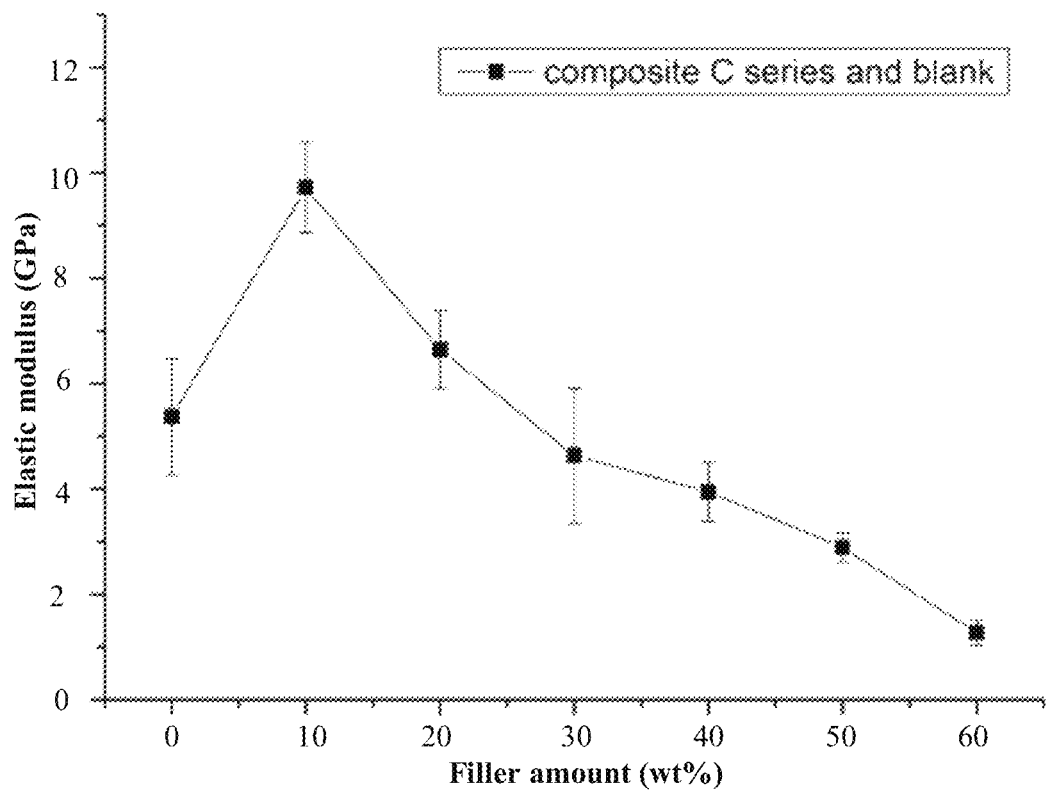
FIG. 60C is a plot of mean and SD summarizing elastic modulus of composite C series and a blank.
Figure 61A:
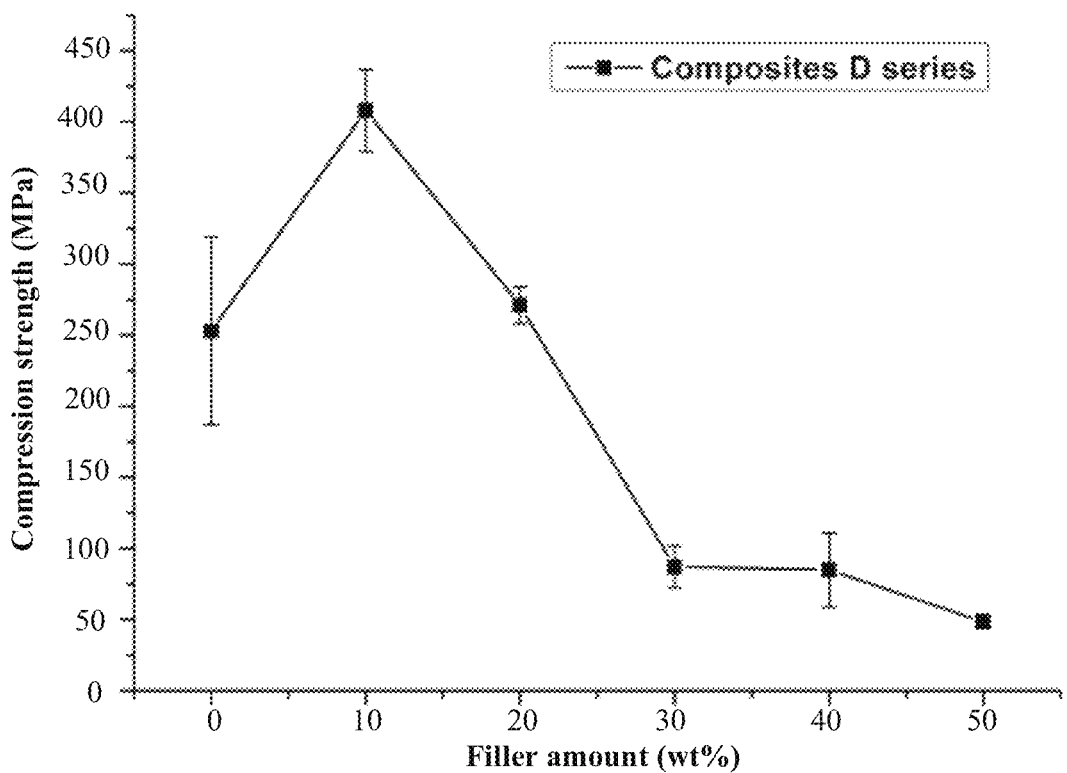
FIG. 61A is a plot of mean and SD summarizing compression strength of composite D series and a blank.
Figure 61B:
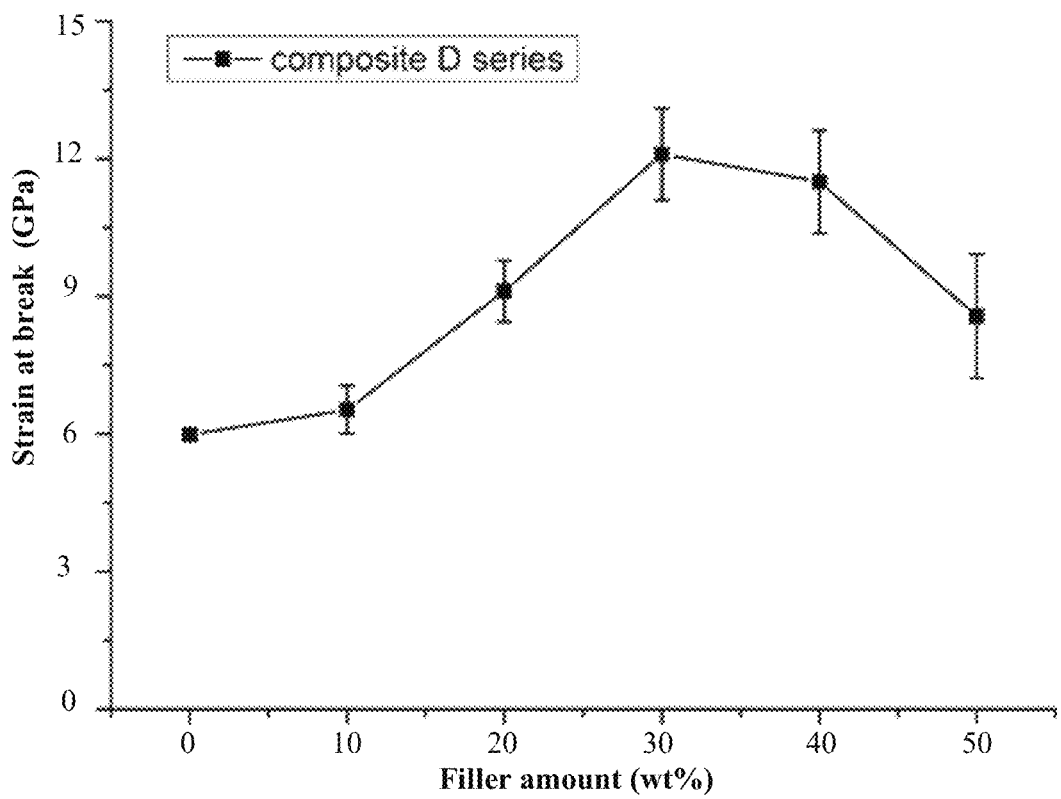
FIG. 61B is a plot of mean and SD summarizing strain at break of composite D series and a blank.
Figure 61C:
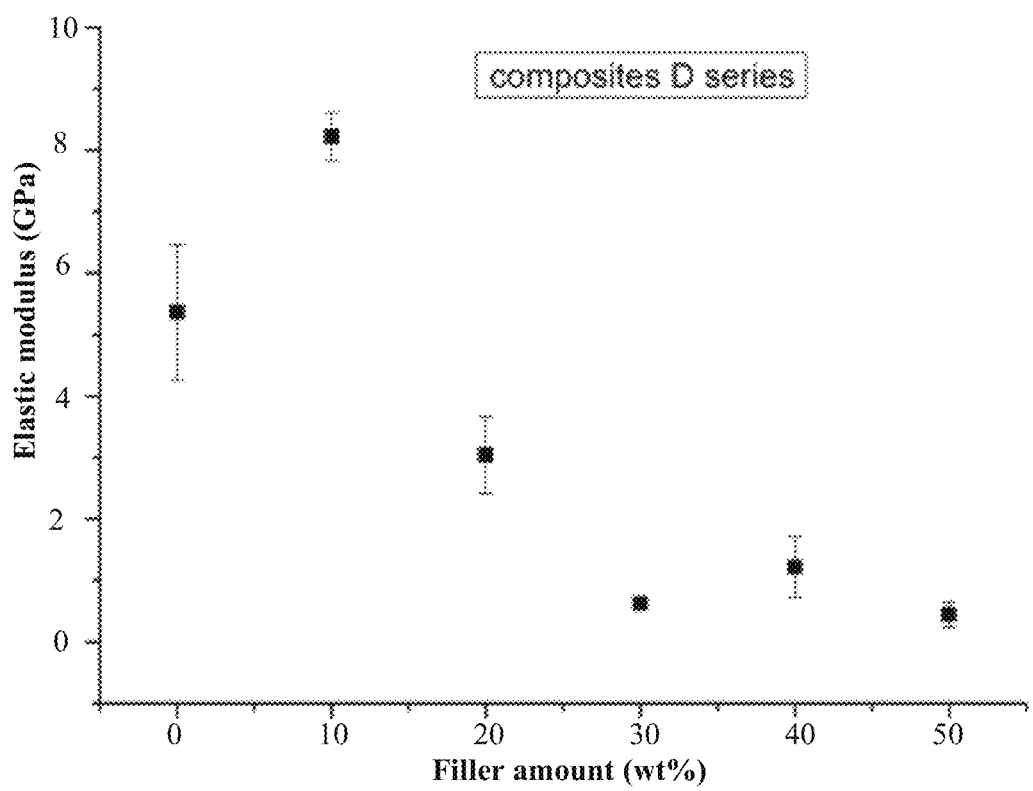
FIG. 61C is a plot of mean and SD summarizing elastic modulus of composite D series and a blank.

In FIG. 41, thermal stability thermos-grams of the functionalized nanoparticles reveal the percentage weight loss. The functionalized fillers are made up of heat resistant nano-silica particles which remain as residue after thermal analysis while bonded azole units are heat decomposable. Initiators also contribute to weight loss. TGA investigations indicate a total weight loss of about 93% in ATri-SiO$_2$ nanoparticles, 90% in Tet-SiO$_2$ nanoparticles, 80% in Tri-SiO$_2$ nanoparticles, and 50% in Im-SiO$_2$ nanoparticles, which correspond to their approximate azole functionalization. Approximately 90% weight loss after heat decomposition observed in some of these functional nanoparticles is consistent with essentially complete functionalization of silica nanoparticles by azole moieties.

(ii) Composites

Representative TGA curves corresponding to composite series A, B, C and D are shown in FIGS. 42-45, respectively. The polymer matrix of the dental resin investigated previously had a three-dimensional cross-linked structure which was highly resistant to thermal decomposition in inert atmosphere. A substantial amount of energy is required to break the bond in a polymer matrix (Achilias, D. S., Karabela, M. M., and Sideridou, I. D., "Thermal degradation of light-cured dimethacrylate resins: Part I. Isoconversional kinetic analysis", Thermochimica Acta, vol. 472, pp. 74-83, 2008, incorporated herein by reference in its entirety). The differential curves show that decomposition of the organic matrix occurs at a temperature lower than 400° C. while mass loss at above 400° C. is due to decomposition of the inorganic phase. Decomposition pattern of monomers (bis-GMA and TEGDMA) is largely affected by their chemical structure (Vouvoudi, E. C., Achilias, D. S., and Sideridou, I. D., "Dental light-cured nanocomposites based on a dimethacrylate matrix: Thermal degradation and isoconversional kinetic analysis in N$_2$ atmosphere", Thermochimica Acta, vol. 599, pp. 63-72, 2015, incorporated herein by reference in its entirety).

Example 17

Scanning Electron Microscopy (SEM)

SEM analysis was used to observe the surface of each functionalized nanoparticles and composite materials. SEM uses a focused electron beam to image a surface. The image is obtained when the surface of a test sample is scanned by a focused electron probe. This allows the collection of signals from the surface of the specimen. The signals are collected from the surface of the specimen. The electron beam loses energy through inelastic scattering as the electrons go through under the surface of the sample.

Electron current generated from an excited sample is mostly due to the release of secondary electrons from the sample surface (Brandon, D., and Kaplan, W. D. Microstructural characterization of materials, John Wiley & Sons, 2013, incorporated herein by reference in its entirety). In this disclosure, surface morphology of the sample was determined using a scanning electron microscope (Philips XL30S-FEG). All samples were gold sputtered before the analysis.

Example 18

SEM Analysis (i) Morphology of Functionalized Silica

As shown in FIGS. 36A-F, surface morphologies of $SiO_2$ nanoparticles, epoxy functionalized $SiO_2$ nanoparticles, Tri-$SiO_2$ nanoparticles, ATri-$SiO_2$ nanoparticles, Tet-$SiO_2$ nanoparticles, and Im-$SiO_2$ nanoparticles were investigated by SEM. Modification on the surface of $SiO_2$ by epoxy, or azole groups such as imidazole clearly gives different images than unmodified silica nanoparticles. After modification of silica nanoparticles with azole compounds via an epoxy ring opening reaction, an increase in the particle size (FIGS. 36A-F) was observed which confirmed the azole modification. After modification, the azole units covered the particle surface which resulted in irregularities in the shape of particles.

(ii) Morphology of Fractured Composites

The morphology of fractured nanocomposite of A, B, C and D series shown in FIGS. 37, 38, 39 and 40 indicate a good dispersion of functionalized fillers in the polymer matrix. As a result, considerable enhancement in mechanical properties of these nanocomposites was observed.

The invention claimed is:

1. A resin composite, comprising:
a polymerizable monomer;
a polymerization initiator system; and
azole-functionalized silica nanoparticles in an amount ranging from 5 wt % to 75 wt % relative to a total weight of the resin composite;
wherein the azole-functionalized silica nanoparticles are a ring-opening reaction product of:
silica nanoparticles modified with epoxide groups; and
an azole moiety,
wherein the silica nanoparticle modified with epoxide groups is represented by formula (I)

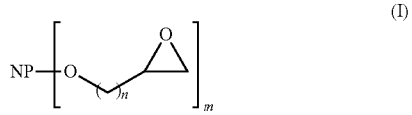

(I)

wherein NP represents a silica nanoparticle;
n is a positive integer in a range of 1-6; and
m is a positive integer in a range of 2-1000.

2. The resin composite of claim 1, wherein silica is present in an amount of 20-50 wt % relative to a total weight of the azole-functionalized silica nanoparticle.

3. The resin composite of claim 1, wherein the azole moiety is present in an amount of 40-80 wt % relative to a total weight of the azole-functionalized silica nanoparticle.

4. The resin composite of claim 1, wherein n is 1.

5. The resin composite of claim 1, wherein the azole moiety is at least one selected from the group consisting of 1H-1,2,4-triazole, 3-amino-1,2,4-triazole, 5-aminotetrazole, and imidazole.

6. The resin composite of claim 1, wherein the azole-functionalized silica nanoparticle has an average diameter of 20-100 nm.

7. The resin composite of claim 1, wherein the polymerizable monomer is at least one selected from the group consisting of a methacrylate monomer, an acrylate monomer, an epoxy monomer, and a vinyl monomer.

8. The resin composite of claim 7, wherein the polymerizable monomer is a methacrylate monomer.

9. The resin composite of claim 8, wherein the methacrylate monomer is at least one selected from the group consisting of bisphenol A-glycidyl methacrylate (bis-GMA), ethoxylated bisphenol A dimethacrylate (bis-EMA), urethane dimethacrylate (UDMA), triethylene glycol dimethacrylate (TEGDMA), 1,12-dodecanediol dimethacrylate ($D_3MA$), bismethacryloyloxymethyltricyclo-[5.2.1.]decane (TCDMA), and 2-hydroxyethyl methacrylate (HEMA).

10. The resin composite of claim 1, wherein the polymerization initiator system comprises a free radical initiator.

11. The resin composite of claim 1, wherein the polymerization initiator system further comprises a polymerization accelerator.

12. The resin composite of claim 1, wherein the polymerization initiator system consists of camphorquinone and ethyl 4-(dimethylamino)benzoate.

13. The resin composite of claim 1, further comprising a filler which is at least one selected from the group consisting of a glass filler, a ceramic filler, and a polymer-based filler.

14. A dental restoration, comprising a cured resin composite of claim 1.

15. The dental restoration of claim 14, which has a compression strength of 40-400 MPa.

16. The dental restoration of claim 14, which has a strain at break of 4.0-13 GPa.

17. The dental restoration of claim 14, which has an elastic modulus of 0.4-11 GPa.

18. The dental restoration of claim 14, which has a water solubility of 0.002-0.4 mg/mL.

19. The dental restoration of claim 14, which has a water sorption of 0.02-0.4 mg/mL.

* * * * *